United States Patent
Reiter et al.

(10) Patent No.: US 8,426,390 B2
(45) Date of Patent: Apr. 23, 2013

(54) TRIAZENE COMPOUNDS FOR THE TREATMENT OF CANCER

(75) Inventors: Rudolf Reiter, Appenzell (CH); Jochen Kalbe, Leichlingen (DE); Heinz Forster, Kadenbach (DE)

(73) Assignee: Trin Therapeutics GmbH, Dusseldorf (DE)

( * ) Notice: Subject to any disclaimer, the term of this patent is extended or adjusted under 35 U.S.C. 154(b) by 54 days.

(21) Appl. No.: 13/205,831

(22) Filed: Aug. 9, 2011

(65) Prior Publication Data

US 2012/0028927 A1 Feb. 2, 2012

Related U.S. Application Data

(62) Division of application No. 12/296,475, filed as application No. PCT/EP2008/058600 on Jul. 3, 2008, now Pat. No. 8,034,797.

(30) Foreign Application Priority Data

Jul. 4, 2007 (EP) ..................................... 07111716

(51) Int. Cl.
*A61K 31/655* (2006.01)
(52) U.S. Cl.
USPC ........................................................... 514/151
(58) Field of Classification Search ........................ None
See application file for complete search history.

(56) References Cited

FOREIGN PATENT DOCUMENTS

GB 1282757 7/1972

OTHER PUBLICATIONS

International Search Report mailed Sep. 16, 2008 for International Application No. PCT/EP2008/058600, two pages.

*Primary Examiner* — Craig Ricci
(74) *Attorney, Agent, or Firm* — Rankin, Hill & Clark LLP

(57) ABSTRACT

The present invention relates to novel triazene compounds, to a process for their preparation, to pharmaceutical compositions comprising them, and to the use thereof in the treatment of cancer diseases in humans. The novel triazene compounds are distinguished, as compared with the known triazene compounds, by improved activity while at the same time having reduced toxicity, that is to say by fewer side-effects.

5 Claims, 38 Drawing Sheets

1H-NMR SPECTRUM (400 MHz) OF THE COMPOUND OF EXAMPLE 1:

CURRENT DATA PARAMETERS

NAME - GI805411-8070247
EXPNO                    2
PROCNO                   1
F2 - ACQUISITION PARAMETERS
DATE_             20080408
TIME                 12.08
INSTRUM              SPECT
PROBHD   5 MM PABBO 13C-1
PULPROG             ZGPG30
TD                   32769
SOLVENT               DMSO
NS                     875
DS                       4
SWH           24038.461 Hz
FIDRES         0.733596 Hz
AQ            0.6816244 SEC
RG                     161
DW            20.800 USEC
DE              6.00 USEC
TE                 294.9 K
D1         2.00000000 SEC
d11        0.03000000 SEC
DELTA      1.89999998 SEC
TD0                      1

======= CHANNEL F1 =======

NUC1                   13C
P1            11.00 USEC
PL1               0.00 dB
SFOF1     400.2300000 MHz

======= CHANNEL F2 =======

CPDPRG2            waltz16
NUC2                    1H
PCPD2         80.00 USEC
PL12             14.78 dB
PL13             14.78 dB
PL2              -1.00 dB
SF02      400.1516006 MHz

F2 - PROCESSING PARAMETERS

SI                   32768
SF        100.6177980 MHz
WDW                     EM
SSB                      0
LB                 1.00 Hz
GB                    0 Hz
PC                    1.40

FIG.2 (CONTINUED)

CURRENT DATA PARAMETERS

NAME - GF701232-7019346
EXPNO                              1
PROCNO                             1

P2 - ACQUISITION PARAMETERS
DATE_              20070208
TIME_                 17.18
INSTRUM              SPECT
PROBHD   5 MM BBO BB 1H
PULPROG               Zg30
TD                   33852
SOLVENT               DMSO
NS                       4
DS                       0
SWH             8278.146 Hz
FIDRES         0.244539 Hz
AQ            2.0447109 SEC
RG                   456.1
DW             60.400 USEC
DE              6.00 USEC
TE                 296.2 K
D1         1.00000000 SEC
TD0                      1
======= CHANNEL F1 =======
NUC1                    1H
P1             10.25 USEC
PL1                -2.00 dB
SPOF1     460.2324716 MHz

F2 - PROCESSING PARAMETERS
SI                   32768
SF         400.2300000 MHz
WDW                     EM
SSB                      0
LB                 0.30 Hz
GB                       0
PL2               -1.00 dB
PC                    0.50

FIG.3 (CONTINUED)

CURRENT DATA PARAMETERS

NAME - GF801747-8058225
EXPNO                        1
PROCNO                       1

P2 - ACQUISITION PARAMETERS
DATE_           20080408
TIME              11.11
INSTRUM           SPECT
PROBHD   5 MM DUL 13C-1
PULPROG            Zg30
TD                32768
SOLVENT             D20
NS                    8
DS                    2
SWH         8223.685 Hz
FIDRES      0.250967 Hz
AQ         1.9923444 SEC
RG                645.1
DW          60.800 USEC
DE           6.00 USEC
TE              295.8 K
D1         2.00000000 SEC
TD0                   1
======= CHANNEL F1 =======
NUC1                 1H
P1           10.25 USEC
PL1             -2.00 dB
SPOF1    400.2324716 MHz

F2 - PROCESSING PARAMETERS
SI                32768
SF       400.2300000 MHz
WDW                  EM
SSB                   0
LB              0.30 Hz
GB                    0
PC                 1.00

FIG.4 (CONTINUED)

CURRENT DATA PARAMETERS

NAME - GF801747-8058225
EXPNO                2
PROCNO               1

P2 - ACQUISITION PARAMETERS
DATE_       20080408
TIME_          10.59
INSTRUM        SPECT
PROBHD   5 MM PABBO BB-
PULPROG        Zgpg30
TD             32768
SOLVENT         DMSO
NS               180
DS                 4
SWH        24038.461 Hz
FIDRES      0.733596 Hz
AQ         0.6816244 SEC
RG              80.6
DW          20.800 USEC
DE           6.00 USEC
TE            295.0 K
D1          2.00000000
D11         0.03000000 SEC
DELTA       1.89999998 SEC
TD0                1

======= CHANNEL F1 =======
NUC1              13C
P1          11.00 USEC
PL1            0.00 dB
SPOF1     100.6278593 MHz

======= CHANNEL F2 =======
CPDPRG2        walt216
NUC2              1H
PCPD2         80.00 MHz
PL12          14.78 dB
PL13          14.78 dB
PL2           -1.00 Hz
SFO2      400.1516006 MHz F2 - PROCESSING PARAMETERS
SI             32768
SF        100.6177980 MHz
WDW               EM
SSB                0
LB             1.00 Hz
GB                 0
PC              1.40

FIG.5 (CONTINUED)

CURRENT DATA PARAMETERS

NAME - GF703450-7054488
EXPNO                  1
PROCNO                 1

P2 - ACQUISITION PARAMETERS
DATE          20070412
TIME              14.11
INSTRUM           SPECT
PROBHD   5 MM DUL 13C-1
PULPROG            Zg30
TD                33852
SOLVENT            DMSO
NS                    8
DS                    2
SWH          8012.820 Hz
FIDRES       0.236702 Hz
AQ          2.1124148 SEC
RG                456.1
DW           62.400 USEC
DE            6.00 USEC
TE              295.6 K
D1         2.00000000 SEC
TD0                   1

======= CHANNEL F1 =======
NUC1                 1C
P1           10.25 USEC
PL1             -2.00 dB
SPOF1      400.2324716 MHz

F2 - PROCESSING PARAMETERS
SI                32768
SF         400.2300000 MHz
WDW                  EM
SSB                   0
LB              0.30 Hz
GB                    0
PC                 0.50

FIG.7 (CONTINUED)

CURRENT DATA PARAMETERS

NAME - GF703450-7054488
EXPNO                 2
PROCNO            1

P2 - ACQUISITION PARAMETERS
DATE_            20070413
TIME              3.33
INSTRUM         SPECT
PROBHD   5 MM DUL 13C-1
PULPROG         Zgpg30
TD               65536
SOLVENT          DMSO
NS                750
DS                  0
SWH          23980.814 Hz
FIDRES        0.365918 Hz
AQ          1.3664756 SEC
RG               256
DW           20.850 USEC
DE            6.00 USEC
TE             297.0 K
D1           2.00000000
d11         0.03000000
DELTA    1.89999998 SEC
TD0              1

======= CHANNEL F1 =======
NUC1               13C
P1             8.65 USEC
PL1             -2.00 dB
SPOF1    100.6479773 MHz

======= CHANNEL F2 =======
CPDPRG2       waltz16
NUC2               1H
PL2              0.00 dB
PL12            15.33 dB
PL13            15.33 dB
SFO2     400.2316009 MHz F2 - PROCESSING PARAMETERS
SI                32768
SF       100.6379140 MHz
WDW               EM
SSB                 0
LB              1.00 Hz
GB                  0
PC               1.40

FIG.8 (CONTINUED)

CURRENT DATA PARAMETERS

NAME - GF708328-7120952
EXPNO                    1
PROCNO                   1

P2 - ACQUISITION PARAMETERS
DATE_           20070727
TIME               10.06
INSTRUM            SPECT
PROBHD   5 MM PABBO BB-
PULPROG             Zg30
TD                 65536
SOLVENT              DSO
NS                     8
DS                     2
SWH          8223.685 Hz
FIDRES       0.125483 Hz
AQ          3.9846387 SEC
RG                   456
DW           60.800 USEC
DE            6.00 USEC
TE               294.8 K
D1        2.00000000 SEC
TD0                    1

======= CHANNEL F1 =======
NUC1                  1H
P1           13.00 USEC
PL1             -1.00 dB
SPOF1   400.1524711 MHz

F2 - PROCESSING PARAMETERS
SI                 65536
SF      400.1500000 MHz
WDW                   EM
SSB                    0
LB              0.30 Hz
GB                     0
PC                  1.40

FIG.9 (CONTINUED)

CURRENT DATA PARAMETERS

NAME - GF708328-7120954
EXPNO                2
PROCNO               1

P2 - ACQUISITION PARAMETERS
DATE_          20070727
TIME              10.08
INSTRUM           SPECT
PROBHD   5 MM PABBO BB-
PULPROG          Zgpg30
TD                65536
SOLVENT            DMSO
NS                  312
DS                    4
SWH        24038.461 Hz
FIDRES      0.366798 Hz
AQ         1.3631988 SEC
RG                  256
DW          20.800 USEC
DE           6.00 USEC
TE              295.3 K
D1       2.00000000 SEC
d1          0.03000000
DELTA    1.89999998 SEC
TD0                   1

======= CHANNEL F1 =======
NUC1                13C
P1          11.00 USEC
PL1             -2.00 dB
SPOF1   100.6278593 MHz

======= CHANNEL F2 =======
CPDPRG2         WALTZ16
NUC2                 1H
PCPD2        80.00 USEC
PL2             14.78 dB
PL12            14.78 dB
PL13            -1.00 dB
SFO2    400.1516006 MHz

F2 - PROCESSING PARAMETERS
SI                32768
SF      100.6177980 MHz
WDW                  EM
SSB                   0
LB             1.00 Hz
GB                    0
PC                 1.40

FIG.10 (CONTINUED)

CURRENT DATA PARAMETERS

NAME - GF804237-8059995
EXPNO                    1
PROCNO                   1

P2 - ACQUISITION PARAMETERS
DATE_         20080324
TIME_            14.34
INSTRUM          SPECT
PROBHD   5 MM DUL 13C-1
PULPROG           Zg30
TD               33852
SOLVENT           DMSO
NS                  36
DS                   2
SWH         8012.820 Hz
FIDRES      0.236702 Hz
AQ         2.1124148 SEC
RG              1149.4
DW          62.400 USEC
DE           6.00 USEC
TE             296.6 K
D1       2.00000000 SEC
TD0                  1

======= CHANNEL F1 =======
NUC1                1H
P1          13.70 USEC
PL1            0.00 dB
SPOF1    400.2324714 MHz

F2 - PROCESSING PARAMETERS
SI               32768
SF       400.2300000 MHz
WDW                 EM
SSB                  0
LB            0.30 Hz
GB                   0
PC                1.00

FIG.13 (CONTINUED)

CURRENT DATA PARAMETERS

NAME - GF804237-8059995
EXPNO                  2
PROCNO                 1

P2 - ACQUISITION PARAMETERS
DATE_            20080324
TIME                14.43
INSTRUM             SPECT
PROBHD   5 MM DUL 13C-1
PULPROG            Zgpg30
TD                  32768
SOLVENT              DMSO
NS                    400
DS                      2
SWH          24154.590 Hz
FIDRES         0.737140 Hz
AQ            0.6783476 SEC
RG                   3251
DW              20.700 USEC
DE               6.00 USEC
TE                296.8 K
D1           2.00000000 SEC
D11          0.03000000 SEC
DELTA        1.89999998 SEC
TD0                     1

======= CHANNEL F1 =======
NUC1                  13C
P1               9.30 USEC
PL1                -1.00 dB
SPOF1        100.6479773 MHz

======= CHANNEL F2 =======
CPDPRG2           waltz16
NUC2                   1H
PCPD2           80.00 USEC
PL2                -2.00 dB
PL12               15.00 dB
PL13               15.00 dB
SFO2         400.2316009 MHz F2 - PROCESSING PARAMETERS
SI                  32768
SF           100.6379554 MHz
WDW                    EM
SSB                     0
LB                1.00 Hz
GB                      0
PC                   1.40

FIG.14 (CONTINUED)

CURRENT DATA PARAMETERS

NAME - GF715523-7218378
EXPNO             1
PROCNO            1

P2 - ACQUISITION PARAMETERS
DATE_         20071220
TIME            11.28
INSTRUM         SPECT
PROBHD   5 MM BBO BB-1H
PULPROG          Zg30
TD              32768
SOLVENT          DMSO
NS                  8
DS                  2
SWH        8223.665 Hz
FIDRES     1.992344 Hz
AQ        2.1124148 SEC
RG                362
DW         60.800 USEC
DE          6.00 USEC
TE            295.4 K
D1      2.00000000 SEC
TD0                 1

======= CHANNEL F1 =======
NUC1               1H
P1         10.25 USEC
PL1           -2.00 dB
SPOF1   400.2324716 MHz

F2 - PROCESSING PARAMETERS
SI              32768
SF      400.2300000 MHz
WDW                EM
SSB                 0
LB            0.30 Hz
GB                  0
PC               0.50

FIG.15 (CONTINUED)

CURRENT DATA PARAMETERS

NAME - GF715523-7216376
EXPNO                2
PROCNO               1

P2 - ACQUISITION PARAMETERS
DATE_       20071220
TIME           14.34
INSTRUM        SPECT
PROBHD   5 MM BBO BB-1H
PULPROG        Zgpg30
TD              32768
SOLVENT          DMSO
NS                701
DS                  2
SWH        24154.590 Hz
FIDRES      0.737140 Hz
AQ         0.6783476 SEC
RG              1024
DW           20.700 USEC
DE            6.00 USEC
TE            296.4 K
D1        2.00000000 SEC
D11       0.03000000 SEC
DELTA     1.89999998 SEC
TD0                 1

======== CHANNEL F1 ========
NUC1              13C
P1            9.30 USEC
PL1           -1.00 dB
SPOF1     100.6479773 MHz

======== CHANNEL F2 ========
CPDPRG2        waltz16
NUC2               1H
PCPD2        80.00 USEC
PL2           -2.00 dB
PL12          15.00 dB
PL13          15.00 dB
SFO2      400.2316009 MHz F2 - PROCESSING PARAMETERS
SI             32768
SF        100.6379554 MHz
WDW               EM
SSB                0
LB            1.00 Hz
GB                 0
PC              1.40

FIG.16 (CONTINUED)

CURRENT DATA PARAMETERS

NAME - GF807711-811825
EXPNO                1
PROCNO               1

P2 - ACQUISITION PARAMETERS
DATE_        20080604
TIME           10.34
INSTRUM         SPECT
PROBHD   5 MM DUL 13C-1
PULPROG          Zg30
TD              33852
SOLVENT          DMSO
NS                  8
DS                  2
SWH         8012.820 Hz
FIDRES      0.236702 Hz
AQ          2.1124148 SEC
RG              812.7
DW           62.400 USEC
DE            6.00 USEC
TE              297.5 K
D1       2.00000000 SEC
TD0                 1

======= CHANNEL F1 =======
NUC1               1H
P1           13.70 USEC
PL1             0.00 dB
SPOF1     400.2324714 MHz

F2 - PROCESSING PARAMETERS
SI              32768
SF        400.2300022 MHz
WDW                EM
SSB                 0
LB             0.30 Hz
GB                  0
PC               1.00

FIG.17 (CONTINUED)

CURRENT DATA PARAMETERS

NAME - GF80771-8109241
EXPNO    2
PROCNO    1

P2 - ACQUISITION PARAMETERS
DATE_   20080530
TIME_    15.39
INSTRUM   SPECT
PROBHD 5 MM PABBO BB-
PULPROG   Zgpg30
TD     32768
SOLVENT   DMSO
NS     361
DS     4
SWH   29761.904 Hz
FIDRES   0.908261 Hz
AQ   0.5505524 SEC
RG     362
DW    16.800 USEC
DE    6.00 USEC
TE     296.9 K
D1   2.00000000 SEC
D11   0.03000000 SEC
DELTA  1.89999998 SEC
TD0     1

======= CHANNEL F1 =======
NUC1    13C
P1    11.00 USEC
PL1    0.00 dB
SFOF1  100.6298721 MHz

======= CHANNEL F2 =======
CPDPRG2   waltz16
NUC2    1H
PCPD2   80.00 USEC
PL12    14.78 dB
PL13    14.78 dB
PL2    -1.00 dB
SFO2  400.1516006 MHz F2 - PROCESSING PARAMETERS
SI     32768
SF   100.6177980 MHz
WDW    EM
SSB     0
LB     1.00 Hz
GB     0
PC     1.40

FIG.18 (CONTINUED)

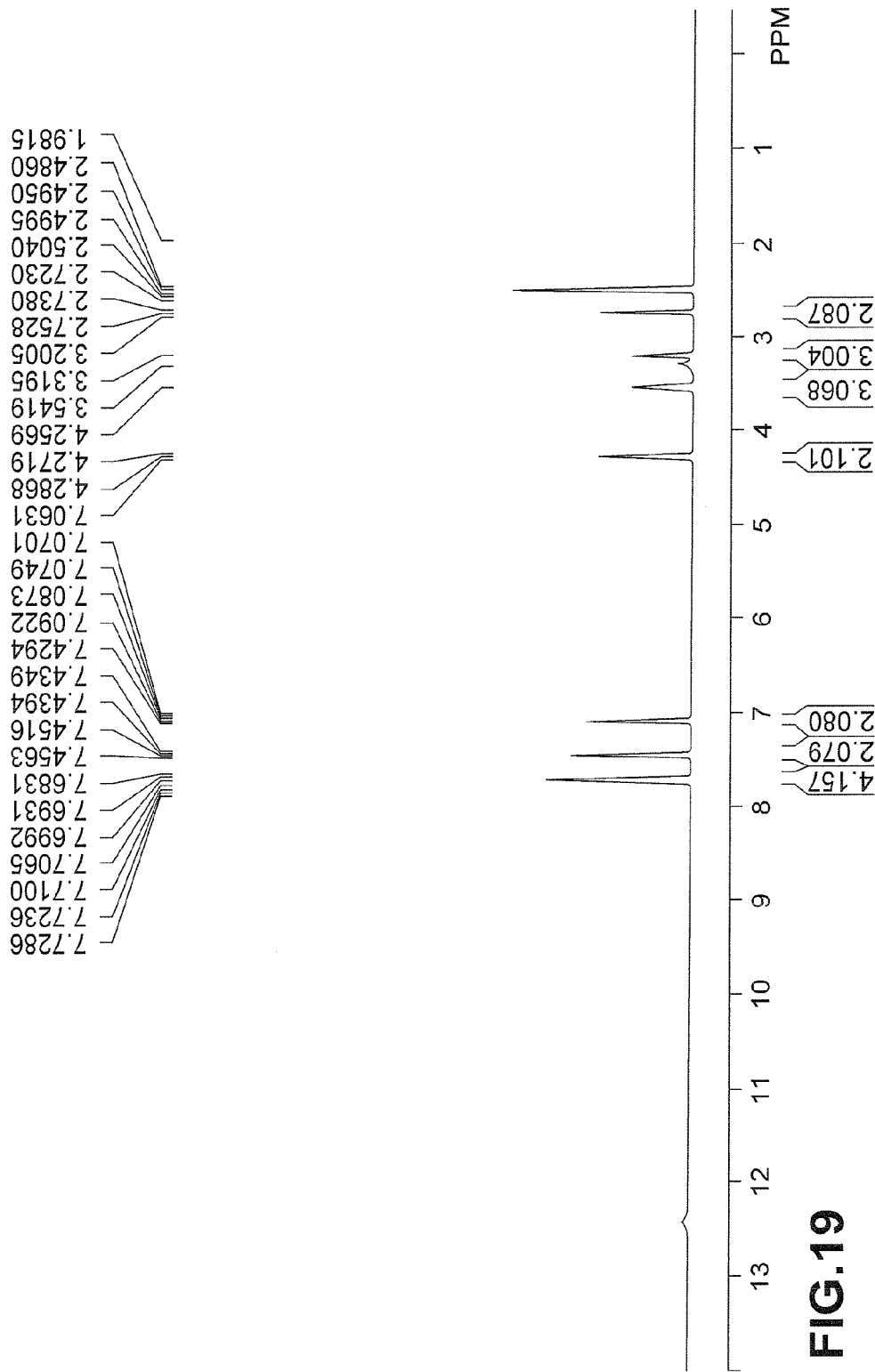
FIG.19 1H-NMR SPECTRUM OF THE COMPOUND OF PREPARATION 2

CURRENT DATA PARAMETERS

NAME - GF820235-8104592
EXPNO                    1
PROCNO                   1

P2 - ACQUISITION PARAMETERS
DATE_         20080524
TIME          14.38
INSTRUM       SPECT
PROBHD   5 MM DUL 13C-1
PULPROG       Zg30
TD            33852
SOLVENT       DMSO
NS            8
DS            2
SWH           8012.820 Hz
FIDRES        0.236702 Hz
AQ            2.1124148 SEC
RG            574.7
DW            62.400 USEC
DE            6.00 USEC
TE            297.6 K
D1            2.00000000 SEC
TD0           1

======= CHANNEL F1 =======
NUC1          1H
P1            13.70 USEC
PL1           0.00 dB
SPOF1         400.2324714 MHz

F2 - PROCESSING PARAMETERS
SI            32768
SF            400.2300000 MHz
WDW           EM
SSB           0
LB            0.30 Hz
GB            0
PC            1.00

FIG.19 (CONTINUED)

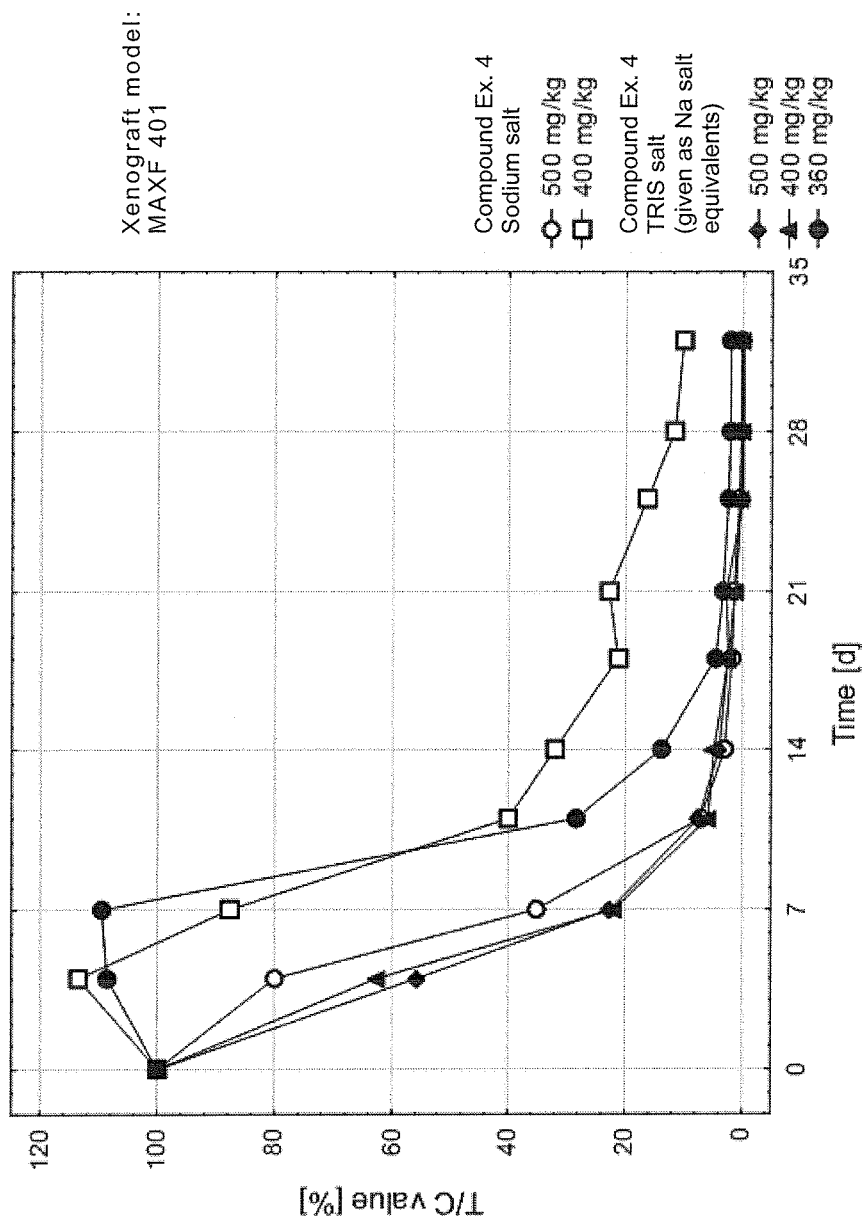
Figure 20: Tumour remission in breast tumours (MAXF 401) in a comparison of the sodium salt and the corresponding TRIS salt of the compound of Example 4

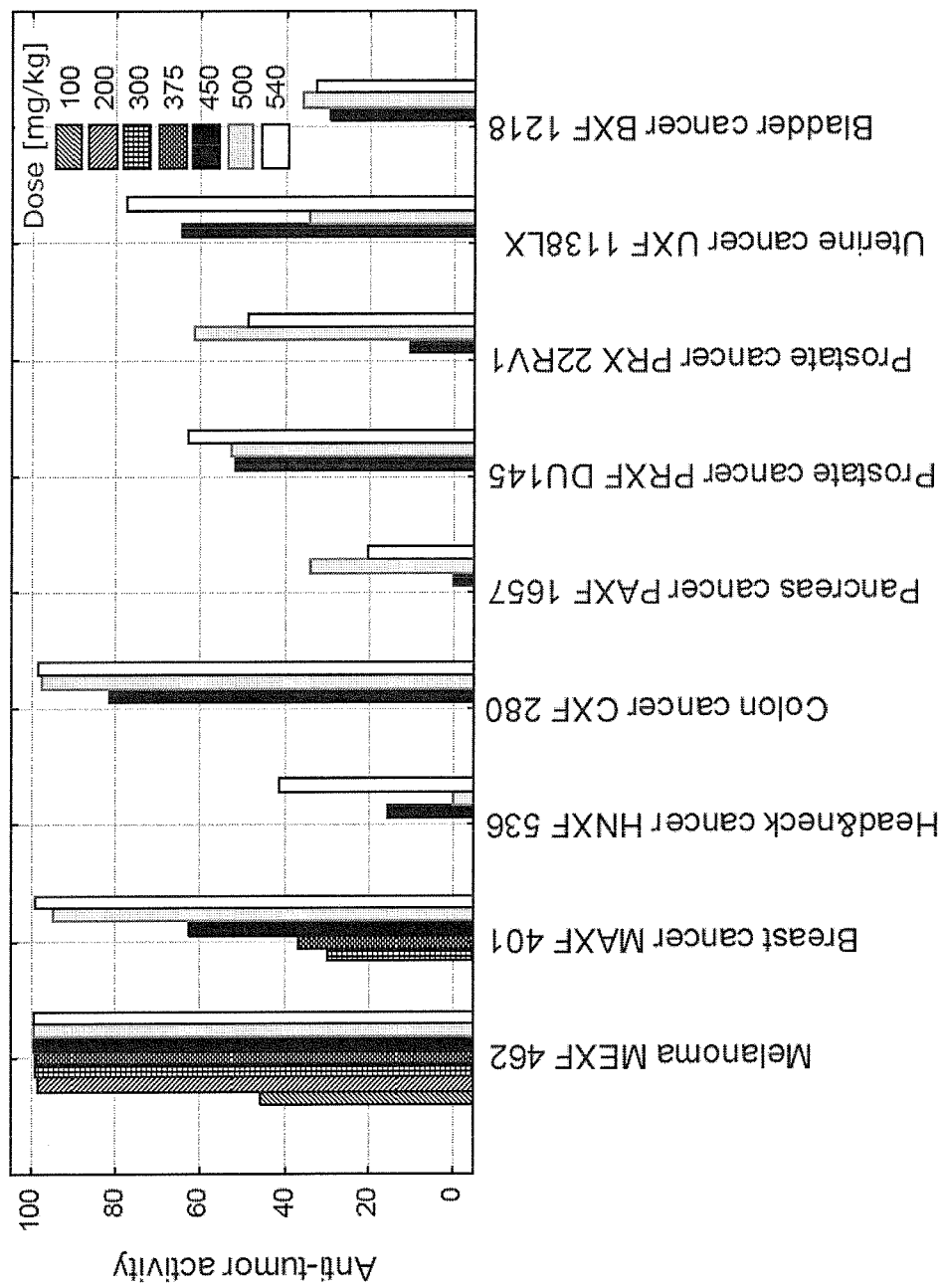
Figure 21: Selectivity of the anti-tumour activity of the compound of Example 2a in different tumours.

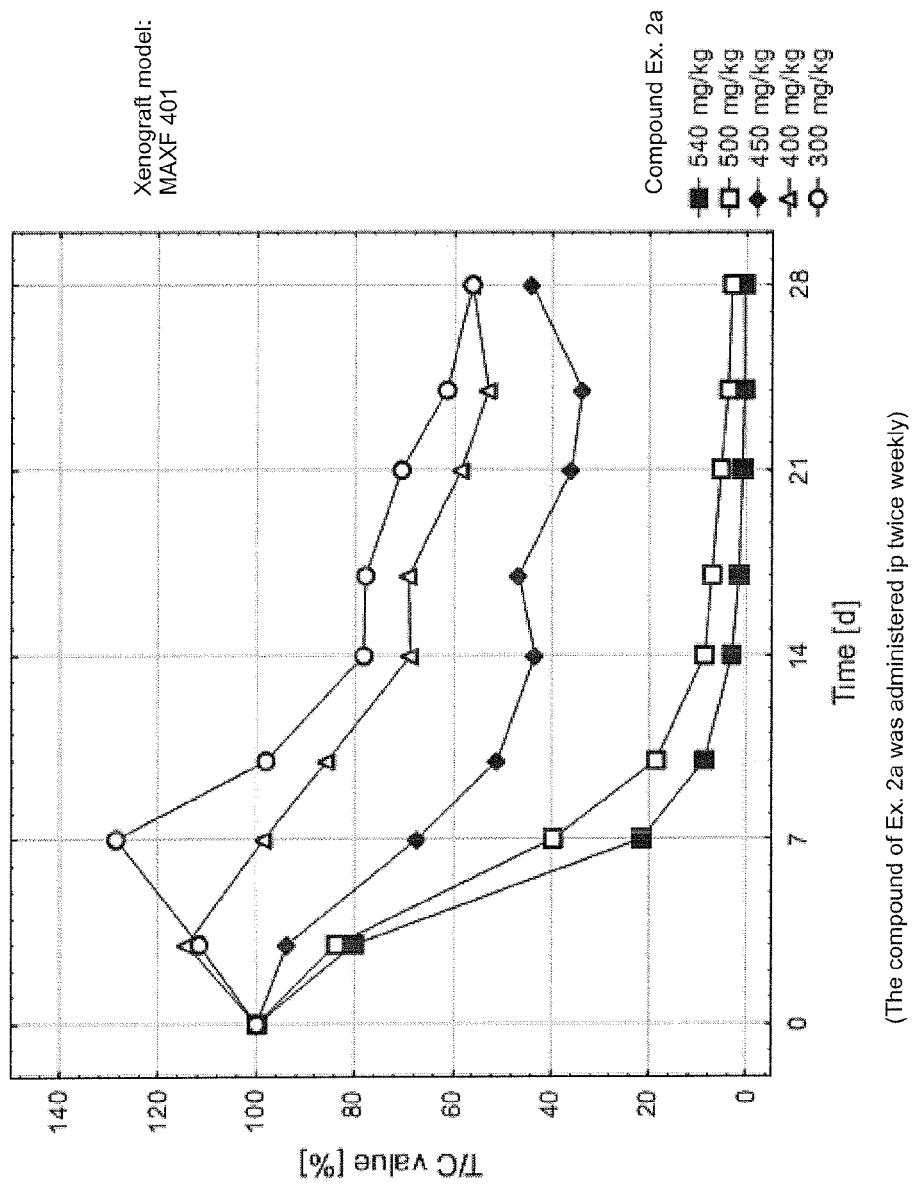
Figure 22: Dose dependency of the anti-tumour action of the compound of Example 2a in breast tumours (MAXF 401 xenograft in nude mice):

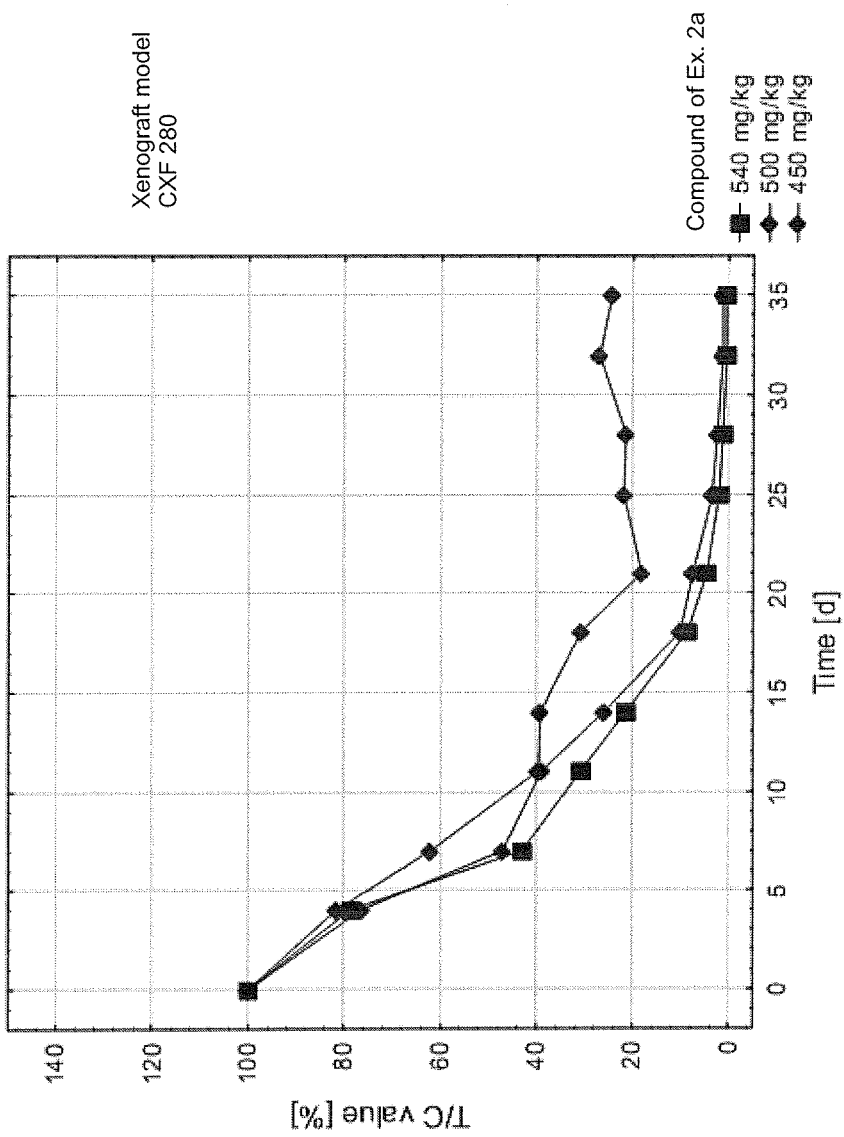
Figure 23: Anti-tumour action of the compound of Example 2a in a colon carcinoma xenograft model.

TRIAZENE COMPOUNDS FOR THE TREATMENT OF CANCER

The present invention relates to novel triazene compounds, to a process for their preparation, to pharmaceutical compositions comprising them, and to the use thereof in the treatment of cancer diseases in humans. The novel triazene compounds are distinguished, as compared with the known triazene compounds, by an improved therapeutic breadth, that is to say by fewer side-effects with a high anti-tumour action.

INTRODUCTION

Triazenes were thoroughly investigated in the 1970s for their cytostatic activity and the resulting possibility of treating cancer diseases. However, because of the considerable side-effects and toxicity of these cytostatics, which belong to the alkylating agents, they never became widely used for combating tumours. One exception is dacarbazin (DTIC), which is a prodrug of monomethyl-triazeno-imidazole-carboxamide (MTIC) and is used mainly for combating melanomas (Montgomery J A (1976) Cancer Treat Rep 60, 205-211).

Because of the sensitivity of dacarbazin to light and in particular because of its side-effects, among which nausea, vomiting and leuko- and thrombo-poenia are to be given special mention, a large number of arylalkyltriazenes have been synthesised with the aim of developing more potent and better tolerated triazenes (Montgomery J A (1976) Cancer treatment reports 60: 125-134; Spassova M K and Golovinsky E V (1985) Pharmac Ther 27: 333-352; Derry E. V. Wilman and Phyllis M. Goddard; J. Med. Chem. 1980. 23, 1052-1024). Despite these efforts, dacarbazin and temozolomid (for the treatment of glioblastomas) have hitherto remained the only triazenes or triazene prodrug in clinical use. THOMAS A. CONNORS, PHYLLIS M. GODDARD, KANTI MERAI, WALTER C. J. ROSS and DERRY E. V. WILMAN; Biochemical Pharmacology, Vol. 25. pp 241-246. Pergamon Press 1976 described the structural requirements for an anti-tumour action. When the triazene-carrying group is an imidazole radical, the compounds are unstable and decompose spontaneously. If the imidazole radical is replaced by different groups, in particular by groups carrying aromatic compounds, the stability of the triazenes increases without changing their activity. However, attempts at developing novel and therapeutically more active triazenes for tumour therapy by means of structure-action relationships have shown that differences in the anti-tumour action did not correlate with the physico-chemical properties of aromatic triazene model compounds. A further difficulty was that alkylating agents having different properties are formed depending on substituents. No improvement in the therapeutic index was found within the tested compounds.

An approach for overcoming the problems of tolerability of selected triazenes has been described in DE 1793 115 and DE 2147 781. By the introduction of strongly polar functional groups it was possible to bring about a considerable improvement not only in the water solubility of triazene derivatives but also in the rapid excretion of the substances. The typical side-effects mentioned above, in particular suppression of the blood-forming system, could be reduced considerably. However, the price of this was a considerable metabolic load on the excretory organs the liver and kidneys. Because of tolerability problems on long-term administration, the tolerable dose range was limiting, so that the highly promising therapeutic potential of this class of compound could not be put into practice. Because such triazenes possess relatively high cytostatic activity, however, they would nevertheless be valuable for combating tumours provided that the mentioned side-effects could be reduced or even eliminated.

Further documents relating to triazenes, which are mentioned here for the sake of completeness, are the following: DE 1768720, WO91/17753 and WO2004/106258 A1 (which likewise relate to the use of triazene derivatives in the treatment of tumours), EP-A-0627325 (which relates to the use of triazenes as dyes), EP-A-0037948 and EP-A-0 071 901 (which relate to processes for the preparation of triazenyl compounds), and F. Schmidt et al.; J. Med. Chem. 1994, 37, 3812-3818 (which relates to the antineoplastic action of peptide-bonded 1,3-dialkyl-3-acyltriazenes).

OBJECT

Accordingly, the object of the present invention was to find cytostatic triazene derivatives having reduced toxicity and improved activity, in order to make them available for therapy in humans, in particular for the therapy of cancer diseases in humans.

BRIEF DESCRIPTION OF THE DRAWINGS

FIG. 19 shows the 1H-NMR spectrum of the product of Preparation 2.

FIG. 20 shows a comparison of the anti-tumour activity of the sodium salt (Example 4a) and the TRIS salt of the compound of Example 4 in the MAXF 401 xenograft model in the nude mouse.

FIG. 21 shows the selectivity of the anti-tumour activity of the substance of Example 2a (sodium salt) on different tumours.

FIG. 22 shows the dose dependency of the anti-tumour action of the substance of Example 2a in breast tumours (MAXF 401-xenograft in nude mice).

FIG. 23 shows the anti-tumour action of the substance of Example 2a (sodium salt) in a colon carcinoma xenograft model.

DESCRIPTION OF THE INVENTION

Figure 1:
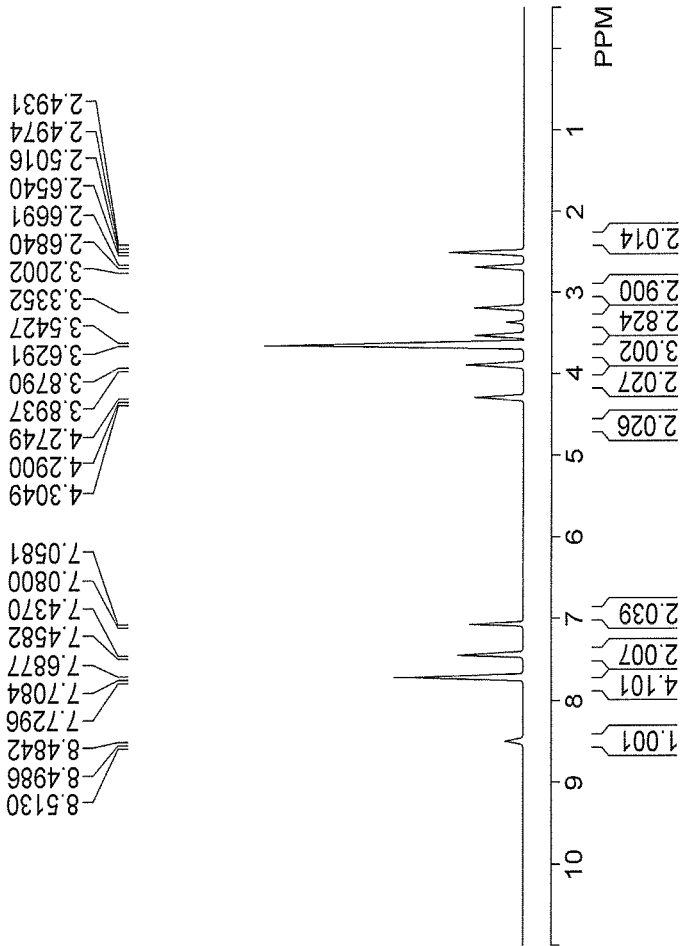
FIG. 1 shows the $^1$H-NMR spectrum (400 MHz) of the compound of Example 1.

The inventors have found novel triazenyl compounds having high cytostatic activity and the toxicity of which is markedly reduced. The invention accordingly provides compounds of formula (1):

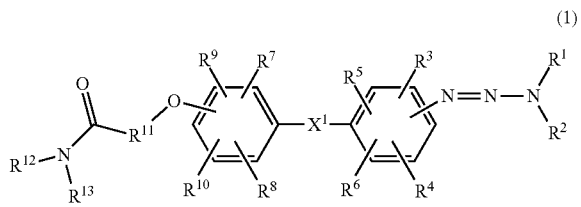

(1)

wherein
$R^1$ and $R^2$ are identical or different and are in each case selected from the group consisting of:
   optionally substituted alkyl,
   optionally substituted alkenyl,
   optionally substituted aryl,
   optionally substituted alkylaryl;
$R^3$, $R^4$, $R^5$, $R^6$, $R^7$, $R^8$, $R^9$ and $R^{10}$ are identical or different and are in each case selected from the group consisting of:
   hydrogen,
   halogen,
   cyano,
   nitro,
   carboxyl,
   aminocarbonyl,
   sulfonic acid radical (—$SO_3H$),
   aminosulfonyl,
   optionally substituted alkyl,
   optionally substituted alkoxy,
   optionally substituted alkenyl,
   optionally substituted aryl,
   optionally substituted alkylaryl;
$R^{11}$ is optionally substituted alkanediyl or optionally substituted alkenediyl;
$R^{12}$ is hydrogen and $R^{13}$ is optionally substituted alkyl or hydroxy, or
$R^{13}$ is hydrogen and $R^{12}$ is optionally substituted alkyl or hydroxy, or
$R^{12}$ and $R^{13}$ are each alkyl, wherein at least one of the alkyl groups has at least one substituent, or
$R^{12}$ and $R^{13}$, together with the nitrogen atom to which they are bonded, form a saturated or unsaturated, optionally substituted 5- to 8-membered ring which can optionally contain further heteroatoms; and
$X^1$ is selected from the group consisting of:
   a single bond,
   carbonyl,
   sulfur,
   oxygen,
   sulfoxy,
   sulfonyl,
   azo and
   an optionally substituted, saturated or unsaturated aliphatic divalent radical having from 1 to 6 carbon atoms,
or pharmaceutically acceptable salts thereof.

In the general formula (1), $R^1$ and $R^2$ are identical or different and are in each case selected from the group consisting of:
   optionally substituted alkyl,
   optionally substituted alkenyl,
   optionally substituted aryl and
   optionally substituted alkylaryl.

Within the scope of the invention as a whole, i.e. also in connection with the other groups of substituents (wherein further possibilities can be included where indicated, as in the case of $R^{12}$ and $R^{13}$), optionally substituted alkyl preferably includes:

Straight-chained or branched alkyl having from 1 to 8, preferably from 1 to 6, carbon atoms, cycloalkyl having from 3 to 8, preferably 5 or 6, carbon atoms, or alkyl having from 1 to 4 carbon atoms which is substituted by cycloalkyl, which in each case can optionally carry preferably from 1 to 3 substituents which are preferably selected from the group consisting of: hydroxy, halogen and cyano. Here and within the scope of the present invention, halogen includes fluorine, chlorine, bromine and iodine, preferably fluorine or chlorine. Furthermore, one or more, more preferably from 1 to 3, carbon atoms can be replaced by heteroanalogous groups containing nitrogen, oxygen or sulfur. This means in particular that, for example, one or more methylene groups in the alkyl radicals can be replaced by NH, O or S.

Examples of alkyl radicals having from 1 to 8 carbon atoms include: a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, a 2-methylbutyl group, an n-hexyl group, a 1-methylpentyl group, a 2-methylpentyl group, a 3-methylpentyl group, a 4-methylpentyl group, a 1-ethylbutyl group, a 2-ethylbutyl group, a 3-ethyl-butyl group, a 1,1-dimethylbutyl group, a 2,2-dimethylbutyl group, a 3,3-dimethylbutyl group, a 1-ethyl-1-methylpropyl group, an n-heptyl group, a 1-methylhexyl group, a 2-methyl-hexyl group, a 3-methylhexyl group, a 4-methylhexyl group, a 5-methylhexyl group, a 1-ethylpentyl group, a 2-ethylpentyl group, a 3-ethylpentyl group, a 4-ethylpentyl group, a 1,1-dimethylpentyl group, a 2,2-dimethylpentyl group, a 3,3-dimethylpentyl group, a 4,4-dimethylpentyl group, a 1-propyl-butyl group, an n-octyl group, a 1-methylheptyl group, a 2-methylheptyl group, a 3-methylheptyl group, a 4-methylheptyl group, a 5-methylheptyl group, a 6-methylheptyl group, a 1-ethylhexyl group, a 2-ethylhexyl group, a 3-ethylhexyl group, a 4-ethylhexyl group, a 5-ethylhexyl group, a 1,1-dimethylhexyl group, a 2,2-dimethylhexyl group, a 3,3-dimethylhexyl group, a 4,4-dimethylhexyl group, a 5,5-dimethylhexyl group, a 1-propylpentyl group, a 2-propylpentyl group, etc. Preference is given to those having from 1 to 6 carbon atoms, in particular methyl, ethyl and n-propyl. Methyl is most preferred.

Examples of alkyl groups which are formed by replacement with one or more heteroanalogous groups, such as —O—, —S— or —NH—, are preferably those in which one or more methylene groups have been replaced by —O— to form an ether group, such as methoxymethyl, ethoxymethyl, 2-methoxyethylene, etc. According to the invention, polyether groups are also included in the definition of alkyl.

Cycloalkyl radicals having from 3 to 8 carbon atoms preferably include: a cyclopropyl group, a cyclobutyl group, a cyclopentyl group, a cyclohexyl group, a cycloheptyl group, a cyclooctyl group, etc. Preference is given to a cyclopropyl group, a cyclobutyl group, a cyclopentyl group and a cyclohexyl group. Heterocyclic alkyl radicals which are formed from cycloalkyl by replacement of methylene by heteroanalogous groups are, for example, 5- or 6-membered heterocyclic radicals, such as tetrahydrofuryl, pyrrolidinyl, piperidinyl or tetrahydropyranyl, which can optionally be fused with aromatic rings, etc.

Examples of a halo-substituted linear or branched alkyl radical having from 1 to 8 carbon atoms include in particular: a fluoromethyl group, a difluoromethyl group, a trifluoromethyl group, a chloromethyl group, a dichloromethyl group, a trichloromethyl group, a bromomethyl group, a dibromomethyl group, a tribromomethyl group, a 1-fluoroethyl group, a 1-chloroethyl group, a 1-bromoethyl group, a 2-fluoroethyl group, a 2-chloroethyl group, a 2-bromoethyl group, a 1,2-difluoroethyl group, a 1,2-dichloroethyl group, a 1,2-dibromo-ethyl group, a 2,2,2-trifluoroethyl group, a heptafluoroethyl group, a 1-fluoropropyl group, a 1-chloropropyl group, a 1-bromopropyl group, a 2-fluoropropyl group, a 2-chloropropyl group, a 2-bromopropyl group, a 3-fluoropropyl group, a 3-chloropropyl group, a 3-bromopropyl group, a 1,2-difluoropropyl group, a 1,2-dichloropropyl group, a 1,2-dibromopropyl group, a 2,3-difluoropropyl group, a 2,3-dichloropropyl group, a 2,3-dibromopropyl group, a 3,3,3-trifluoropropyl group, a 2,2,3,3,3-pentafluoropropyl group, a 2-fluorobutyl group, a 2-chlorobutyl group, a 2-bromobutyl group, a 4-fluorobutyl group, a 4-chlorobutyl group, a 4-bromobutyl group, a 4,4,4-trifluorobutyl group, a 2,2,3,3,4,4,4-heptafluorobutyl group, a perfluorobutyl group, a 2-fluoropentyl group, a 2-chloropentyl group, a 2-bromopentyl group, a 5-fluoropentyl group, a 5-chloropentyl group, a 5-bromopentyl group, a perfluoropentyl group, a 2-fluorohexyl group, a 2-chlorohexyl group, a 2-bromohexyl group, a 6-fluorohexyl group, a 6-chlorohexyl group, a 6-bromohexyl group, a perfluorohexyl group, a 2-fluoroheptyl group, a 2-chloroheptyl group, a 2-bromoheptyl group, a 7-fluoroheptyl group, a 7-chloroheptyl group, a 7-bromoheptyl group, a perfluoroheptyl group, etc.

Examples of a hydroxy-substituted alkyl radical include the above-mentioned alkyl radicals with from 1 to 3 hydroxy radicals, such as, for example, hydroxymethyl, 2-hydroxyethyl, 3-hydroxypropyl, etc.

Within the scope of the invention as a whole, optionally substituted alkenyl preferably includes:

Straight-chained or branched-chained alkenyl having from 2 to 8 carbon atoms and cycloalkenyl having from 3 to 8 carbon atoms, which can optionally be substituted by preferably from 1 to 3 substituents, such as hydroxy, halogen or alkoxy. Examples include: vinyl, 1-methylvinyl, allyl, 1-butenyl, isopropenyl, cyclopropenyl, cyclobutenyl, cyclopentenyl, cyclohexenyl. Vinyl or allyl are preferred.

Within the scope of the invention as a whole, optionally substituted aryl preferably includes:

Aromatic hydrocarbon radicals having from 6 to 14 carbon atoms (wherein the carbon atoms of the substituents are not included) and 5- to 10-membered aromatic heterocyclic radicals having up to 3 heteroatoms from the group S, O, N, which can be mono- or bi-cyclic and which can be substituted by preferably from 1 to 3 substituents selected from hydroxy, halogen, cyano, alkyl, acyl and alkoxy. With regard to the definition of alkyl and halogen, reference may be made to the definitions and examples hereinbefore.

Here and in the following, alkoxy as a substituent of aryl includes, for example: An alkyl radical mentioned hereinbefore which is bonded to aryl via an oxygen atom, such as a linear or branched alkoxy radical having up to 6 carbon atoms, such as a methoxy group, an ethoxy group, an n-propoxy group, an isopropoxy group, an n-butoxy group, an isobutoxy group, a sec-butoxy group, a tert-butoxy group, an n-pentoxy group, an isopentoxy group, a sec-pentoxy group, a tert-pentoxy group, a 2-methylbutoxy group, an n-hexyloxy group, an isohexyloxy group, a tert-hexyloxy group, a sec-hexyloxy group, a 2-methylpentoxy group, a 3-methylpentoxy group, a 1-ethylbutoxy group, a 2-ethylbutoxy group, a 1,1-dimethylbutoxy group, a 2,2-dimethylbutoxy group, a 3,3-dimethylbutoxy group, a 1-ethyl-1-methylpropoxy group, etc. Preference is given to a methoxy group, an ethoxy group, an n-propoxy group, an isopropoxy group, an n-butoxy group, an isobutoxy group, a sec-butoxy group, a tert-butoxy group, etc.

Here and in the following, acyl as a substituent of aryl includes: aliphatic acyl, aromatic acyl, such as C1 to C6 alkanoyl, such as formyl, acetyl, propionyl, butyryl, isobutyryl, valeryl, isovaleryl, pivaloyl, hexanoyl, etc., and also C6 to C10 aroyl, such as benzoyl, toluolyl, xyloyl, etc.

Aromatic hydrocarbon radicals having from 6 to 14 carbon atoms include, for example: phenyl, naphthyl, phenanthrenyl and anthracenyl, which can optionally be substituted. Phenyl is preferred.

Heteroaromatic radicals include, for example: pyridyl, pyridyl N-oxide, pyrimidyl, pyridazinyl, pyrazinyl, thienyl, furyl, pyrrolyl, pyrazolyl, imidazolyl, thiazolyl, oxazolyl or isoxazolyl, indolizinyl, indolyl, benzo(b)thienyl, benzo(b)-furyl, indazolyl, quinolyl, isoquinolyl, naphthyridinyl, quinazolinyl. Preference is given to 5- or 6-membered aromatic heterocycles such as, for example, pyridyl, pyridyl N-oxide, pyrimidyl, pyridazinyl, furyl and thienyl.

Within the scope of the invention as a whole, optionally substituted alkylaryl preferably includes:

Straight-chained or branched alkyl having from 1 to 8, preferably from 1 to 4, carbon atoms, as described above, which is substituted with aryl, as described above. The preferred arylalkyl is benzyl.

Particularly preferably, $R^1$ and $R^2$ are in each case alkyl and are preferably identical (preferred) or different and in each case straight-chained or branched alkyl having from 1 to 6, preferably from 1 to 4, more preferably from 1 to 3, carbon atoms, preference being given to linear alkyl. $R^1$ and $R^2$ are preferably methyl or ethyl. $R^1$ and $R^2$ are most preferably methyl.

In the general formula (1), $R^3$, $R^4$, $R^5$, $R^6$, $R^7$, $R^8$, $R^9$ and $R^{10}$ are identical or different and are in each case selected from the group consisting of:

hydrogen,
halogen,
cyano,
nitro,
carboxyl,
aminocarbonyl,
sulfonic acid (—$SO_3H$),
aminosulfonyl,
optionally substituted alkyl,
optionally substituted alkoxy,
optionally substituted alkenyl,
optionally substituted aryl,
optionally substituted alkylaryl.

With regard to the definition of said substituents and their preferred meanings, reference may be made to the comments made above in respect of the corresponding substituents in connection with the definition of $R^1$ and $R^2$. In addition, within the scope of the invention as a whole, aminocarbonyl preferably represents carbamoyl ($H_2NCO$—) or mono- or di-alkylaminocarbonyl (H(alkyl)NCO— or (alkyl)$_2$NCO—), wherein, with regard to the definition of alkyl, reference may be made to the comments made above and optionally substituted alkyl is also included. Furthermore, aminosulfonyl within the scope of the invention as a whole represents in particular sulfamoyl ($H_2N$—$SO_2$—) or mono- or di-alkylaminosulfonyl(alkyl)$_2$N—$SO_2$, wherein, with regard to the definition of alkyl, reference may be made to the comments made above and optionally substituted alkyl is also included. Optionally substituted alkoxy includes alkoxy as exemplified above as a substituent of aryl, which can optionally be substituted by preferably from 1 to 3 substituents which are preferably selected from the group halogen, hydroxy and cyano.

Preferably, $R^3$, $R^4$, $R^5$, $R^6$, $R^7$, $R^8$, $R^9$ and $R^{10}$ are selected from:
hydrogen,
halogen,
cyano,
nitro,
carboxyl,
aminocarbonyl,
sulfonic acid (—$SO_3H$),
aminosulfonyl,
optionally substituted alkyl and
optionally substituted alkoxy.

More preferably, $R^3$, $R^4$, $R^5$, $R^6$, $R^7$, $R^8$, $R^9$ and $R^{10}$ are selected from:
hydrogen,
halogen and
optionally substituted alkoxy.

Preferably at least 6, more preferably at least 7, of the radicals $R^3$, $R^4$, $R^5$, $R^6$, $R^7$, $R^8$, $R^9$ and $R^{10}$ represent hydrogen. Most preferably, all the radicals $R^3$, $R^4$, $R^5$, $R^6$, $R^7$, $R^8$, $R^9$, and $R^{10}$ represent hydrogen.

$R^{11}$ in the general formula (1) is optionally substituted alkanediyl or optionally substituted alkenediyl. Optionally substituted alkanediyl is preferably a divalent straight-chained or branched alkanediyl radical having from 1 to 7, preferably from 1 to 6, more preferably from 1 to 4, carbon atoms, which can optionally carry from 1 to 3 substituents selected from the group consisting of hydroxy, halogen and cyano. The following may be mentioned as preferred examples: methylene, 1,2-ethanediyl, ethane-1,1-diyl, 1,3-propylene, propane-1,1-diyl, propane-1,2-diyl, propane-2,2-diyl, 1,4-butylene, butane-1,2-diyl, butane-1,3-diyl, butane-2,3-diyl, pentane-1,5-diyl, pentane-2,4-diyl, 3-methylpentane-2,4-diyl and hexane-1,6-diyl. A preferred substituted alkanediyl radical is a hydroxy-substituted alkanediyl radical. Optionally substituted alkenediyl is preferably a divalent straight-chained or branched alkenediyl radical having from 2 to 7, more preferably from 2 to 6, still more preferably from 2 to 4, carbon atoms, which can optionally carry from 1 to 3 substituents selected from the group consisting of hydroxy, halogen and cyano. The following may be mentioned as preferred examples: ethene-1,1-diyl, ethene-1,2-diyl, propene-1,1-diyl, propene-1,2-diyl, propene-1,3-diyl, but-1-ene-1,4-diyl, but-1-ene-1,3-diyl, but-2-ene-1,4-diyl, buta-1,3-diene-1,4-diyl, pent-2-ene-1,5-diyl, hex-3-ene-1,6-diyl and hexa-2,4-diene-1,6-diyl.

Within the scope of the present invention, $R^{11}$ is particularly preferably alkanediyl, more preferably alkanediyl having from 1 to 3 carbon atoms, still more preferably 1,2-ethanediyl (—$CH_2CH_2$—) or 1,3-propanediyl (—$CH_2CH_2CH_2$—). $R^{11}$ is most preferably 1,2-ethanediyl (—$CH_2CH_2$—).

In the general formula (1), $X^1$ is selected from the group consisting of:
a single bond,
carbonyl (—CO—),
sulfur (—S—),
oxygen (—O—),
sulfoxy (—SO—),
sulfonyl (—$SO_2$—),
azo (—N=N—) and
an optionally substituted, saturated or unsaturated aliphatic radical having from 1 to 6 carbon atoms.

Within the scope of the present invention, an optionally substituted, saturated or unsaturated aliphatic radical having from 1 to 6 carbon atoms for $X^1$ includes: optionally substituted alkanediyl as defined above, optionally substituted alkenediyl as defined above, and alkynediyl. $X^1$ is preferably alkanediyl, alkenediyl or alkynediyl having up to 4, having up to 2 carbon atoms, such as methylene (—$CH_2$—), which can optionally be substituted by hydroxyl (such as, for example, —CH(OH)—).

Compounds of the general formula (1) in which $X^1$ is carbonyl (—CO—) are most preferred.

Within the scope of the present invention, the groups $R^{12}$ and $R^{13}$ in the general formula (1) are selected from the following alternatives:
1) $R^{12}$ is hydrogen and $R^{13}$ is optionally substituted alkyl or hydroxyl, or
   $R^{13}$ is hydrogen and $R^{12}$ is optionally substituted alkyl or hydroxyl.

The alternatives mentioned under 1) are equivalent. They correspond to the case in which one substituent of $R^{12}$ or $R^{13}$ is hydrogen and the other substituent is optionally substituted alkyl or hydroxyl.

2) $R^{12}$ and $R^{13}$ are each alkyl, wherein at least one of the alkyl groups has at least one substituent, that is to say $R^{12}$ and $R^{13}$ are substituted alkyl, or
3) $R^{12}$ and $R^{13}$, together with the nitrogen atom to which they are bonded, form a saturated or unsaturated, optionally substituted 5- to 8-membered ring which can optionally contain further heteroatoms.

Alternative 1):
Alternative 1) mentioned hereinbefore is a preferred alternative within the scope of the present invention. More preferably, within the scope of this alternative:
$R^{12}$ is hydrogen and $R^{13}$ is substituted alkyl, or
$R^{13}$ is hydrogen and $R^{12}$ is substituted alkyl.

Alkyl here includes straight-chained or branched alkyl having from 1 to 8, preferably from 1 to 6, carbon atoms, cycloalkyl having from 3 to 8, preferably 5 or 6, carbon atoms, or alkyl having from 1 to 4 carbon atoms which is substituted by cycloalkyl. With regard to possible examples of alkyl, reference may be made to the examples mentioned above for $R^1$ and $R^2$. Particularly preferably, alkyl is here a C1 to C6, preferably C1 to C5, alkyl group which can be branched or straight-chained, such as in particular methyl, ethyl, propyl, 2-methylpropane, butyl, such as n-butyl, 2-methylbutyl, 3-methylbutyl, pentyl, such as n-pentyl, or n-hexyl. Said alkyl groups are substituted by at least one substituent. Preferred substituents of alkyl are polar functional groups containing one or more heteroatoms, which are preferably selected from: N, O, S, halogen, such as Cl, F, Br and I. In the definition of $R^{12}$ and $R^{13}$, substituents of alkyl include in particular:

A group of the formula:

—$X^2$—$R^{14}$, wherein $X^2$ is selected from the group consisting of:
 carbonyl,
 sulfoxy and
 sulfonyl, and
$R^{14}$ is selected from the group consisting of:
 hydroxy,
 optionally substituted amino and
 optionally substituted alkoxy.

Preferably, $X^2$ is carbonyl and $R^{14}$ is hydroxy.

When $R^{14}$ is hydroxy, the substituent group —$X^2R^{14}$ is carboxy. When $R^{14}$ is optionally substituted amino, the substituent group —$X^2R^{14}$ is, for example, —$CONH_2$, that is to say carbamoyl in the case of $R^{14}$=amino, or —$X^2R^{14}$ mono- or di-alkylaminocarbonyl in the case of $R^{14}$=alkylamino or dialkylamino. When $R^{14}$ is optionally substituted alkoxy, the substituent group —$X^2R^{14}$ is, for example, alkoxycarbonyl in the case of $R^{14}$=alkoxy, that is to say an ester group. Substituents of alkyl in the definition of $R^{12}$ and $R^{13}$ preferably contain at least one group, preferably one or two groups, of the formula —$X^2R^{14}$.

In addition to the group —$X^2R^{14}$ that is preferably present, further preferred substituents of alkyl in the definition of $R^{12}$ and $R^{13}$ include the following substituents:
 guanidino,
 thiol (—SH),
 alkylthio, such as in particular methylthio,
 amino (—$NH_2$),
 mono- or di-alkylamino,
 acylamino, wherein acyl is in particular as defined above,
 saturated, unsaturated or aromatic, mono- or bi-cyclic, optionally substituted heterocyclic radicals, such as, for example, the optionally substituted heteroaromatic radicals mentioned hereinbefore, preferably imidazolyl, such as imidazol-5-yl, 1H-indolyl, such as 1H-indol-3-yl,
 optionally substituted aryl, as described above, in particular phenyl, hydroxyphenyl, such as 4-hydroxy-phenyl, alkoxyphenyl, such as methoxyphenyl,
 hydroxyl,
 alkoxy, as described hereinbefore.

Alkyl in the definition of $R^{12}$ and $R^{13}$ preferably has one or two substituents, of which preferably at least one substituent is the group —$X^2R^{14}$.

In a preferred form of alternative 1) mentioned hereinbefore:
 $R^{12}$ is hydrogen and $R^{13}$ is a radical A of a compound of the formula $H_2$N-A, or
 $R^{13}$ is hydrogen and $R^{12}$ is a radical A of a compound of the formula $H_2$N-A, wherein
A is a radical which is derived formally by cleavage of an amino group (—$NH_2$) from a natural or synthetic amino acid, a natural or synthetic amino acid derivative or a polyamino acid or polyamino acid derivative.

For the purposes of illustration:
If the amino acid $H_2$N-A is, for example, glycine:

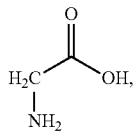

then A=$R^{12}$ or $R^{13}$ is a radical of the formula:

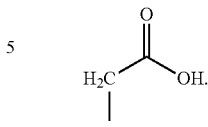

More preferred are compounds according to the invention wherein A is the radical derived formally by cleavage of the amino group from an amino acid or amino acid derivative (for clarification: The formal cleavage of the amino group from an amino acid does not mean the cleavage of an amino group from an amide group ($H_2$N—CO—) that is optionally present but of an amino group bonded to a carbon atom that does not carry further substituents other than H or C. That is to say, the corresponding radical $R^{12}$ or $R^{13}$ formed by cleavage of an amino group from asparagine would be:

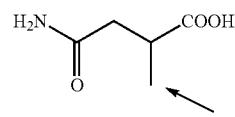

(the arrow denotes the binding site) and not:

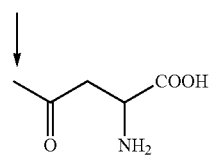

(the arrow denotes the binding site)).

Still more preferably, the radical A is formed from the cleavage of a $H_2$N group from the group of the following amino acids:
 alanine, corresponding to the case where $R^{12}$ or $R^{13}$ is ethyl substituted by carboxy,
 arginine (less preferred), corresponding to the case where $R^{12}$ or $R^{13}$ is butyl substituted by carboxy and guanidino,
 asparagine, corresponding to the case where $R^{12}$ or $R^{13}$ is ethyl substituted by aminocarbonyl (carbamoyl) and carboxy,
 aspartic acid, corresponding to the case where $R^{12}$ or $R^{13}$ is ethyl substituted by two carboxy groups,
 cysteine (less preferred), corresponding to the case where $R^{12}$ or $R^{13}$ is ethyl substituted by thio (—SH) and carboxy,
 glutamine, corresponding to the case where $R^{12}$ or $R^{13}$ is propyl substituted by aminocarbonyl (carbamoyl) and carboxy,
 glutamic acid, corresponding to the case where $R^{12}$ or $R^{13}$ is propyl substituted by two carboxy groups,
 glycine, corresponding to the case where $R^{12}$ or $R^{13}$ is methyl substituted by carboxy,
 histidine, corresponding to the case where $R^{12}$ or $R^{13}$ is ethyl substituted by carboxy and imidazolyl,
 isoleucine, corresponding to the case where $R^{12}$ or $R^{13}$ is 2-methylbutyl substituted by carboxy,
 leucine, corresponding to the case where $R^{12}$ or $R^{13}$ is 3-methylbutyl substituted by carboxy, lysine, corresponding to the case where $R^{12}$ or $R^{13}$ is n-pentyl substituted by carboxy and amino, wherein binding can take place via the amino group adjacent to the carboxyl group:

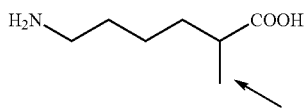

(arrow indicates the bond line or binding site) or via the terminal amino group:

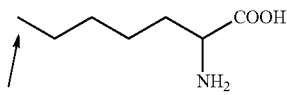

(arrow indicates the bond line or binding site), so that the corresponding compounds of formula (1) look like this:

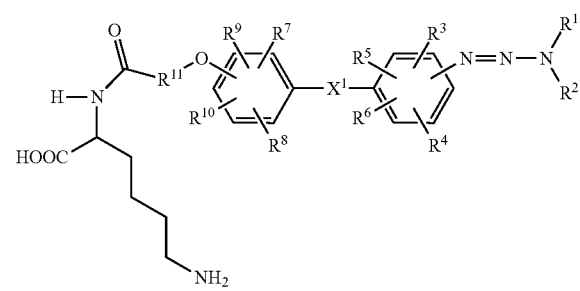

or

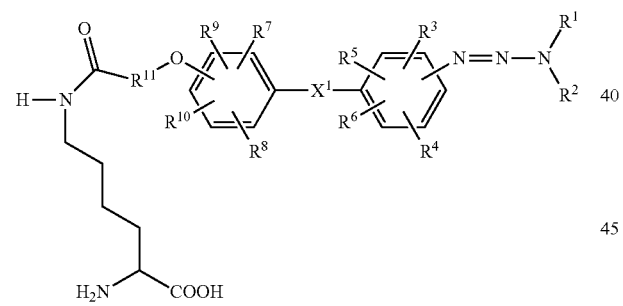

(this applies analogously to other basic amino acids having more than one amino group),
  methionine, corresponding to the case where $R^{12}$ or $R^{13}$ is n-propyl substituted by carboxy and methylthio,
  phenylalanine, corresponding to the case where $R^{12}$ or $R^{13}$ is ethyl substituted by carboxy and phenyl,
  serine, corresponding to the case where $R^{12}$ or $R^{13}$ is ethyl substituted by carboxy and hydroxy,
  threonine, corresponding to the case where $R^{12}$ or $R^{13}$ is n-propyl substituted by carboxy and hydroxy,
  tryptophan, corresponding to the case where $R^{12}$ or $R^{13}$ is ethyl substituted by carboxy and indolyl,
  tyrosine, corresponding to the case where $R^{12}$ or $R^{13}$ is ethyl substituted by carboxy and hydroxyphenyl, and
  valine, corresponding to the case where $R^{12}$ or $R^{13}$ is 2-methylpropyl substituted by carboxy,
or derivatives, such as in particular esters or amides, thereof, corresponding to the case where $R^{14}$ is alkoxy or optionally substituted amino, or derivatives or polyamino acids thereof, which are formed by peptidic linking with one or more further amino acids to the amino acids mentioned hereinbefore or hereinafter.

Further amino acid compounds, or derivatives thereof, from which a radical $R^{12}$ or $R^{13}$ is formed formally by cleavage of an amino group include: creatine (less preferred), creatinine, taurine, or derivatives or polyamino acids thereof, which are formed by peptidic linking with one or more further amino acids to the amino acids mentioned hereinbefore or hereinafter. Also included are so-called non-proteinogenic amino acids, such as, for example: 4-aminobutyric acid (GABA), L-homoserine (2-amino-4-hydroxybutyric acid), ornithine (2,5-diaminovaleric acid), L-(+)-citrulline(N-5-(aminocarbonyl)-L-ornithine), 5-hydroxytryptophan (5-HTP), β-alanine (3-aminopropionic acid), β-methylamino-alanine, D-valine, D-alanine, D-glutamic acid and 2,6-diaminopimelic acid.

The derivatives of the above-mentioned amino acid compounds $H_2N$-A are in particular those which have been formed by replacement of a hydrogen atom by a hydroxyl function.

Very preferred are compounds according to the invention wherein the radical A is derived formally by cleavage of the $H_2N$ group from the group of the amino acids glycine and its derivatives and histidine and its derivatives.

Most preferred are compounds according to the invention wherein the radical A is derived by cleavage of the $H_2N$ group from the group of the following amino acids or amino acid derivatives: glycine:

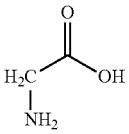

corresponding to $R^{12}$ or $R^{13}$=

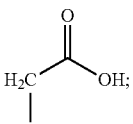

glycineamide:

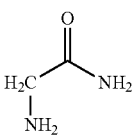

(2-amino-acetamide), corresponding to $R^{12}$ or $R^{13}$=

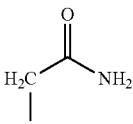

glycine ethyl ester:

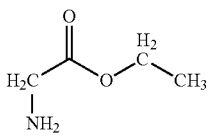

(amino-acetic acid ethyl ester), corresponding to $R^{12}$ or $R^{13}=$

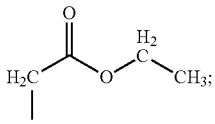

histidine:

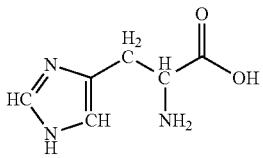

corresponding to $R^{12}$ or $R^{13}=$

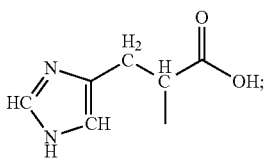

or histidineamide:

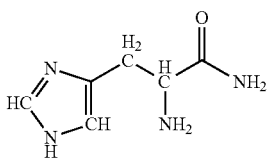

(2-amino-3-(1H-imidazol-4-yl)-propionamide), corresponding to $R^{12}$ or $R^{13}=$

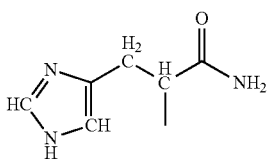

With the exception of glycine, all amino acids contain asymmetric carbon atoms. The compounds according to the invention in which $R^{12}$ or $R^{13}$ is a radical A which is formed formally by cleavage of an amino group from a natural amino acid therefore have the natural configuration (L configuration) of the amino acid. This is also true of compounds that are formed formally by cleavage of an amino group from an amino acid derivative, a polyamino acid and polyamino acid derivatives. According to the invention, however, the case where the amino acids have the non-natural D configuration, such as D-alanine, D-glutamic acid, etc., is also included.

Preference is given according to the invention to compounds wherein the amino acids $H_2N$-A have the L configuration, or wherein $R^{12}$ or $R^{13}$ represents the radical A of such an amino acid, and to those compounds wherein the underlying amino acid derivatives, the polyamino acids and the polyamino acid derivatives are derived from amino acids $H_2N$-A having the L configuration.

In view of their better water solubility, preference is further given to compounds in which the radical $R^{12}$ or $R^{13}$ is formed formally by cleavage of a $NH_2$ group from an acidic amino acid having at least two carboxyl groups, such as aspartic acid, glutamic acid. The use of hydroxyl-group-containing amino acids, such as, for example, threonine, can also be preferred from this point of view.

Alternative 2:

In alternative 2) mentioned hereinbefore, wherein $R^{12}$ and $R^{13}$ are each alkyl, wherein at least one of the alkyl groups has at least one substituent, preferably one or two substituents, reference may be made with regard to the definitions and examples of alkyl to those given above for $R^1$ or $R^2$ or for $R^{12}$ and $R^{13}$ in alternative 1). Substituents of alkyl accordingly include examples given for "optionally substituted alkyl" in the definition of $R^1$ and $R^2$, such as hydroxy, halogen and cyano. In addition, possible substituents of alkyl in alternative 2) also include the examples given for $R^{12}$ and $R^{13}$ in alternative 1) described hereinbefore, such as guanidino,
thiol (—SH),
alkylthio, such as in particular methylthio,
amino (—$NH_2$),
mono- or di-alkylamino,
acylamino, wherein acyl is in particular as defined above,
saturated, unsaturated or aromatic, mono- or bi-cyclic, optionally substituted heterocyclic radicals, such as, for example, the above-mentioned optionally substituted heteroaromatic radicals, preferably imidazolyl, such as imidazol-5-yl, 1H-indolyl, such as 1H-indol-3-yl,
optionally substituted aryl, as described above, in particular phenyl, hydroxyphenyl, such as 4-hydroxy-phenyl, alkoxyphenyl, such as methoxyphenyl,
hydroxy,
alkoxy, as described hereinbefore, and
a group of the formula:

wherein $X^2$ and $R^{14}$ are as defined above, and, in particular, also the radicals which result formally from the cleavage of the $NH_2$ group from the amino acids $NH_2$-A.

Alternative 3):

In alternative 3) mentioned hereinbefore, wherein $R^{12}$ and $R^{13}$, together with the nitrogen atom to which they are bonded, form a saturated or unsaturated, optionally substituted 5- to 8-membered ring which can optionally contain further heteroatoms, possible ring systems consisting of $R^{12}$ and $R^{13}$ and the nitrogen atom to which they are bonded preferably include 5- or 6-membered, optionally substituted rings, such as piperidin-1-yl, morpholin-4-yl, thiomorpholin-4-yl, pyrrolidin-1-yl, oxazolidin-3-yl, thiazolidin-3-yl, 2-carboxyl-pyrrolidin-1-yl (prolyl), 3- or 4-hydroxy-carboxyl-pyrrolidin-1-yl (3- or 4-hydroxy-prolyl), etc. Prolyl and hydroxy-prolyl are particularly preferred.

Triazene compounds that are particularly preferred according to the invention are those wherein $R^1$ and $R^2$ are in each case alkyl, preferably alkyl having from 1 to 6 carbon atoms, particularly preferably methyl.

Triazene compounds that are particularly preferred according to the invention are those wherein $R^3$, $R^4$, $R^5$, $R^6$, $R^7$, $R^8$, $R^9$ and $R^{10}$ are in each case hydrogen.

Triazene compounds that are particularly preferred according to the invention are those wherein $X^1$ is carbonyl.

Triazene compounds that are particularly preferred according to the invention are those wherein $R^{11}$ is alkanediyl, preferably linear alkanediyl having from 1 to 6 carbon atoms, particularly preferably methylene (—$CH_2$—) or ethane-1,2-diyl.

Triazene compounds that are particularly preferred according to the invention are those wherein the radicals $X^1$ and the radical

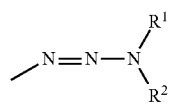

on the phenylene radical are in the para-position relative to one another.

Triazene compounds that are particularly preferred according to the invention are those wherein the radicals $X^1$ and the radical

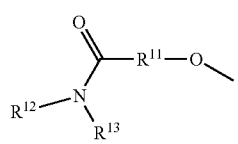

on the phenylene radical are in the para-position relative to one another.

Particular preference is given according to the invention to compounds of formula (2):

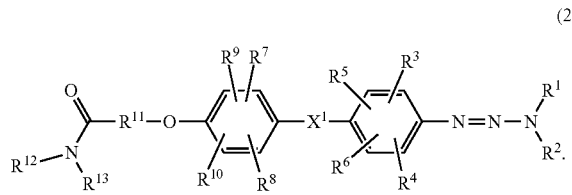

(2)

Particular preference is given according to the invention to compounds of formula (1) or (2) wherein
$R^1$ and $R^2$ are in each case alkyl,
$R^3$, $R^4$, $R^5$, $R^6$, $R^7$, $R^8$, $R^9$ and $R^{10}$ are in each case hydrogen,
$R^{11}$ is alkanediyl,
$R^{12}$ is hydrogen and $R^{13}$ is a radical A of a compound of the formula $H_2N$-A or
$R^{13}$ is hydrogen and $R^{12}$ is a radical A of a compound of the formula $H_2N$-A, wherein
A is a radical derived by cleavage of the amino group (—$NH_2$) from a natural or synthetic amino acid, a natural or synthetic amino acid derivative or a polyamino acid or polyamino acid derivative, and
$X^1$ is carbonyl (—CO—).

Most preferred are compounds selected from the group consisting of:

(Example 4)
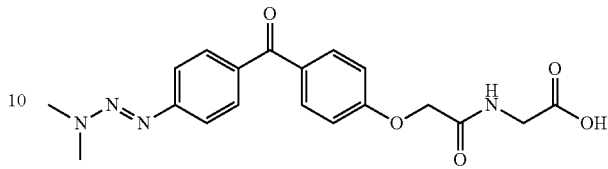

(Example 2)
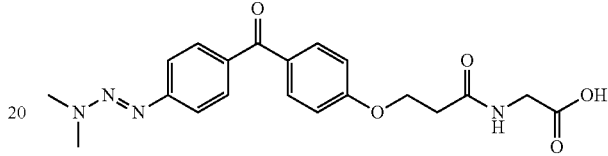

(Example 1)
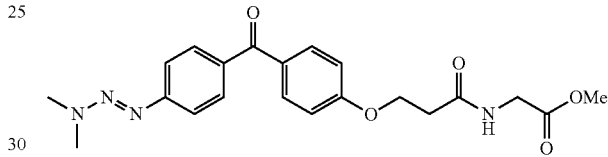

(Example 5)
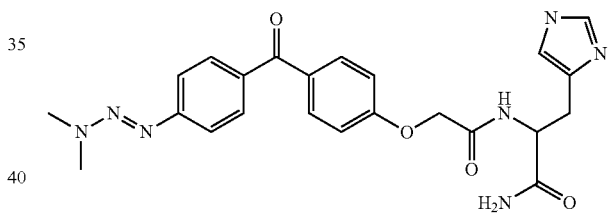

(Example 6)
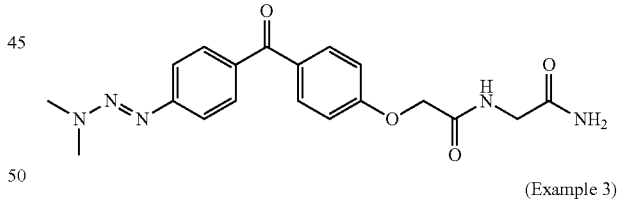

(Example 3)
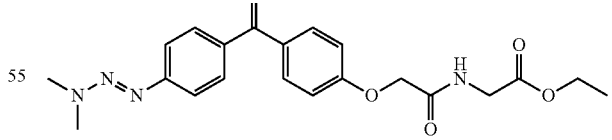

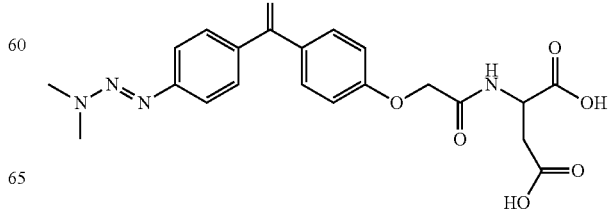

-continued

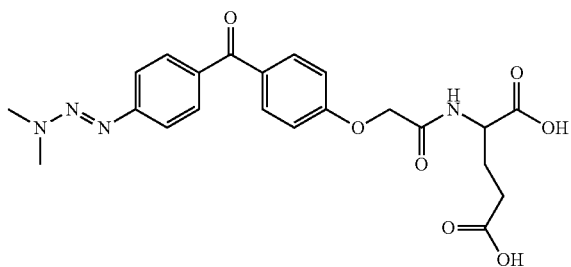

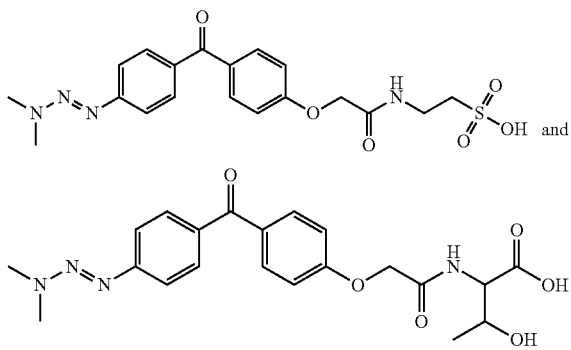

or pharmaceutically acceptable salts thereof.

The preferred compounds further include the following compounds:

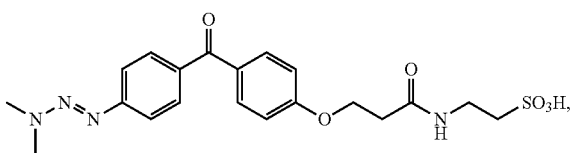
(free acid of Example 9)

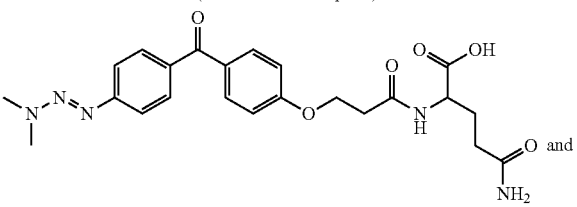
(free acid of Example 7)

(Example 8)

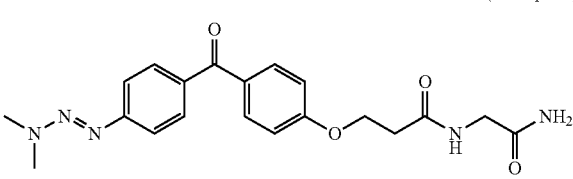

and their pharmaceutically acceptable salts.

(In these structural formulae, a structural element of the formula

for example, denotes a dimethylamino group, that is to say the methyl groups are represented by single lines, a notation which is well known to the person skilled in the art. Analogously,

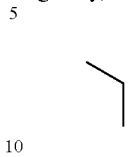

represents an abbreviated notation for a methylene radical (—CH$_2$—)).

Preference is further given according to the invention to compounds of formula (1) wherein $R^{12}$ is hydrogen and $R^{13}$ is substituted alkyl, or $R^{13}$ is hydrogen and $R^{12}$ is substituted alkyl, wherein substituted alkyl is an alkyl group having at least one sulfonic acid radical, sulfonic acid ester radical or sulfonamido radical. Particular preference is given in this connection to compounds in which substituted alkyl in the definition of $R^{12}$ or $R^{13}$ is a radical of the formula:

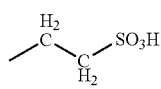

which is derived from taurine (2-aminoethane-sulfonic acid).

Triazene compounds according to the invention that contain basic groups can be used in the form of their pharmaceutically acceptable salts with pharmaceutically acceptable acids, such as, for example, salts with mineral acids, carboxylic acids and sulfonic acids, such as, for example, with hydrochloric acid, hydrobromic acid, hydriodic acid, sulfuric acid, phosphoric acid, tartaric acid, methanesulfonic acid, hydroxy-ethanesulfonic acid, aceturic acid (acetylglycine), maleic acid, propionic acid, fumaric acid, toluenesulfonic acid, benzenesulfonic acid, trifluoroacetic acid, naphthalene-1,5-disulfonic acid, salicylic acid, benzoic acid, lactic acid, malic acid, 3-hydroxy-2-naphthoic acid, citric acid or acetic acid.

Triazene compounds according to the invention that contain acidic groups can be used in the form of their pharmaceutically acceptable salts with pharmaceutically acceptable bases, such as, for example, salts with alkali or alkaline earth hydroxides, such as NaOH, KOH, Ca(OH)$_2$, Mg(OH)$_2$, etc., amine compounds, such as ethylamine, diethylamine, triethylamine, ethyldiisopropylamine, ethanolamine, diethanolamine, triethanolamine, methylglucamine, dicyclohexylamine, dimethylaminoethanol, procaine, dibenzylamine, N-methyl-morpholine, arginine, lysine, ethylenediamine, N-methyl-piperidine, 2-amino-2-methyl-1-propanol, 2-amino-2-methyl-1,3-propanediol, 2-amino-2-hydroxylmethyl-1,3-propanediol (TRIS), etc.

The water solubility, or the solubility in physiological saline, and accordingly optionally also the activity, of the compounds according to the invention can be influenced significantly by salt formation in general, specifically also by the choice of counter-ion. For example, the sodium salt of the compound

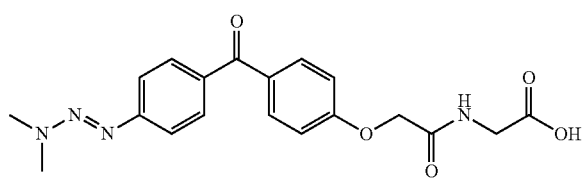 [SMILES: CN(C)/N=N/c1ccc(C(=O)c2ccc(OCC(=O)NCC(=O)O)cc2)cc1]

(Example 4a) has a solubility in water at 25° C. of about 4 g/liter, whereas the TRIS salt has a solubility in water at 25° C. of about 250 g/liter.

However, the water solubility, or the solubility in physiological saline, and accordingly optionally also the activity, of the compounds according to the invention is also significantly dependent under certain circumstances on the basic structure of the compounds themselves. For example, the compound of Example 2a) surprisingly has very good water solubility of 500 g/liter at room temperature (25° C.), which is much higher than that of the compound of Example 4a) (4 g/liter), even though it contains one more methylene group.

A high degree of water solubility of the compounds according to the invention is not absolutely critical because the predominant proportion of the substance is probably in protein-bound form in the bloodstream. Rather, it is generally important that the substances are recognised as substrate for a transport system in the body. In connection with the present invention, the so-called OATs (organic anion transporters) and OATPs (organic anion transporter proteins) are presumably of particular importance. However, these do not have 100% specificity for anions. An example thereof of digitoxin. Peptide transporters can also be discussed as relevant uptake and excretion mechanisms which recognise the amino acid or amino acid amide radical.

The use of 2-amino-2-hydroxyl-methyl-1,3-propanediol (TRIS) and sodium salts is preferred against the background of increasing the water solubility of the compounds according to the invention.

Depending on their structure, the compounds according to the invention can exist in stereoisomeric forms (enantiomers, diastereoisomers) when asymmetric carbon atoms are present. The invention therefore also includes the use of the enantiomers or diastereoisomers and mixtures thereof. The enantiomerically pure forms can optionally be obtained by conventional processes of optical resolution, such as by fractional crystallisation of diastereoisomers thereof by reaction with optically active compounds. Where the compounds according to the invention can occur in tautomeric forms, the present invention includes the use of all tautomeric forms.

The present invention relates further to a process for the preparation of the compounds of formula (1), which comprises the step:

reaction of a compound of formula (3):

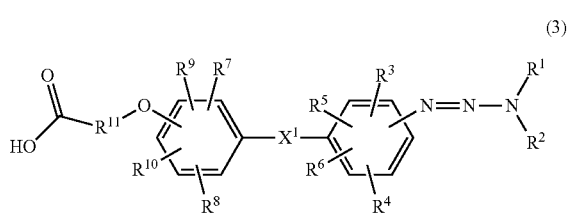

(3)

or a salt thereof, such as in particular the sodium, potassium or calcium salt thereof, with a compound of formula (4)

wherein $R^1$ to $R^{13}$ and $X^1$ are as defined hereinbefore.

The preparation of the triazene compounds (3) can be carried out analogously to the preparation method described in DE 1793115 A1 by diazotisation of the underlying amino compound, which in turn is obtained by reduction from the corresponding nitro compound. The following scheme illustrates the preparation process using the example of {2-[4-(4-[(1E)-3,3-dimethyl-1-triazenyl]-benzoyl)-phenoxy]-propionylamino}acetic acid:

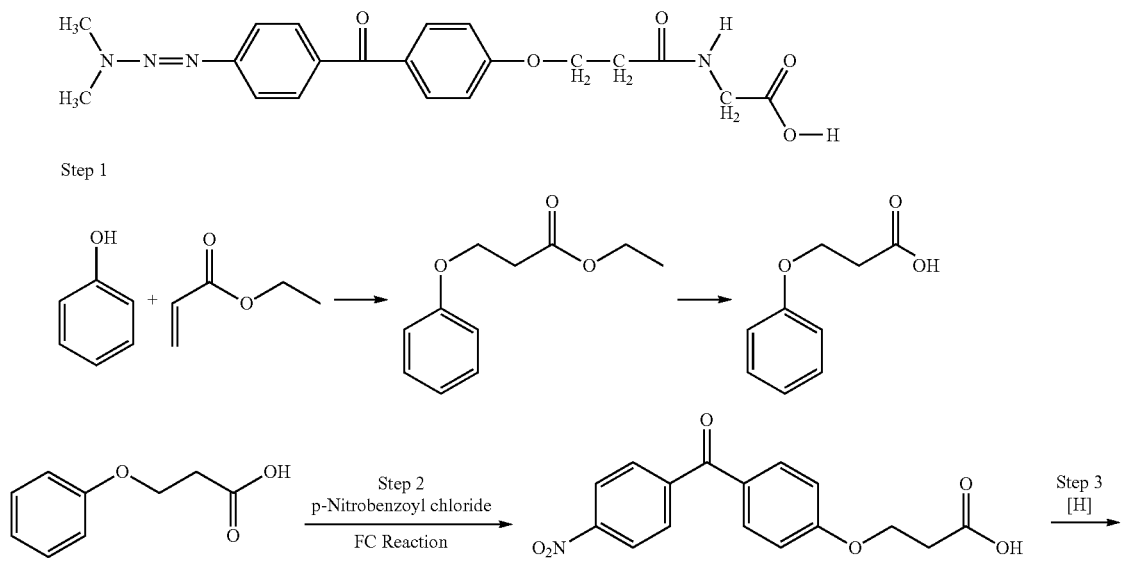

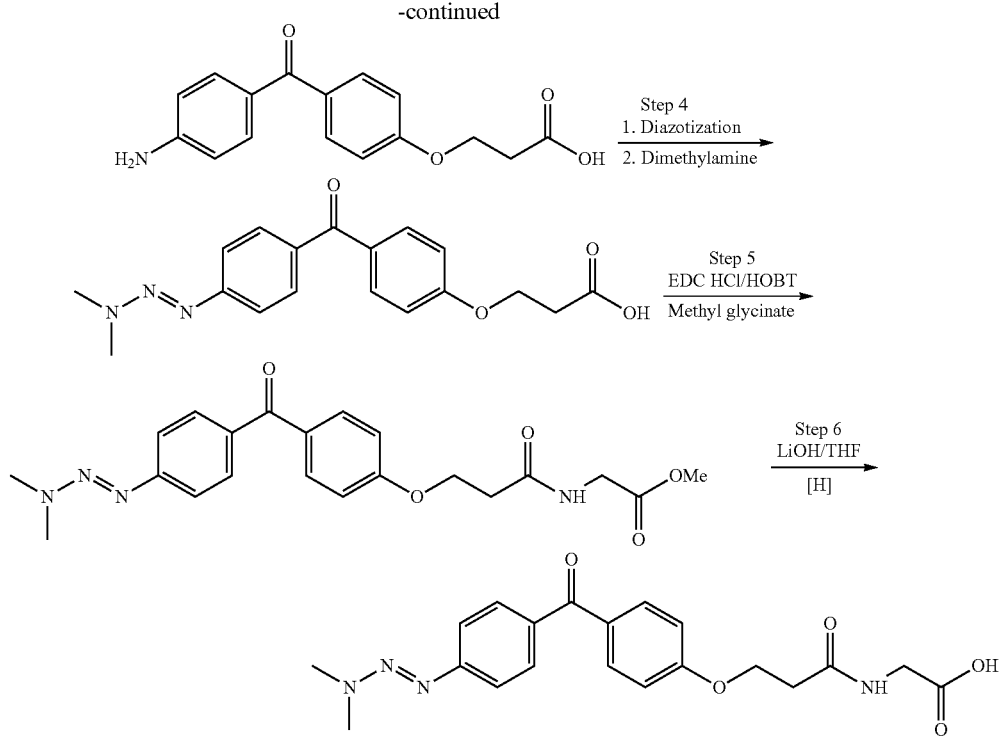

The steps shown are types of reaction which are known per se (Friedel Crafts acylation, hydrogenation or reduction of the nitro group, diazotisation, amidation and saponification) and which can be carried out in a manner known per se. The corresponding salt is obtained by reaction with a pharmaceutically acceptable base. Instead of methyl glycinate it is also possible to use in step 5 other amino compounds of the formula:

in particular also other amino acids or derivatives thereof.

Analogously to the above scheme there is obtained

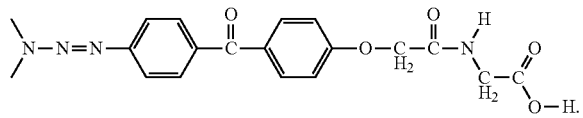

{2-[4-(4-[(1E)-3,3-dimethyl-1-triazenyl]-benzoyl)-phenoxy]-acetylamino}acetic acid and salts thereof starting from phenoxyacetic acid, which is reacted in step 2 with p-nitrobenzoyl chloride in a Friedel-Crafts reaction.

With regard to the stilbene derivatives, in which $X^1$=CH=CH—, reference may be made, for example, to WO2004/106358. The preparation of further starting compounds is described in DE 1793115 A1, which has already been mentioned, in DE 2147781 A1 and in DE 1768720 A1.

With regard to preferred reaction conditions, reference may be made to the examples.

The hydroxamic acid derivatives, in which one of $R^{12}$ and $R^{13}$ is hydrogen and the other is hydroxyl, can be reacted, for example, analogously to US 20070135424 A (for example intermediate 24) by reaction of the acid:

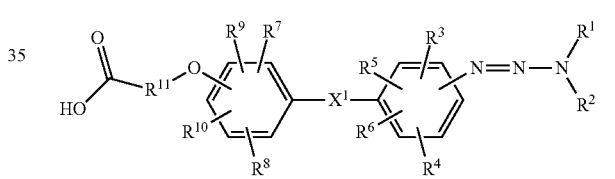

with O-(tetrahydro-2H-pyran-2-yl)-hydroxylamine to give the compound of the formula:

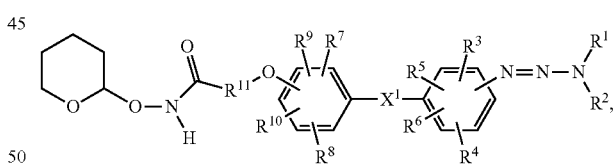

which can subsequently be converted into the corresponding hydroxamic acid by reaction with trifluoroacetic acid, for example:

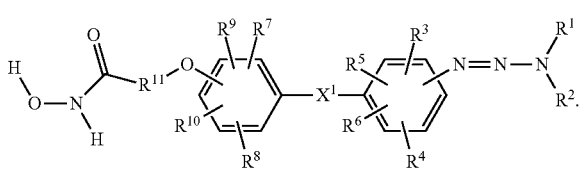

Some of the intermediates used according to the invention are novel and contribute towards the properties of the end products by the structural elements they contribute. Accordingly, the invention relates also to novel intermediates, such as in particular of formula (3'):

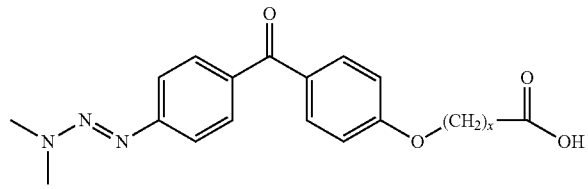

wherein x is from 2 to 6, preferably 2, and salts thereof.

The present invention relates further to compounds of formula (1) for use as medicaments, and to the use of the compounds of formula (1) in the preparation of a medicament, in particular for the treatment of cancer diseases.

The compounds according to the invention can be used, for example, in the treatment of the following types of tumour: adenocarcinoma, uveal melanoma, acute leukaemia, acoustic neuroma, ampullary carcinoma, anal carcinoma, astrocytomas, basalioma, pancreatic cancer, connective tissue tumour, bladder cancer, bronchial carcinoma, non-small cell bronchial carcinoma, breast cancer, Burkitt's lymphoma, corpus carcinoma, CUP syndrome, colon cancer, cancer of the small intestine, ovarian cancer, endometrial carcinoma, ependymoma, epithelial cancer types, Ewing's tumours, gastrointestinal tumours, gallbladder cancer, gallbladder carcinomas, uterine cancer, cervical cancer, glioblastoma, gynaecological tumours, neck, nose and ear tumours, haematological neoplasias, hairy cell leukaemia, urethral cancer, skin cancer, brain tumours (gliomas), brain metastases, testicular cancer, hypophysis tumour, carcinoids, Kaposi's sarcoma, laryngeal cancer, germ cell tumour, bone cancer, colorectal carcinoma, head/neck tumours (tumours of the neck, nose and ear region), colon carcinoma, craniopharyngeoma, cancer in the mouth region and on the lip, liver cancer, liver metastases, leukaemia, lid tumour, lung cancer, lymph gland cancer (Hodgkin's/non-Hodgkin's), lymphomas, stomach cancer, malignant melanoma, malignant neoplasma, malignomas of the gastrointestinal tract, mammary carcinoma, rectal cancer, medulloblastomas, melanoma, meningeomas, Merkel cell carcinoma, Hodgkin's disease, Mycosis fungoides, cancer of the nose, neurinoma, neuroblastoma, kidney cancer, renal cell carcinomas, non-Hodgkin's lymphomas, oligodendroglioma, oesophageal carcinoma, osteolytic carcinomas and osteoplastic carcinomas, osteosarcoma, ovarian carcinoma, pancreatic carcinoma, penile cancer, plasmocytoma, squamous cell carcinomas of the head and neck, prostate cancer, pharyngeal cancer, rectal carcinoma, retinoblastoma, vaginal cancer, thyroid carcinoma, Schneeberg lung disease, oesophageal cancer, spinalioma, T-cell lymphoma (Mycosis fungoides), thymoma, tube carcinoma, tumours of the eye, urethral cancer, urological tumours, urothelial carcinoma, vulval cancer, wart involvement, tumours of soft parts, soft part sarcoma, Wilms' tumour, cervical carcinoma and tongue cancer. Reference can additionally be made to the list of cancer types in, for example, WO2007061978 (page 16, line 22 to page 18, line 2) or in US2007135424A1 (page 9, left-hand column, section 122), which are to be regarded as part of the disclosure of the present invention. The compounds of the present invention can also be used in further indications, such as those mentioned in US2007135424A1 in sections 123 to 142.

The compounds according to the invention are used particularly preferably for the treatment of breast cancer, intestinal cancer or melanomas.

The compounds according to the invention are used particularly preferably for the treatment of breast cancer.

The invention relates further to the use of the compounds of formula (1) in combination with at least one further chemotherapeutic agent for the treatment of cancer.

The compounds of the present invention can accordingly also be used in combination with further chemotherapeutic agents known in the treatment of cancer or tumours and/or in combination with medicaments which are administered together with the chemotherapeutic agents during chemotherapy. Examples of such chemotherapeutic agents which can be used in combination and of other medicaments used in chemotherapy will be found, for example, in WO2007061978 under the heading "Combination Therapy" (page 23, line 1 to page 30, line 18) or in US2007135424A1 (sections 153 to 171), to the whole of the contents of which reference is accordingly made.

The present invention relates further to pharmaceutical compositions comprising at least one of the compounds of formula (1) together with at least one pharmacologically acceptable carrier, auxiliary substance or solvent. These are conventional pharmaceutical carriers, auxiliary substances or solvents. The mentioned pharmaceutical compositions are, for example, suitable for inhalation or for intravenous, intraperitoneal, intramuscular, intravaginal, intrabuccal, percutaneous, subcutaneous, mucocutaneous, oral, rectal, transdermal, topical, intradermal, intragastral or intracutaneous administration and are in the form of, for example, pills, tablets, enteric-coated tablets, film-coated tablets, layered tablets, retard formulations for oral, subcutaneous or cutaneous administration (in particular in plaster form), depot formulation, dragées, suppositories, gels, ointments, syrup, powders for inhalation, granules, suppositories, emulsions, dispersions, microcapsules, microformulations, nanoformulations, liposomal formulations, capsules, enteric-coated capsules, powders, powders for inhalation, microcrystalline formulations, sprays for inhalation, powders, drops, nasal drops, nasal sprays, aerosols, ampoules, solutions, juices, suspensions, emulsions, infusion solutions or injection solutions, etc.

The compounds according to the invention can be administered in pharmaceutical compositions that can comprise various organic or inorganic carriers and/or auxiliary materials as are conventionally used for pharmaceutical purposes, in particular for solid medicament forms, such as, for example, excipients (such as sucrose, starch, mannitol, sorbitol, lactose, glucose, cellulose, talc, calcium phosphate, calcium carbonate), binders (such as cellulose, methylcellulose, hydroxypropylcellulose, polypropylpyrrolidone, gelatin, gum arabic, polyethylene glycol, sucrose, starch), disintegrators (such as starch, hydrolysed starch, carboxymethylcellulose, calcium salt of carboxymethylcellulose, hydroxypropyl starch, sodium glycol starch, sodium bicarbonate, calcium phosphate, calcium citrate), glidants and lubricants (such as magnesium stearate, talc, sodium lauryl sulfate), an agent that forms a good taste (such as citric acid, menthol, glycine, orange powder), preservatives (such as sodium benzoate, sodium bisulfite, methylparaben, propylparaben), stabilisers (such as citric acid, sodium citrate, acetic acid, and multicarboxylic acids from the Titriplex group, such as, for example, diethylene-triaminepentaacetic acid (DTPA)), suspending agents (such as methylcellulose, polyvinylpyrrolidone, aluminium stearate), dispersing agents, diluents (such as water, organic solvents), beeswax, cocoa butter, polyethylene glycol, white petrolatum, etc.

Liquid medicament forms, such as solutions, suspensions and gels, conventionally comprise a liquid carrier, such as water and/or pharmaceutically acceptable organic solvents. Such liquid formulations can also comprise pH-adjusting agents, emulsifiers or dispersing agents, buffering agents, preservatives, wetting agents, gelling agents (for example methylcellulose), colourings and/or flavourings. The compositions can be isotonic, that is to say they can have the same osmotic pressure as blood. The isotonicity of the composition can be adjusted by the use of sodium chloride or other pharmaceutically acceptable agents, such as, for example, dextrose, maltose, boric acid, sodium tartrate, propylene glycol or other inorganic or organic soluble substances. The viscosity of the liquid compositions can be adjusted using a pharmaceutically acceptable thickener, such as methylcellulose. Other suitable thickeners include, for example, xanthan, carboxymethylcellulose, hydroxypropylcellulose, carbomer and the like. The preferred concentration of the thickener will depend on the chosen agent. Pharmaceutically acceptable preservatives can be used to increase the life of the liquid composition. Benzyl alcohol can be suitable, although a large number of preservatives including, for example, paraben, thimerosal, chlorobutanol or benzalkonium chloride can likewise be used.

Diethylenetriaminepentaacetic acid (DTPA) in particular is found to be a suitable stabiliser for the solid or liquid pharmaceutical formulations of the compounds according to the invention, such as in particular the compound of Example 2a).

The active ingredient can be administered, for example, in a unit dose of from 0.01 mg/kg to 500 mg/kg body weight, for example up to 1 to 4 times per day. However, the dosage can be increased or reduced according to the age, weight and condition of the patient, the severity of the disease or the mode of administration.

The invention is illustrated in detail by the following examples. The examples merely constitute exemplifications, and the person skilled in the art is able to extend the specific examples to further claimed compounds.

EXAMPLES

Starting Preparations

Preparation 1:

The preparation of the starting compound

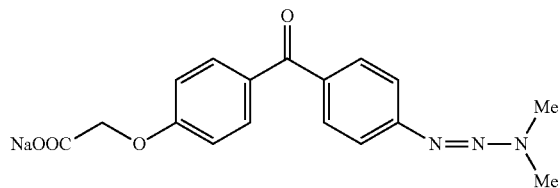

is carried out according to the following reaction scheme:

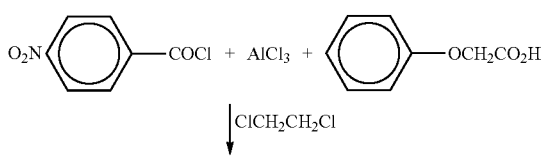

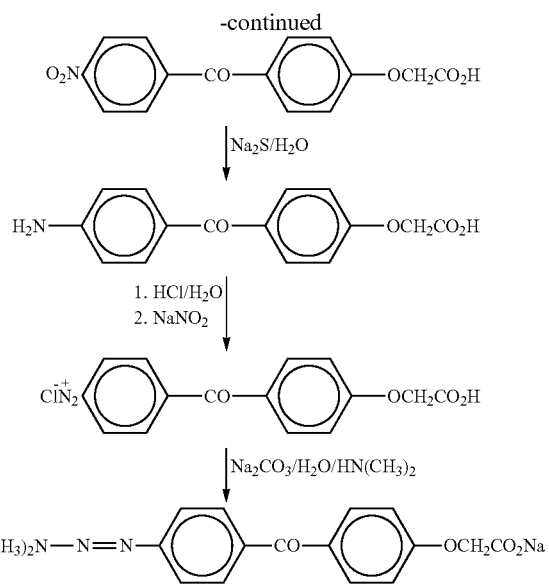

All the starting materials are well known and documented. The NMR spectra of all the synthesised products are in agreement with the structure.

Stage I

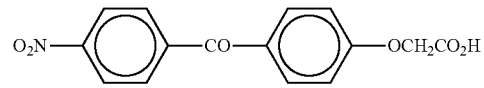

MW: 301: C15H11NO6

0.5 mol 102 g of p-nitrobenzoyl chloride (0.55 mol) dissolved in 300 ml of dichloroethane are slowly added dropwise at 0°-5° C., with stirring, to a suspension of 235 g of $AlCl_3$ in 1 litre of dichloroethane. 76 g of phenoxyacetic acid are introduced in portions into the solution at 5° C. Stirring is then carried out for 4 hours at 10° C. and for 10 hours at room temperature.

Working Up:

600 ml of dichloroethane are distilled off, and 600 ml of ligroin are added. The mixture is then poured onto 2 liters of ice/water. The aqueous phase is separated off and the resulting crystalline product is filtered off with suction, washed with water and dried.

Yield: 100 g; m.p.: 186° C., white product.

Stage II

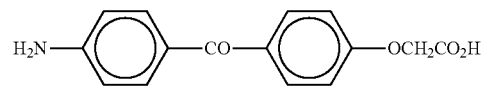

MW: 271; C15H13NO4; Lit.: Houben Weyl 11/1 p. 417

0.5 mol 320 g of I are boiled at reflux, with stirring, in 1 liter of ethanol. A solution of 350 g of $Na_2S$ and 350 ml of water is carefully added dropwise thereto (strongly exothermic, $H_2S$ absorption). Boiling is then carried out for 2 hours at reflux. The reaction mixture is then allowed to stand for about 10 hours at room temperature.

Working Up:

The alcohol is distilled off and the residue is extracted, with stirring, with 3 liters of hot water and filtered off with suction while hot. The filtrate is acidified with glacial acetic acid and the resulting product is filtered off with suction, washed with water, filtered off with suction again and dried.

Purification: from ethanol
Yield: 200 g=74%, weakly yellow product;
M.p.: 172° C.
Stage III:

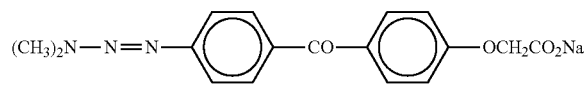

MW: 349; C17H16N3O4Na
0.1 mol

A solution of 6.9 g of NaNO$_2$ in 20 ml of water is added dropwise at 0° C., with stirring, to a solution of 27.1 g of II, 350 ml of water and 10.4 g of concentrated HCl (37%), and stirring is carried out for a further 15 minutes at 0° C. The resulting diazonium salt solution is added dropwise at 0-5° C., with stirring, to a solution, placed in a vessel, of 15 g of Na$_2$CO$_3$ and 10 g of a 45% aqueous dimethylamine solution and 50 ml of water.

Working Up:
The reaction mixture is kept cold, and the resulting salt is filtered off with suction and recrystallised from water.

Purification:
Recrystallisation from water. Solubility: 1 g in 25 ml of water.
Yield: 10 g=28%, beige; m.p. of the acid: 160° C. The acid is obtained by dissolving the salt in water and precipitating with acetic acid.

Preparation 2:
The preparation of the phenoxypropionyl starting compound

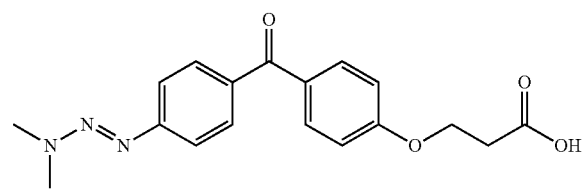 [SMILES: CN(C)/N=N/c1ccc(C(=O)c2ccc(OCCC(=O)O)cc2)cc1]

is carried out as shown in the scheme in the description.

Step 1:
The following materials were used in the indicated amounts:

|  | Amount | Molecular weight | Mol | Eq. |
| --- | --- | --- | --- | --- |
| Phenol | 1 kg | 94.11 | 10.62 | 1 |
| Ethyl acrylate | 2.7 kg | 100 | 27 | 2.54 |
| Triton B | 1 ml |  |  |  |
| NaOH (10%) | 3 l | 40 | 7.5 | 0.705 |
| Ethyl acetate | 5 l |  |  |  |
| Conc. HCl | 3.5 l |  |  |  |

Phenol and ethyl acrylate were introduced into a 5-liter three-necked glass flask equipped with a thermal element and an overhead stirrer. Triton B was added, and heating was carried out for 48 hours under reflux (120° C.). TLC showed that a small amount of phenol was still present. The reaction composition was worked up as follows. Ethyl acetate was removed, and the residue was dissolved in ethyl acetate, washed with aqueous NaOH (10%) followed by water (3.0 liters) and dried over anhydrous sodium sulfate. The dried organic layer was concentrated to give a residue. The residue was placed in a 10.0-liter round-bottomed glass flask, concentrated HCl was added, and heating was carried out for 24 hours under reflux. The TLC was checked and the reaction composition was cooled to 25° C. The solids were filtered off and washed thoroughly with water (5 liters). The product was dried overnight at 30° C. in vacuo in an oven.

Yield: 450 g (27% of theory)
Purity (HPLC): 98.32%

(Alternatively, the product can also be prepared by saponification of the underlying nitrile according to the following scheme:

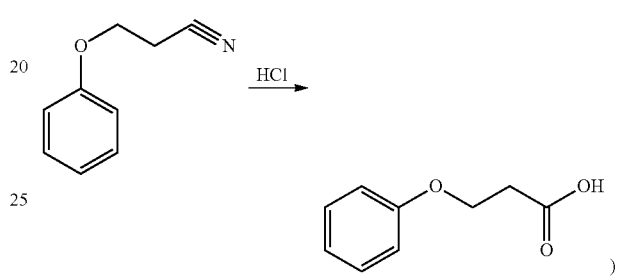

Step 2:
The following materials were used in the indicated amounts:

|  | Amount | Molecular weight | Mol | Eq. |
| --- | --- | --- | --- | --- |
| 4-Nitrobenzoic acid | 300 g | 167 | 1.796 | 1 |
| Thionyl chloride | 1.5 l | 119 | 20.62 | 11.5 |
| DMF | 0.05 ml |  |  |  |
| Dichloroethane | 12.5 l |  |  |  |
| AlCl$_3$ | 720 g | 133.3 | 5.4 | 3 |
| Step 1 product | 280 g | 166 | 1.687 | 0.94 |
| Hexane | 8 l |  |  |  |
| Ice-water | 15 l |  |  |  |

4-Nitrobenzoic acid, thionyl chloride and DMF were placed in a 3-liter 4-necked glass flask and heated for 2 hours at 78° C. under reflux. The end of the reaction was monitored by the clarity of the reaction mixture. There was a clear solution at the end of the reaction. Thionyl chloride was removed under reduced pressure. Dichloroethane (1 liter) was added, and evaporation was carried out to yield 4-nitrobenzoyl chloride in the form of a solid. The solid was dissolved in dichloroethane (1 liter). Dichloroethane (10 liters) was introduced into a 20-liter glass flask and cooled to 0° C. Aluminium chloride was added at 0-5° C. The 4-nitrobenzoyl chloride prepared above, dissolved in dichloroethane, was then added dropwise at 0-5° C. Phenoxypropionic acid was added in portions to the reaction composition at 0.5° C., and stirring was carried out overnight at 25° C. The TLC was checked and the reaction composition was quenched in a mixture of hexane (8 liters) and ice-water (15 liters). The composition was stirred and the solids were filtered off. The product was washed with hexane and dried.

Yield: 400 g (70% of theory)
Purity: 92.8% by HPLC.

Step 3

The following materials were used in the indicated amounts:

|  | Amount | Molecular weight | Mol | Eq. |
| --- | --- | --- | --- | --- |
| Step 2 product | 400 g | 315 | 1.26 | 1 |
| Na₂S | 400 g | 78 | 5.13 | 4 |
| Ethanol | 4 l | | | |
| Water | 1 l | | | |

The product from step 2 was taken up in ethanol and cooled to 10° C. An aqueous solution of the sodium sulfide was added dropwise at 10-15° C., and stirring was carried out overnight at 25° C. Ethanol was removed, and water (4 liters) was added under reduced pressure. Acetic acid was added in order to adjust the pH to 6. The pH of the filtrate was adjusted to 3 with acetic acid, and extraction with ethyl acetete (3 liters) was carried out. The organic layer was dried and concentrated to give a residue.

Yield: 168 g
Purity: >70% by HPLC.
A similar batch was prepared with 230 g of the product from step 2.
Yield: 108 g
Purity: 66.1% by HPLC.
The above two batches of the product were mixed and recrystallised from ethanol.
Combined yield: 110 g (19.3% of theory)
Purity: 95.6% by HPLC.

Step 4:

The following materials were used in the indicated amounts:

|  | Amount | M.W. | Mol | Eq. |
| --- | --- | --- | --- | --- |
| Step 3 product | 110 g | 285 | 0.3859 | 1 |
| Conc. HCl | 130 ml | 36.5 | 1.31 | 3.4 |
| Water | 2 l | | | |
| NaNO₂ | 30 g | 69 | 0.04347 | 1.12 |
| Na₂CO₃ | 67.5 g | 106 | 0.6367 | 1.65 |
| Dimethylamine (40%) | | | | |

Mixed product from step 3, water (2 liters) and concentrated HCl were cooled to 0° C. Sodium nitrite was dissolved in water (150 ml) and added at 0-5° C., and stirring was carried out for 30 minutes.

In another glass flask, sodium carbonate was dissolved in water (160 ml); dimethylamine was added and the mixture was cooled to 0° C. The sodium diazonium salt was added slowly at 0-5° C. to the solution prepared above, and stirring was carried out for one hour. The TLC was checked and the reaction was completed. The pH of the reaction composition was adjusted to 3 with acetic acid, and extraction with ethyl acetate (1.2 liters) was carried out. The organic layer was washed with water (200 ml×2), dried over anhydrous sodium sulfate and concentrated to give a solid.

Crude yield: 109.5 g
Purity: 84.7%
The crude product was purified by column chromatography (20% THF in ethyl acetate).
Yield: 85 g (64.6% of theory)
Purity: 93.3% by HPLC.

The product of Preparation 2 has a melting point of from 124.5 to 125.8° C.

FIG. 19 shows the ¹H-NMR spectrum of the resulting compound.

Example 1

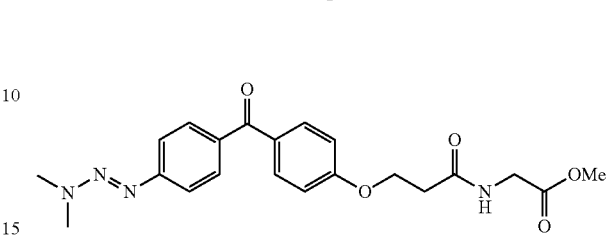

(Step 5 of the Above Scheme):

The following materials were used in the indicated amounts:

|  | Amount | Molecular weight | Mol | Eq. |
| --- | --- | --- | --- | --- |
| Step 4 product | 85 g | 341.36 | 0.249 | 1 |
| EDC HCl | 52.5 g | 191.7 | 0.274 | 1.1 |
| HOBT | 8 g | | | |
| Methyl glycinate HCl | 31.23 g | 125.8 | 0.249 | 0.99 |
| TEA | 75.89 g | 101 | 0.7514 | 3 |
| DCM | 850 ml | | | |

The product from step 4 was dissolved in DCM and cooled to 10° C. HCl and HOST were added to the EDC, and stirring was carried out for 30 minutes. Methyl glycinate was added at 10° C., and stirring was carried out overnight at 27° C. The TLC was checked and it was found that the reaction was complete. Water (1 liter) was added and the layer was separated. The organic layer was dried over sodium sulfate and concentrated to give a residue.

Crude yield: 110 g
Purity: 91.3% by HPLC
The crude product was purified further by column chromatography (10% ethyl acetate in hexane).
Yield: 89 g (86% of theory)
Purity: 95.4% by HPLC.
The product is a pink-coloured powder having a melting point of 104.0 to 105.0° C. A main peak is observed in the mass spectrum at 413.5 (M+1).

FIG. 1 shows the ¹H-NMR spectrum (400 MHz) of the compound of Example 1.

Figure 2:
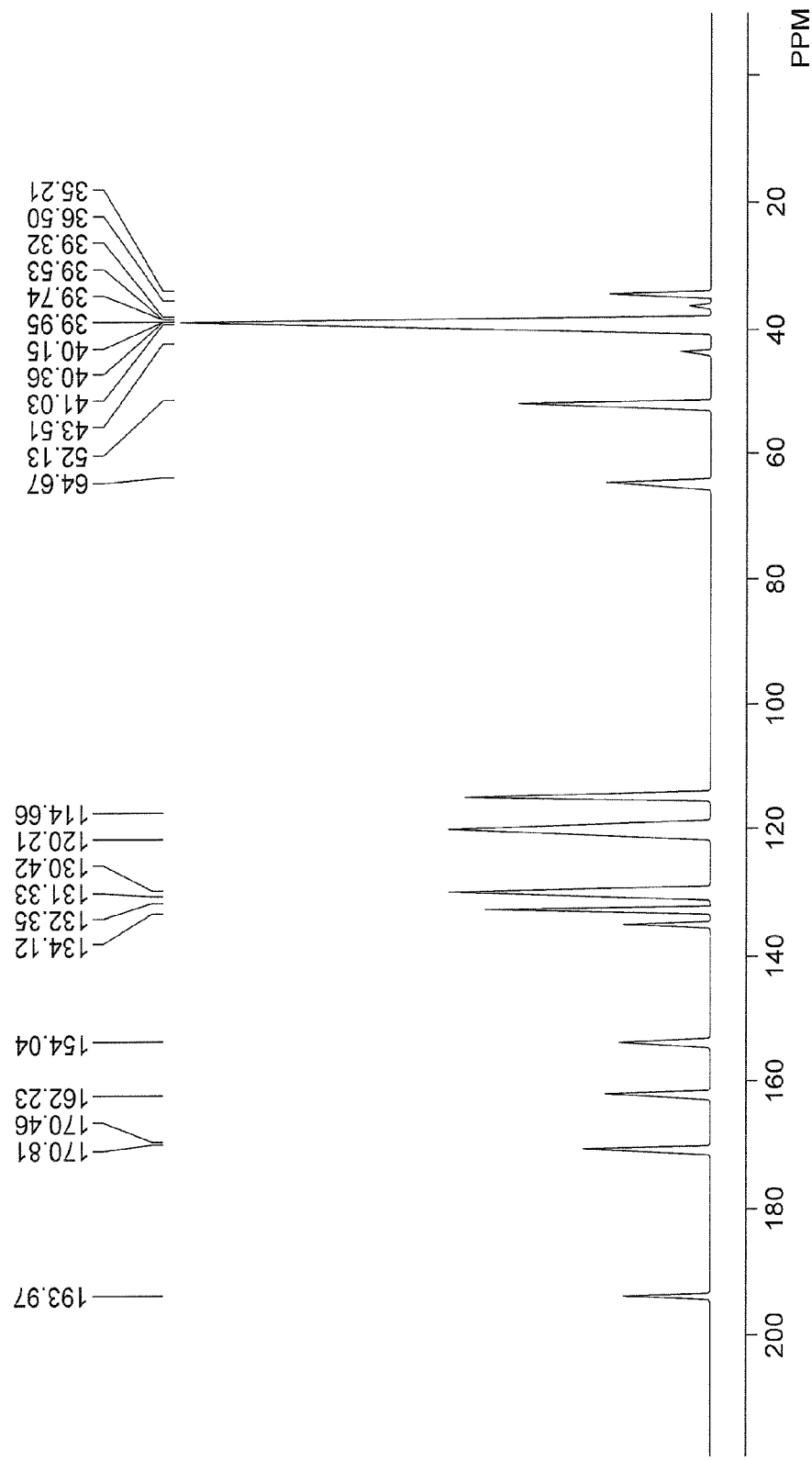
FIG. 2 shows the $^{13}$C-NMR spectrum (100 MHz) of the compound of Example 1.

FIG. 2 shows the ¹³C-NMR spectrum (100 MHz) of the compound of Example 1.

Example 2

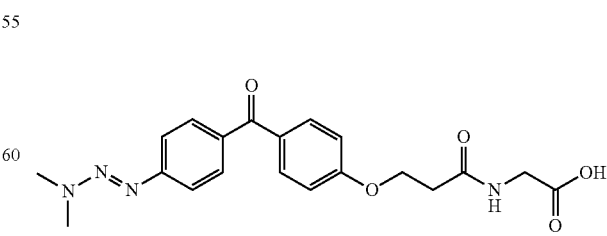

(Step 6 of the Above Scheme)

The following materials were used in the indicated amounts:

|  | Amount | Molecular weight | Mol | Eq. |
| --- | --- | --- | --- | --- |
| Step 5 product | 89 g | 412 | 0.2157 | 1 |
| LiOH H$_2$O | 9.5 g | 41.96 | 0.2264 | 1.05 |
| THF | 890 ml | | | |
| Water | 178 ml | | | |

The product of step 5, THF and water were mixed and cooled to 0° C. Lithium hydroxide (4.5 g) was added in portions at 0° C., and stirring was carried out for 20 minutes. The TLC was checked, the reaction had not begun. A further batch of LiOH (4.5 g) was added, and stirring was carried out for 30 minutes. The TLC was checked and it was found that the reaction had begun. The reaction composition was maintained for one hour, and the TLC was checked. A very small amount of the substrate remained. Yet a further batch of lithium hydroxide (0.5 g) was added. The TLC was checked after 30 minutes and the substrate had disappeared. THF was removed in vacuo and the residue was diluted with ethyl acetate (2 liters). The pH was adjusted to 5-6, a clear solution was obtained. Washing with water (200 ml×2) was carried out, followed by drying over sodium sulfate and concentration to give a residue.

Yield: 72 g

The crude product was purified further by column chromatography (DCM/methanol).

Yield: 46 g (53.5% of theory)
Purity: 95.9%.

The product is a yellow hygroscopic solid. A main peak is observed in the mass spectrum at 399.1 (M+1).

Figure 3:
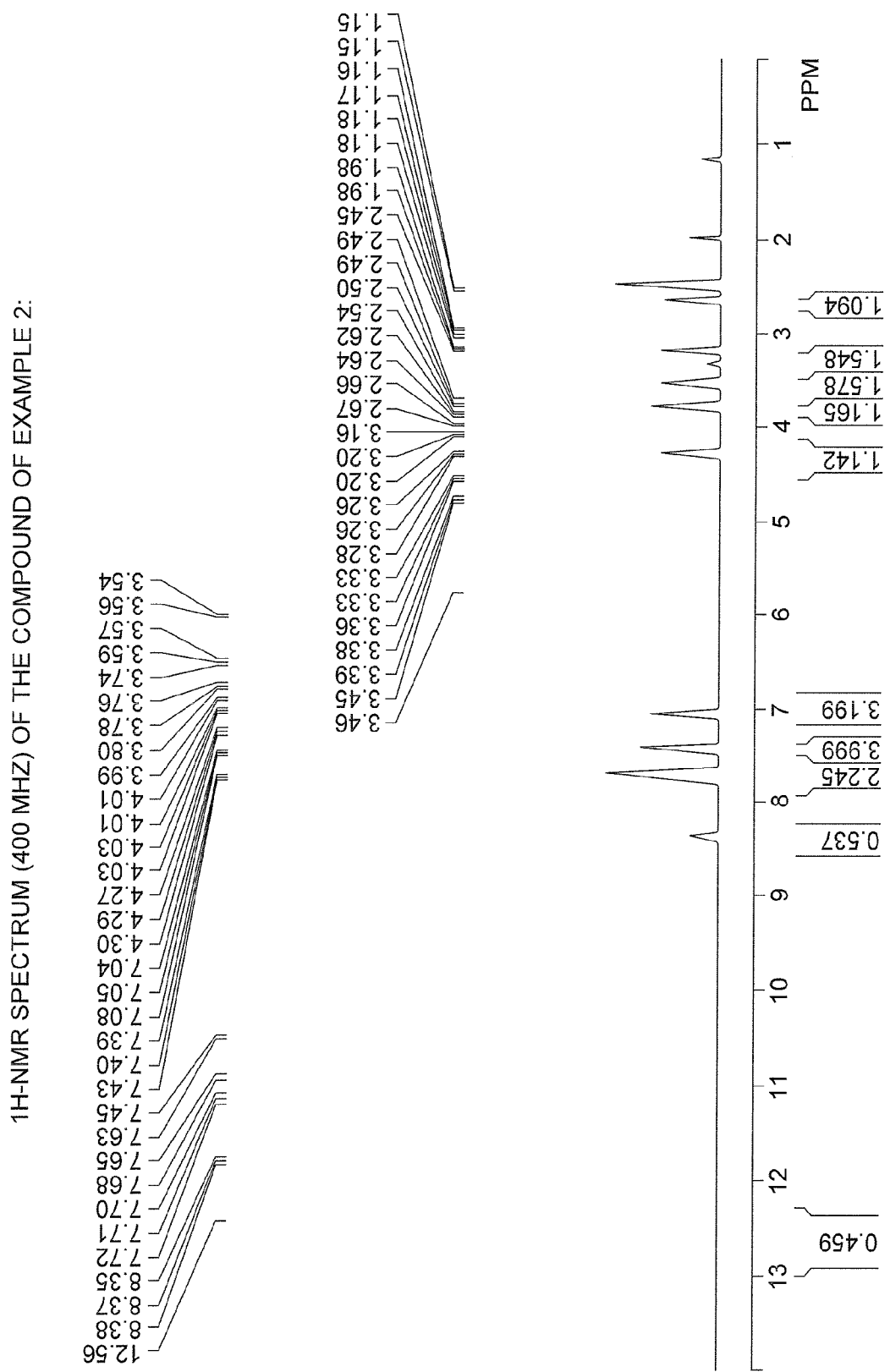
FIG. 3 shows the $^1$H-NMR spectrum (400 MHz) of the compound of Example 2.

FIG. 3 shows the $^1$H-NMR spectrum (400 MHz) of the compound of Example 2.

Example 2a

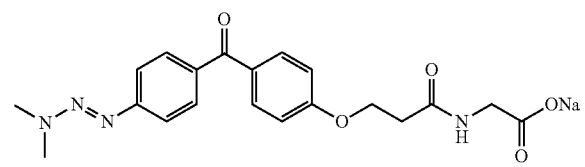

A solution of sodium carbonate (1.49 g, 0.0140 mol) in water (3.75 ml) was added to 7 g of the compound obtained in Example 2. Ethyl acetate (50 ml) was added thereto and stirring was carried out. The resulting product was stirred overnight (about 12 hours) with tetrahydrofuran (100 ml) at room temperature (25° C.). The solid was filtered off and washed with dichloromethane (50 ml) and ethyl acetate (100 ml). The solid was dried overnight (about 12 hours) at 50° C. in vacuo, and the sodium salt of the compound of Example 2 was obtained.

Yield: 5.7 g (56% of theory)
Purity HPLC: 97.4%

The product is a weakly orange-coloured crystalline powder. It surprisingly has a very good water solubility of 500 g/l at room temperature (25° C.), which in particular is very much higher than that of the compound of Example 4a), even though it has one more methylene group.

Figure 4:
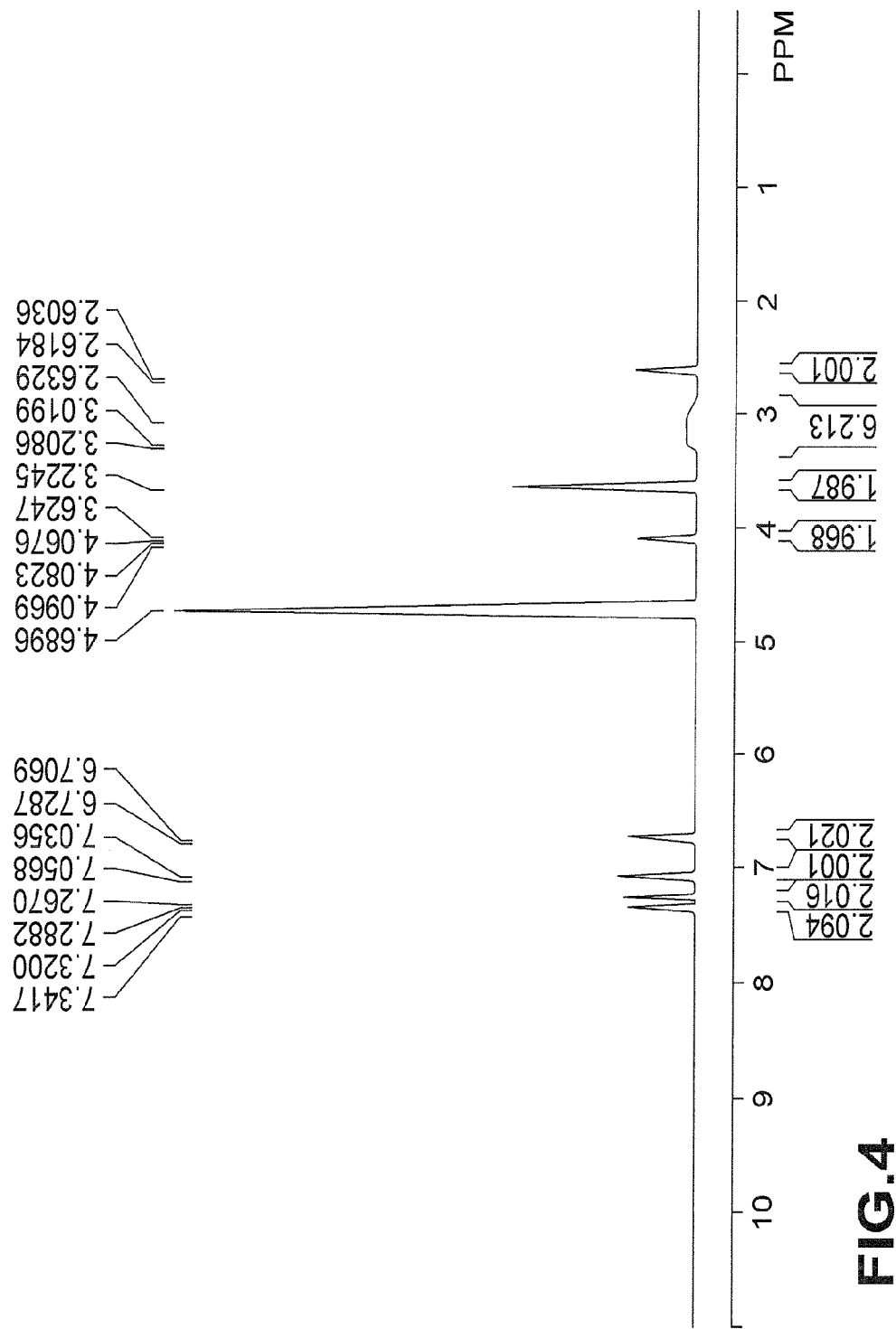
FIG. 4 shows the $^1$H-NMR spectrum (400 MHz-D$_2$O) of the compound obtained in Example 2a).

FIG. 4 shows the $^1$H-NMR spectrum (400 MHz-D$_2$O) of the compound obtained in Example 2a).

Figure 5:
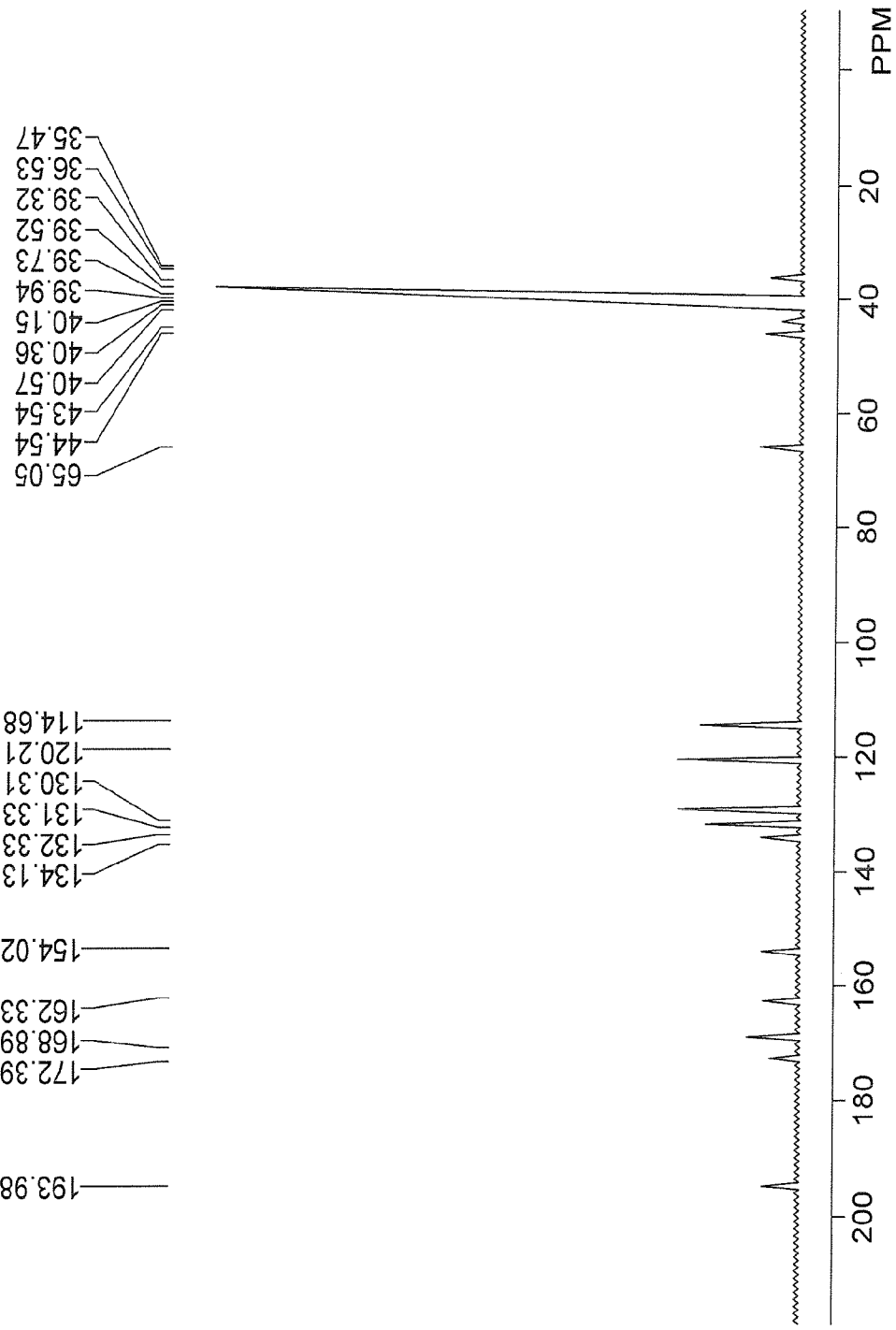
FIG. 5 shows the $^{13}$C-NMR spectrum (100 MHz-d$^6$-DMSO) of the compound obtained in Example 2a).

FIG. 5 shows the $^{13}$C-NMR spectrum (100 MHz-d$^6$-DMSO) of the compound obtained in Example 2a).

Example 3

Starting from Preparation 1 with ethyl glycinate, the following compound was obtained analogously to Example 1 in the form of a yellow powder having a purity of >95% (HPLC).

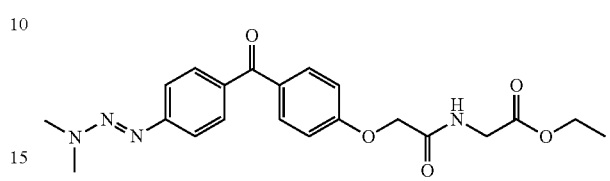

Figure 6:
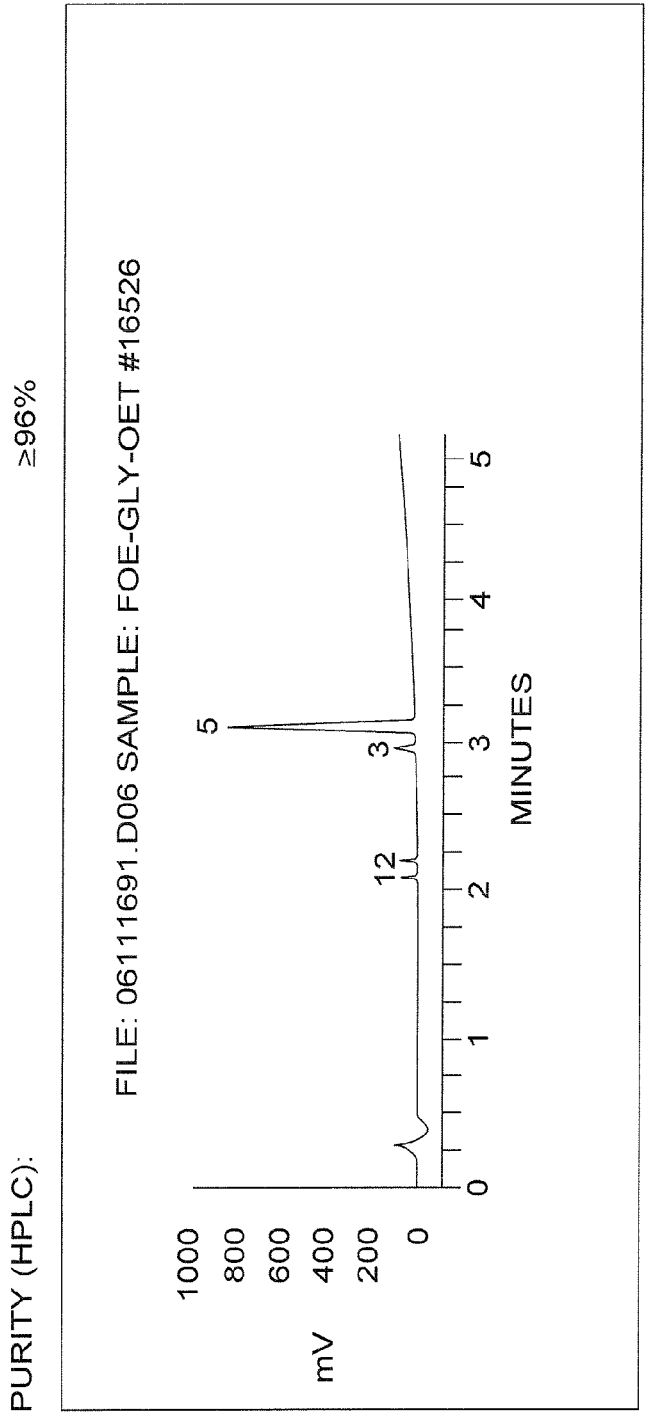
FIG. 6 shows the result of the HPLC of the compound obtained in Example 3.

FIG. 6 shows the result of the HPLC of the compound obtained in Example 3.

Example 4

Starting from Example 3, the following compound was obtained analogously to Example 2:

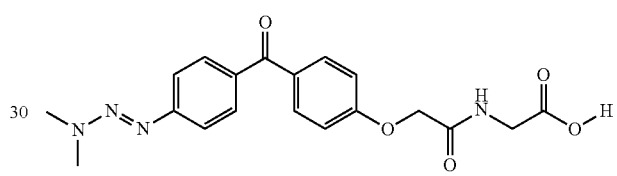

Yellow solid; purity (HPLC)>99%; melting point 130.7 to 131.2° C.

Figure 7:
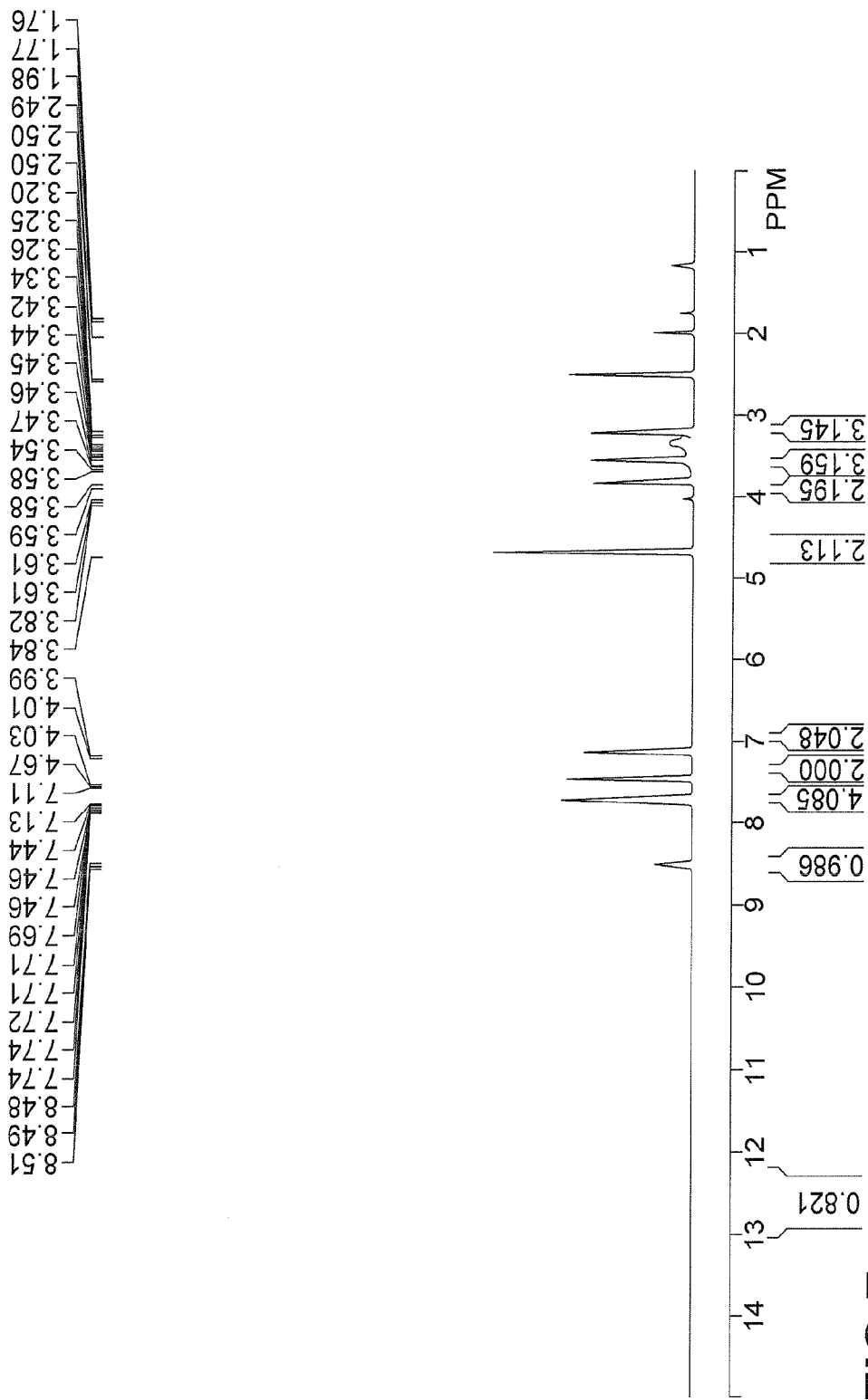
FIG. 7 shows the $^1$H-NMR spectrum (400 MHz-d$^6$-DMSO) of the compound obtained in Example 4.

FIG. 7 shows the $^1$H-NMR spectrum (400 MHz-d$^6$-DMSO) of the compound obtained in Example 4.

Figure 8:
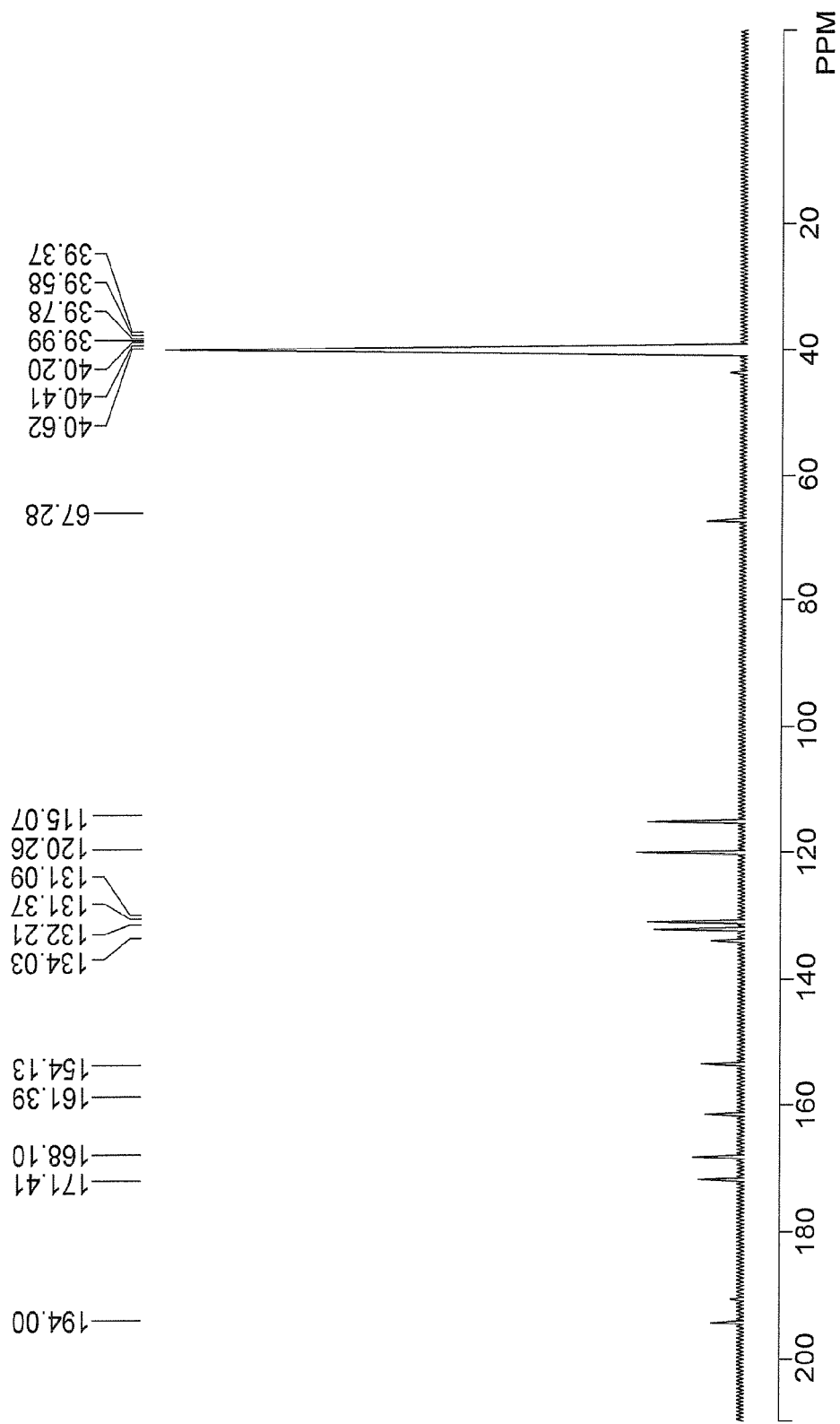
FIG. 8 shows the $^{13}$C-NMR spectrum (100 MHz-d$^6$-DMSO) of the compound obtained in Example 4.

FIG. 8 shows the $^{13}$C-NMR spectrum (100 MHz-d$^6$-DMSO) of the compound obtained in Example 4.

Example 4a

The sodium salt of the compound of Example 4 was obtained analogously to Example 2a) by reaction with sodium carbonate.

It is a cream-coloured powder having a melting point of 253.2 to 253.9° C.

Figure 9:
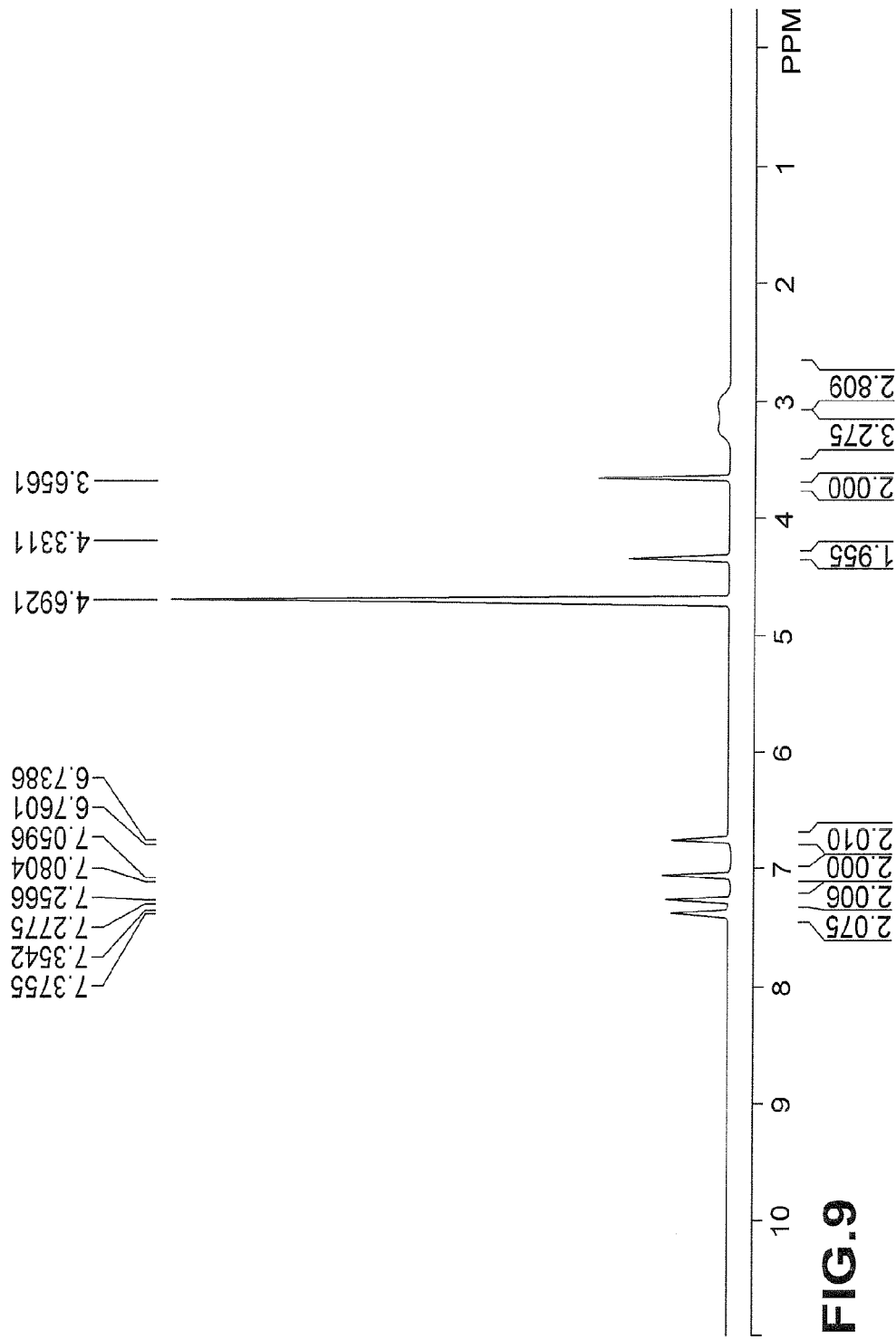
FIG. 9 shows the $^1$H-NMR spectrum (400 MHz-D$_2$O) of the compound obtained in Example 4a).

FIG. 9 shows the $^1$H-NMR spectrum (400 MHz-D$_2$O) of the compound obtained in Example 4a).

Figure 10:
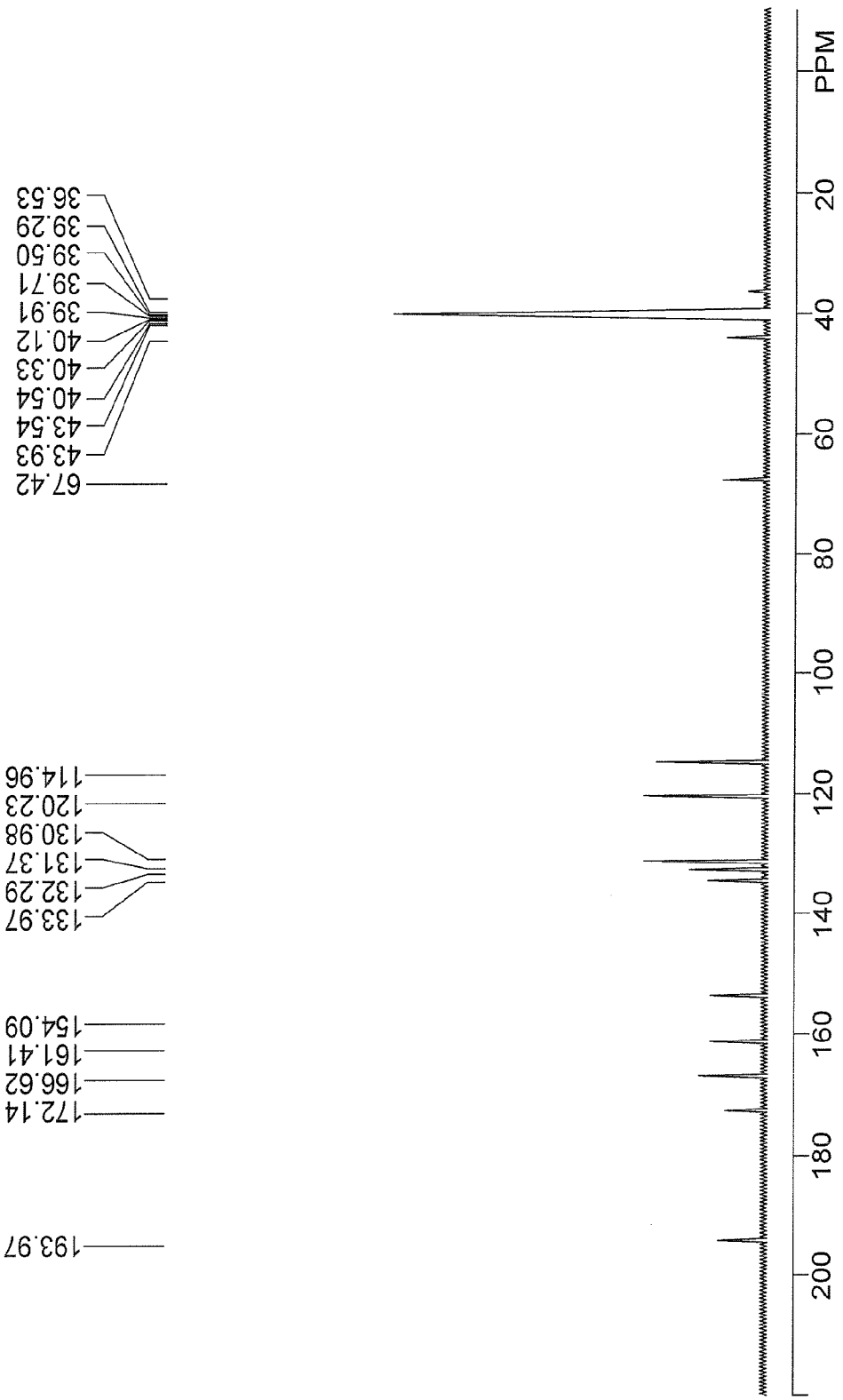
FIG. 10 shows the $^{13}$C-NMR spectrum (100 MHz-d$^6$-DMSO) of the compound obtained in Example 4a).

FIG. 10 shows the $^{13}$C-NMR spectrum (100 MHz-d$^6$-DMSO) of the compound obtained in Example 4a).

Further salts of the compound of Example 4 can be obtained in an analogous manner by reaction with other bases, such as TRIS (tris(hydroxymethyl)-aminomethane or 2-amino-2-(hydroxymethyl)-propane-1,3-diol).

The TRIS salt in particular exhibits markedly higher water solubility at room temperature than the sodium salt (250 g/liter, corresponding to a factor of about 60 compared with the sodium salt), which in addition exhibits a pronounced salting-out effect in 0.9% NaCl.

Example 5

Starting from Preparation 1 with histidineamide, the following compound was obtained analogously to Example 1 in the form of a yellow powder having a purity of >95% (HPLC):

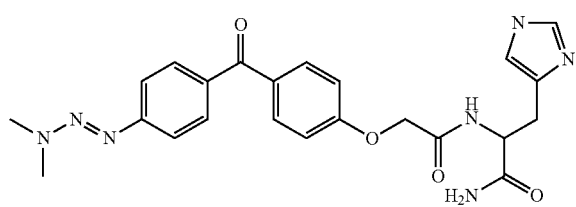 [SMILES: CN(C)/N=N/c1ccc(C(=O)c2ccc(OCC(=O)NC(Cc3c[nH]cn3)C(N)=O)cc2)cc1]

Figure 11:
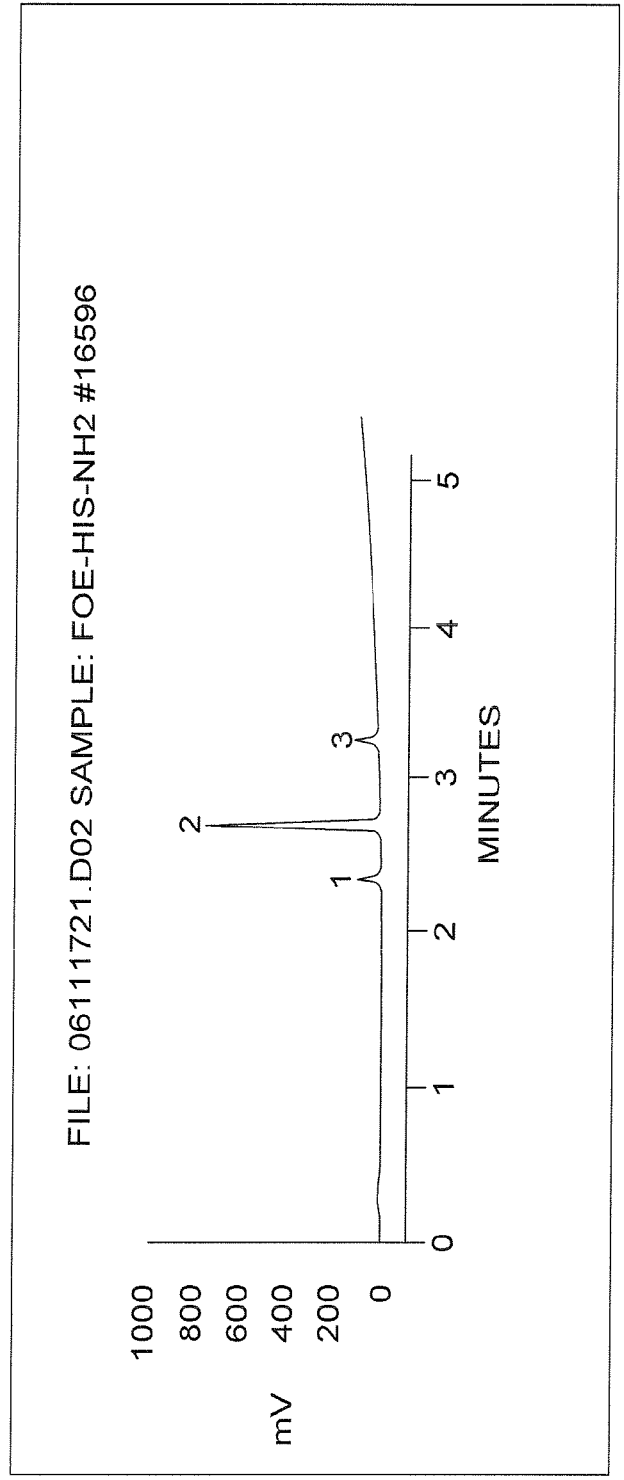
FIG. 11 shows the result of the HPLC of the compound obtained in Example 5.

FIG. 11 shows the result of the HPLC of the compound obtained in Example 5.

Example 6

Starting from glycineamide, the following compound was obtained analogously to Example 1 in the form of a light-brown powder in a purity of >95% (HPLC):

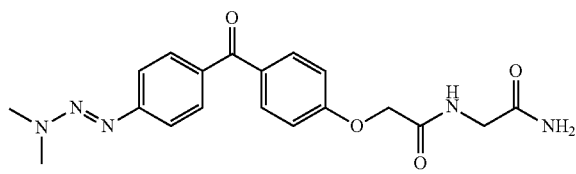 [SMILES: CN(C)/N=N/c1ccc(C(=O)c2ccc(OCC(=O)NCC(N)=O)cc2)cc1]

Figure 12:
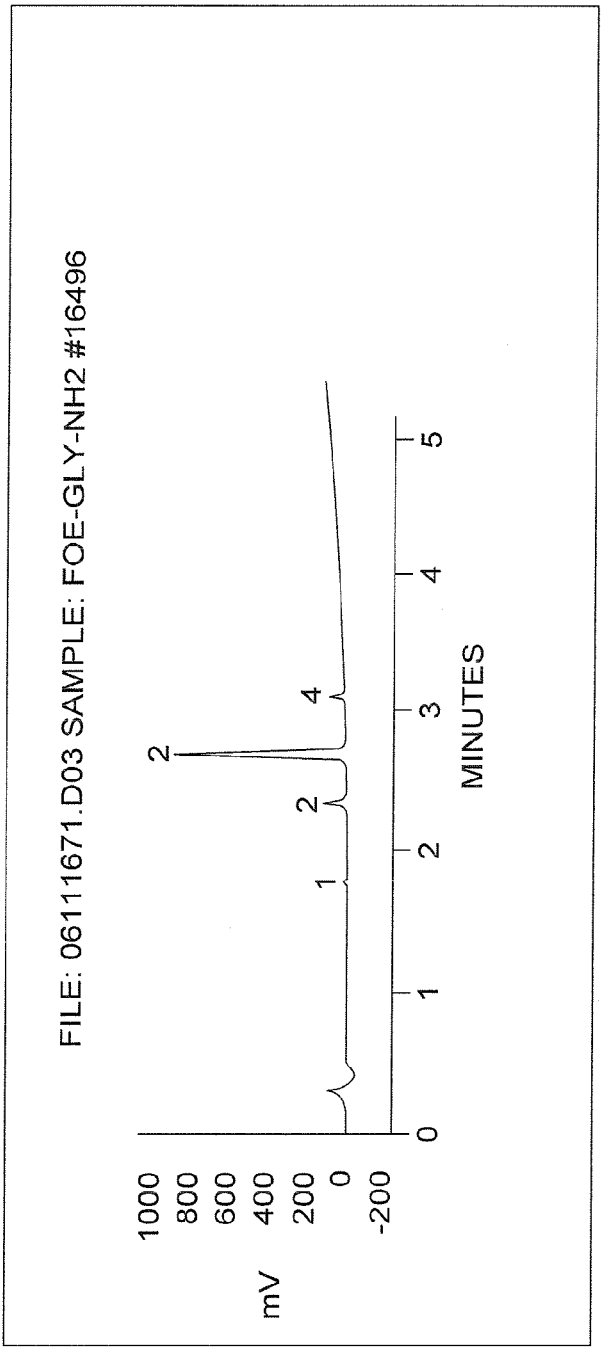
FIG. 12 shows the result of the HPLC of the compound obtained in Example 6.

FIG. 12 shows the result of the HPLC of the compound obtained in Example 6.

Example 7

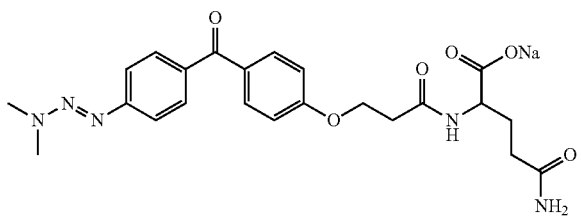

(4-carbamoyl-2-{3-[4-(4-[(1E)-3,3-dimethyl-1-triazenyl]-benzoyl)-phenoxy]-propionylamino}-butanoic acid sodium salt)
was prepared as follows starting from

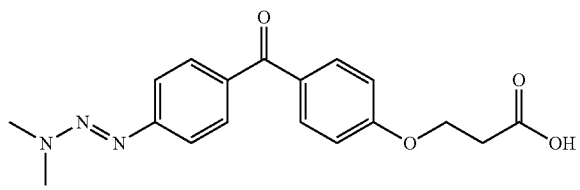 [SMILES: CN(C)/N=N/c1ccc(C(=O)c2ccc(OCCC(=O)O)cc2)cc1]

(3-{4-{4-[(1E)-3,3-dimethyl-1-triazenyl]-benzoyl}-phenoxy}-propionic acid):
In a one-liter three-necked round-bottomed flask having a thermal element pocket and a stirrer, (3-{4-{4-[(1E)-3,3-dimethyl-1-triazenyl]-benzoyl}-phenoxy}propionic acid) (40 g, 0.1173 mol) as starting compound, HOBt (3.7 g, 0.0274 mol) and dioxane (300 ml) were added to an ice-water bath. A solution of DCC (40.66 g, 0.1970 mol) in dioxane (100 ml) was added dropwise thereto over a period of 5 to 6 hours, whereby the temperature was maintained at 20 to 25° C. In another 2-liter three-necked round-bottomed flask having a thermal element pocket and a stirrer, L-glutamine (43.20 g, 0.2956 mol) and saturated sodium bicarbonate solution (432 ml) were added to an ice-water bath. The dioxane solution prepared above was added thereto, and stirring was carried out for 16 hours at 10 to 15° C. The start of the reaction was monitored by TLC (thin-layer chromatography) (MDC:MeOH, 1:1). After 16 hours, TLC showed that the starting compound had reacted completely. The pH of the reaction mixture was adjusted to 6.8 using HCl (1.5 N), and the reaction mixture was concentrated under reduced pressure at 50° C. Water (200 ml) was added to the residue, and stirring was carried out at 25° C. The suspension was filtered and the pH of the filtrate was adjusted to 3.08 using HCl (1.5 N). The reaction mixture was extracted with ethyl acetate (200 ml) and the phases were separated. The organic layer was dried over sodium sulfate (25 g). The organic layer was rinsed for 2 hours with dry ammonia (a rubber-like residue was formed) and the supernatant liquid was decanted off. The residue was rinsed with a mixture of THF:EtOAc (1:1, 100 ml) and decanted off. The process was repeated five times (after this treatment, the residue was a movable solid) and filtration was then carried out. The crude solid was maintained under reflux (78 to 80° C.) for one hour in ethanol (100 ml). The hot suspension was filtered and the filtrate was cooled to 20° C. for 2 hours. After 2 hours, the suspension was filtered and the filter cake (12 g) was dissolved in water (120 ml). The pH of the solution was adjusted to 3.0 using HCl (1.5 N), and extraction with ethyl acetate (120 ml) was carried out. The phases were separated and the organic layer was washed with water (60 ml). The organic layer was dried over sodium sulfate (20 g), and a solution of sodium carbonate (2.6 g) in water (8 ml) was added. THF (120 ml) was added thereto, and stirring was carried out for 2 hours. The suspension was filtered and dried for 16 hours in a VTD (vacuum tray drier) at 50° C. The dried product was analysed.

Yield: 11.2 g (19.44% of theory)

The compound is obtained in the form of a weakly orange-coloured powder having a melting point of 181.0 to 182.5° C.

The solubility in water at 25° C. is about 400 g/liter.

Other salts can be obtained analogously by reaction with corresponding bases, such as TRIS, instead of sodium carbonate.

Figure 13:
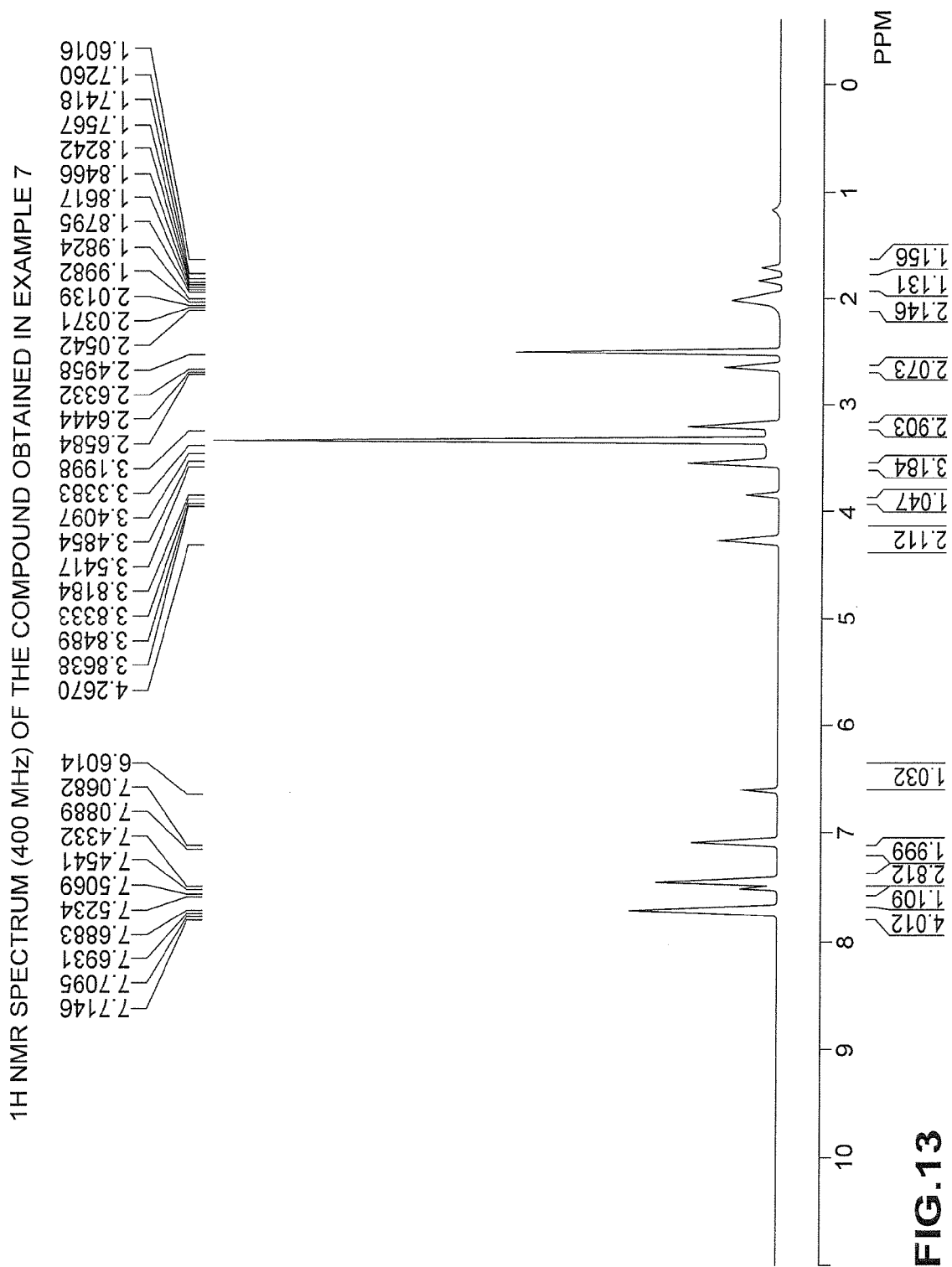
FIG. 13 shows the $^1$H-NMR spectrum of the compound obtained in Example 7.

FIG. 13 shows the $^1$H-NMR spectrum of the compound obtained in Example 7.

Figure 14:
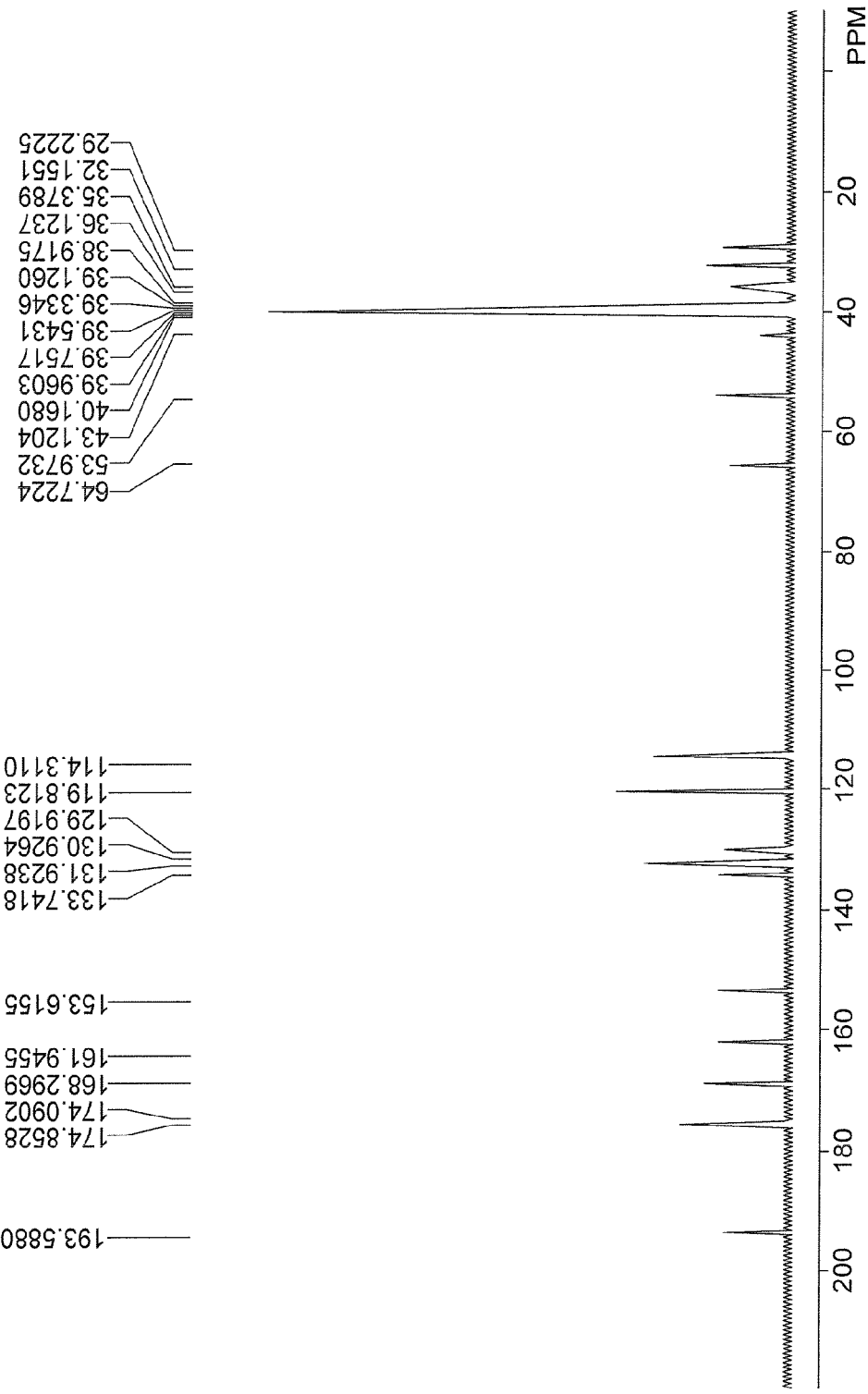
FIG. 14 shows the $^{13}$C-NMR spectrum of the compound obtained in Example 7.

FIG. 14 shows the $^{13}$C-NMR spectrum of the compound obtained in Example 7.

Example 8

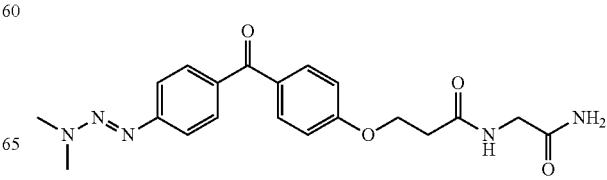

was prepared as follows starting from

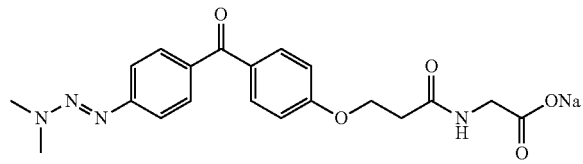

(Compound of Example 2a)):

A 5.0 liter three-necked round-bottomed flask with a thermal element and a stirrer was arranged on an ice-water bath. The compound of Example 2a) (200 g, 0.476 mol) and water (2.0 liters) were added thereto. The reaction mixture was stirred until a clear solution was obtained, and the pH of the solution was adjusted to 3.5 using 1.5 N HCl. Ethyl acetate (2.0 liters) was then added. The reaction mixture was stirred for 30 minutes in order to extract the free acid, and the layers were separated. Washing water (1.0 liter) was added to the organic layer (i.e. the ethyl acetate layer). The organic layer was dried over sodium sulfate (100 g) and concentrated at 50° C. in vacuo, followed by the addition of dichloromethane (1.0 liter) to the residue. The reaction mass was transferred to a 2.0 liter three-necked round-bottomed flask with a thermal element and a stirrer. The reaction mass was cooled to 0 to 5° C. using an ice-bath. EDC.HCl (1-ethyl 3-(3-dimethyl-aminopropyl)carbodiimide—109.5 g, 0.5714 mol) was added, followed by the addition of HOBT (11 g, 0.17 mol) at 0 to 5° C. Dry ammonia was passed in for 2 hours, and then the reaction mixture was checked for the presence of the starting compound by TLC (MDC:MeOH=8:2). The reaction mixture was concentrated to dryness in vacuo at a temperature of below 50° C. Ethyl acetate (1.0 liter) and water (1.0 liter) were added to the residue, and the layers were separated. Washing water (1.0 liter) was added to the organic layer. The organic layer was dried over sodium sulfate (100 g) and concentrated in vacuo at 50° C. Isopropanol (800 ml) was added to the residue (80 g), and the mixture was heated to 80° C. in order to obtain a clear solution. The solution was gradually cooled to 25° C. The product was filtered off and washed with isopropanol (50 ml). The product was dried for 12 hours in a VTD at 50° C.

Yield: 56 g (29.6% of theory)

The compound was obtained in the form of a yellow- to orange-coloured solid having a melting point of 145.2 to 147.0° C. The solubility in DMSO at room temperature was 833 g/liter.

Figure 15:
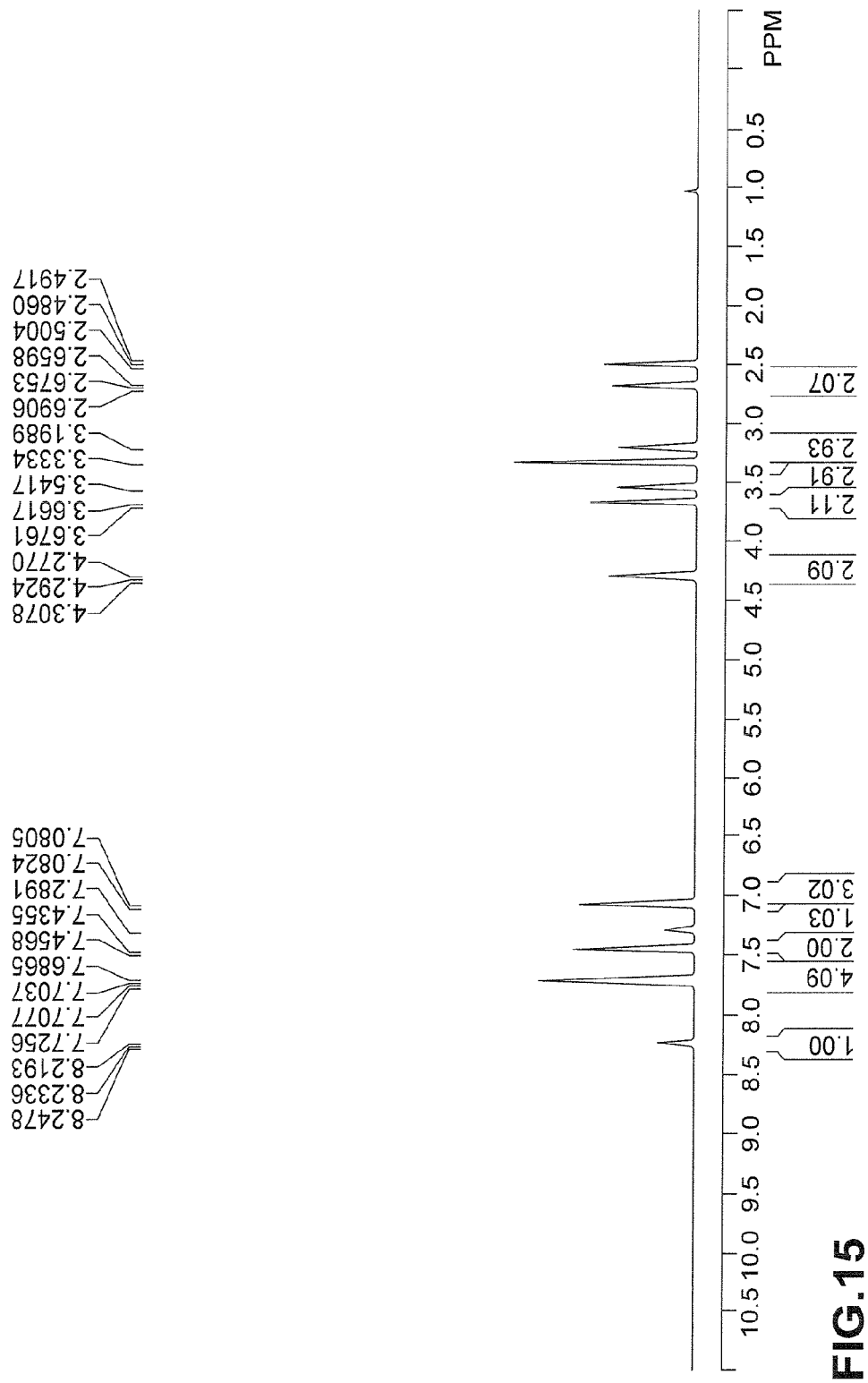
FIG. 15 shows the $^1$H-NMR spectrum of the compound obtained in Example 8.

FIG. 15 shows the $^1$H-NMR spectrum of the compound obtained in Example 8.

Figure 16:
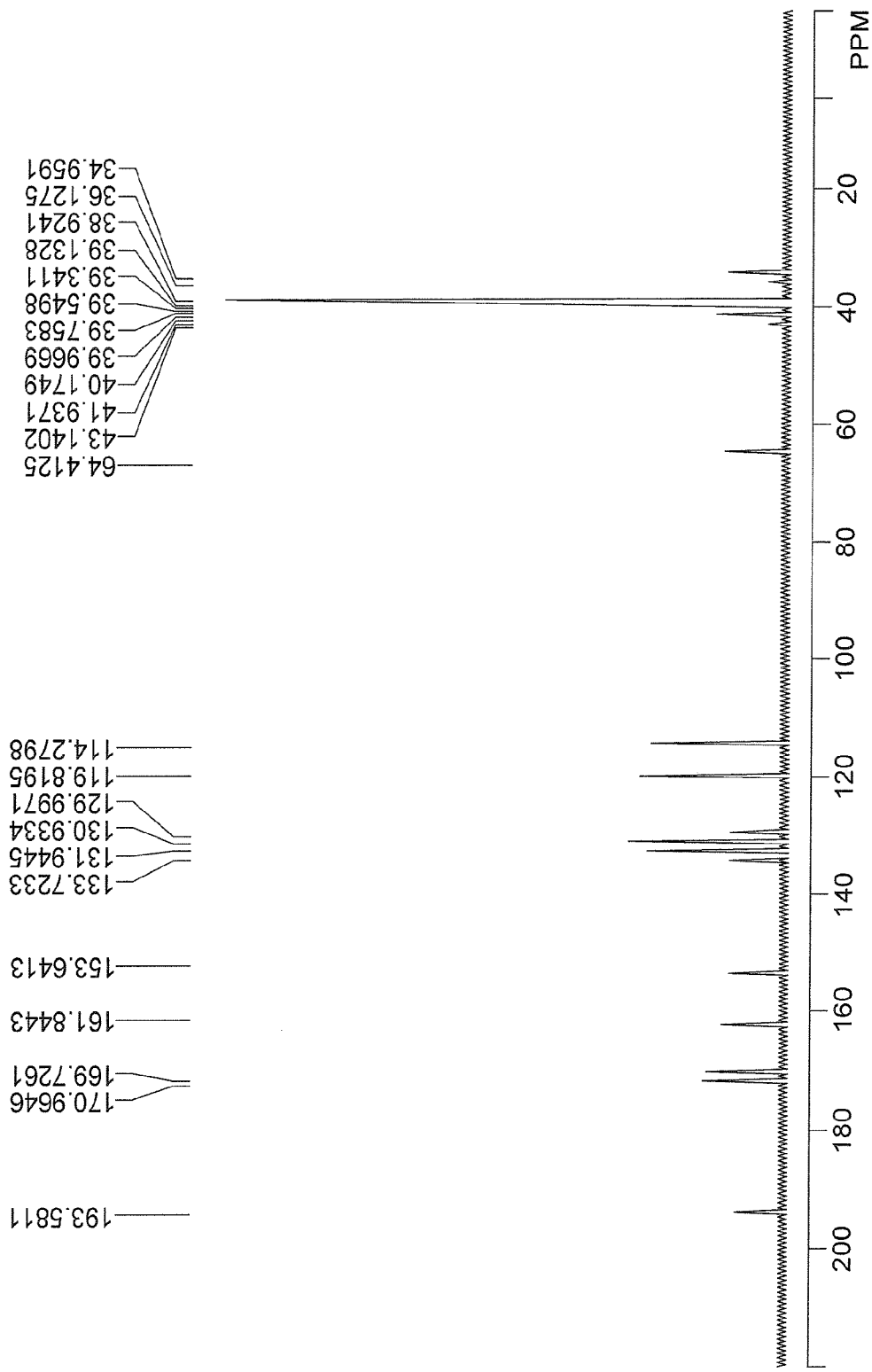
FIG. 16 shows the $^{13}$C-NMR spectrum of the compound obtained in Example 8.

FIG. 16 shows the $^{13}$C-NMR spectrum of the compound obtained in Example 8.

Example 9

The compound of the formula:

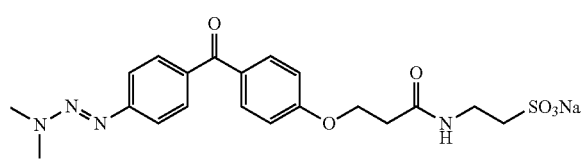

was prepared as follows starting from the compound of Preparation 2:

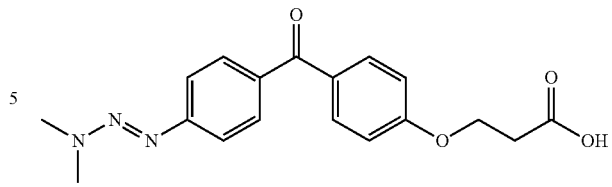

Taurine (5.5 g, 0.044 mol) and 4N NaOH (1.76 g NaOH in 11 ml of water) were introduced into a 50 ml round-bottomed flask, and stirring was carried out in order to obtain a clear solution. The solution was concentrated by evaporation in vacuo at 50° C. in order to obtain a white residue. The residue was stripped repeatedly with methanol (2×100 ml) at 58° C.

The sodium salt of taurine prepared above, and methanol (750 ml) were introduced into a further 2-liter three-necked round-bottomed flask connected to an overhead stirrer and having a thermal element pocket. 2-Ethoxy-1-ethoxycarbonyl-1,2-dihydroquinoline (EEDQ, 16.31 g, 0.066 mol) was added thereto, and stirring was carried out at 25° C. (a clear solution formed). The compound of Preparation 2 (15 g, 0.044 mol) was added thereto, and stirring was carried out for 48 hours at 25° C. The progress of the reaction was monitored by thin-layer chromatography (TLC) (MDC:MeOH 8:2). After 48 hours, the TLC showed that the starting compound had reacted completely. The reaction mixture was concentrated in vacuo at 50° C. to give a reddish-yellow solid.

The crude product was dissolved in methanol (150 ml), and methyl tert-butyl ether (MTBE, 1500 ml) was slowly added thereto over a period of 30 minutes. The resulting solids were filtered off and washed with MTBE (100 ml). The product was dried for 12 hours in a vacuum tray drier (VTD) at 50° C. and was then analysed.

The product was obtained in the form of an orange powder. The solubility in water at room temperature was 666 g/liter.

Yield: 12.5 g (60.46% of theory)

Figure 17:
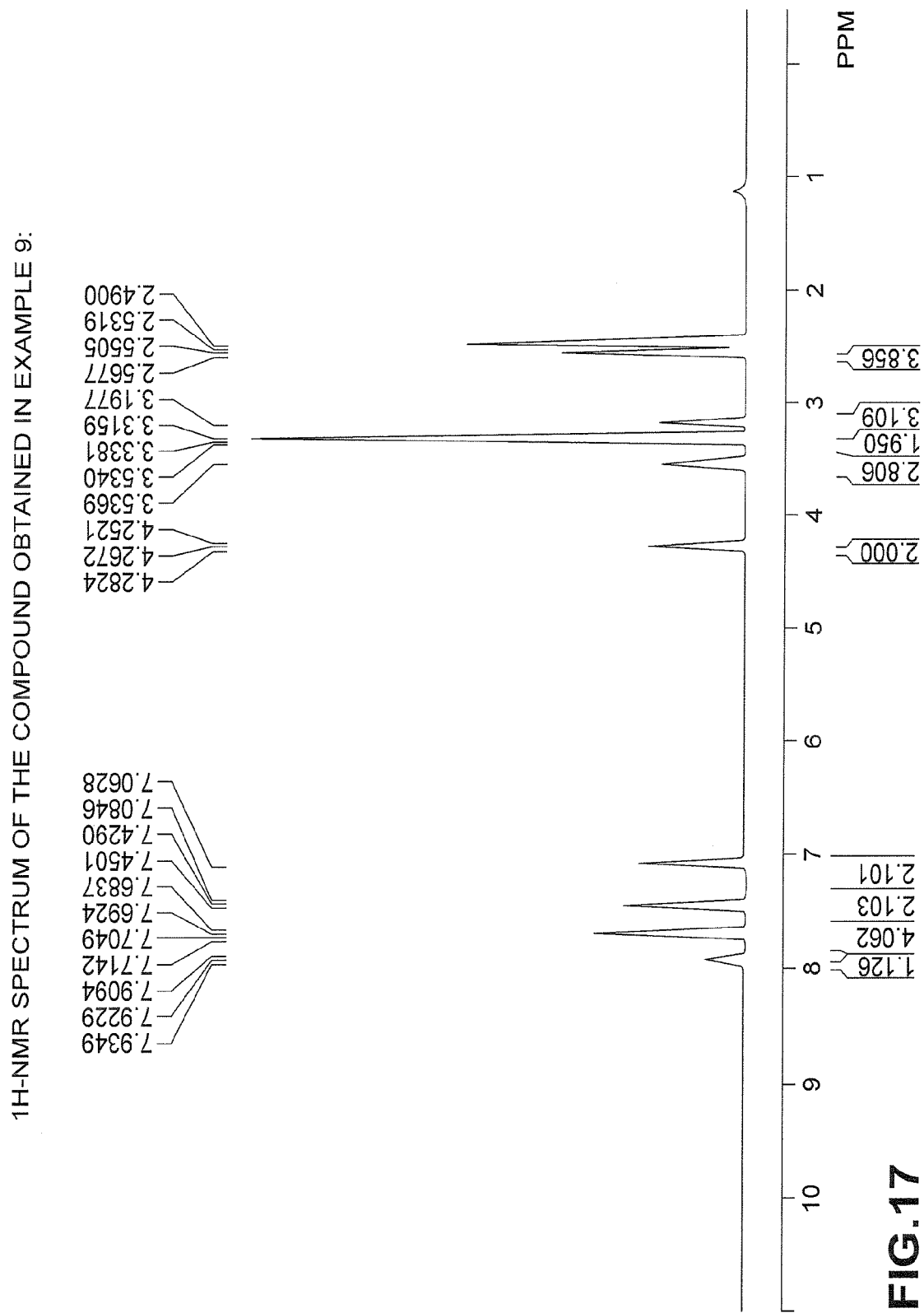
FIG. 17 shows the $^1$H-NMR spectrum of the compound obtained in Example 9.

FIG. 17 shows the $^1$H-NMR spectrum of the compound obtained in Example 9.

Figure 18:
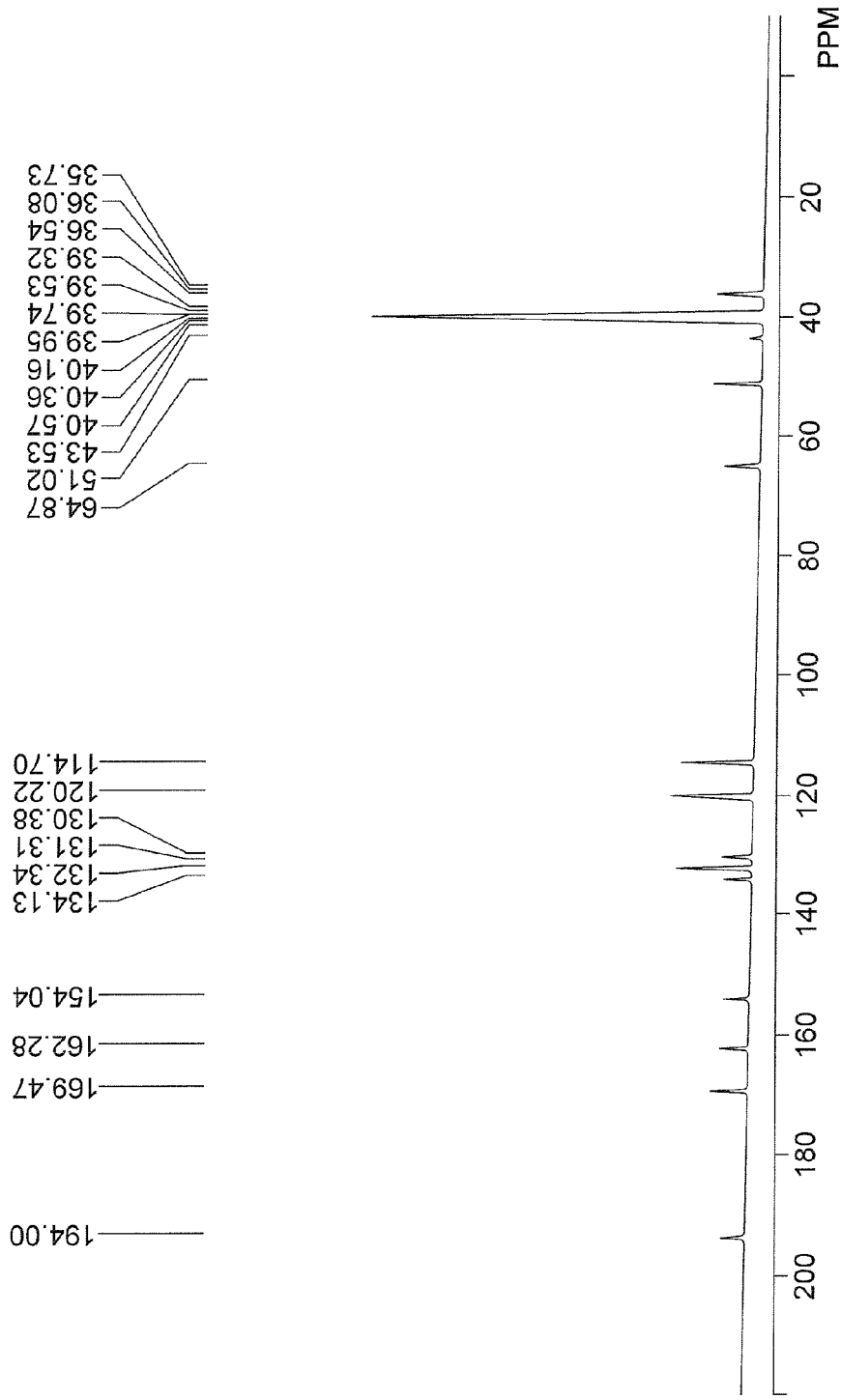
FIG. 18 shows the $^{13}$C-NMR spectrum of the compound obtained in Example 9.

FIG. 18 shows the $^{13}$C-NMR spectrum of the compound obtained in Example 9.

Pharmacological Activity Tests:

All the tests were carried out using female nude mice under standard conditions for the keeping of animals with controlled illumination and temperature. The animals were given water and food as desired.

Breast tumours (MAXF 401) were implanted subcutaneously into the rear members of the mice aged 10 weeks. The increase in the volume of the individual tumours was measured using microcallipers, and the size of the tumour was calculated according to the formula $a*b^2/2$ (where a is the largest diameter of the tumour and b is the vertical axis). When the tumour volume had increased to 80-120 mm$^3$, the animals were allocated at random into test groups of in each case 6 animals.

The test compounds (in the form of sodium salts) were dissolved in a saline solution, and 5% Klucel (hydroxypropylcellulose) was added in order to dissolve all the test compounds in the same carrier. The compounds were administered by intraperitoneal injection in equimolar doses corresponding to 350 mg/kg of the comparison compound (according to Example 30 of DE 1793115A). This dose level was chosen corresponding to a dose of the comparison compound that led under the test conditions to a 50% reduction in the tumour volume development. A volume of 10 ml/kg body weight was injected. Animals that received only the carrier served as control. The test compounds were treated according to the scheme of twice weekly administration over a period of 5 weeks. The tumour volume and the body weight were checked twice weekly, and the relative tumour volumes were calculated as the ratio of tumour size to body weight. The test was ended when the tumour volume of the control group had reached a size which required the animals to be sacrificed in order to satisfy the regulations relating to animal protection.

On the basis of the relative tumour volumes of the animals treated with the test compounds compared with the tumour volumes of the controls treated only with the carrier, the T/C values were calculated and were used as the index of anti-tumour activity. (The T/C index here represents the ratio of the tumour size of treated and untreated animals. The smaller the ratio, the better the activity. 100% would be no activity: tumour is the same size).

As is shown in Table 1, the substances of Examples 2 and 4 have improved anti-tumour activity under the test conditions. A marked tumour remission was observed within 4 weeks of treatment with both derivatives. In addition, the compositions were well tolerated. In comparison with the control group, there were no instances of death in the substance-treated animals over the test period.

the mentioned doses in the form of an aqueous solution, over a period of 4 weeks. The figure shows the dose-dependent progression over time of the anti-tumour action of the test substance as the T/C value. When 400 mg/kg of the sodium salt of the compound of Example 4 were administered, a T/C value of 12 was achieved after 4 weeks' therapy; after administration of 500 mg/kg of the salt, complete remission was achieved within 3 weeks of treatment. If, on the other hand, the same substance was administered in the form of the TRIS salt in equimolar doses of 360, 400 and 500 mg/kg of the sodium salt, complete remission was observed with all the doses used. These results show that the two salts differ in terms of their bioavailability. It is probable that the different anti-tumour action of the sodium salt and the TRIS salt is attributable to different peak concentrations of the compound of Example 4 after administration of the different salts.

Further Activity Data:

Further pharmacological activity data of the test compounds (sodium salts) were obtained.

Selectivity of the Anti-Tumour Activity:

FIG. 21 shows the selectivity of the anti-tumour activity of the substance of Example 2a (sodium salt) on different tumours.

TABLE 1

Comparative anti-tumour activity and mortality in tumour heterotransplanted mice

| Test composition | T/C value | Mortality |
|---|---|---|
| Ex. 30 of DE 1793115A | 48.5 | 2/6 |
| Example 2 | 3.4 | 0/6 |
| Example 4 | 12.6 | 0/6 |

FIG. 20 shows a comparison of the anti-tumour activity of the sodium salt (Example 4a) and the TRIS salt of the compound of Example 4 in the MAXF 401 xenograft model in the nude mouse. Subcutaneous implantation of the tumour and the determination of the tumour volume were carried out as described hereinbefore. The above-mentioned salts of the test substance were administered by ip injection twice weekly in The anti-tumour activity of the substance of Example 2a (sodium salt) was tested in a xenograft tumour panel. To this end, xenografts of human tumours derived from prostate, uterine, lung, pancreatic, bladder and "head and neck" cancers were implanted in nude mice. The implantation and the determination of tumour volumes were carried out as described hereinbefore. Groups of 5 to 8 animals were used.

The test substance was administered by ip injection twice weekly in the mentioned doses in the form of the sodium salt as an aqueous solution.

The tumour xenografts used, the doses used, the duration of the therapy and a classification of observed anti-tumour actions are summarised in Table 2 below.

TABLE 2

| Xenograft | Tissue | Dose range [mg/kg] Ex. 2a) | Duration of treatment [d] | Max. effect |
|---|---|---|---|---|
| BXF 1218 | Bladder | 450-540 | 7* | Inhibition < 50% n.s. |
| CXF 280 | Colon | 450-540 | 28 | Remission *** |
| HNXF 536 | Head & neck | 450-540 | 28 | Inhibition < 50% ** |
| LXFL 529 | Lung | 450-540 | 10* | Inhibition < 50% * |
| MAXF 401 | Breast | 300-540 | 28 | Remission *** |
| MEXF 462 | Melanoma | 100-540 | 28 | Remission *** |
| MEXF 276 | Melanoma | 450-540 | 21* | Inhibition > 50% *** |
| PAXF 1657 | Pancreas | 450-540 | 21* | No anti-tumour action n.s. |
| PRXF 22RV1 | Prostate | 450-540 | 28 | Inhibition < 50% ** |
| PRXF DU145 | Prostate | 385-590 | 28 | Inhibition > 50% ** |
| UXF 1138 | Uterus | 450-540 | 21* | Inhibition > 50% ** |

(* The control group was ended as soon as the tumour volume in individual animals exceeds >1500 mm2, N = 5-8; statistical significance: n.s.: not significantly different from the control, *: p < 0.05;  p < 0.01; *: p > 0.005)

The graph of FIG. 21 shows the dose dependency of the anti-tumour action and the different response of different tumours. 0% anti-tumour action corresponds to the growth of control tumours and 100% of the complete remission of tumours under therapy. The anti-tumour action of the test substance decreased in the sequence MEXF 462>>CXF 280~MAXF 401>UXF 1138~MEXF 276~PRXF 22RV1~PRXF DU 145>LXFL 529~HNXF536>BXF 1218~PAXF 1657. The results show that the test substance has a pronounced (i.e. remission-inducing) and specific anti-tumour action in particular in tumour types including melanoma, breast cancer and colon carcinoma.

FIG. 22 shows the dose dependency of the anti-tumour action of the substance of Example 2a in breast tumours (MAXF 401-xenograft in nude mice).

The anti-tumour activity of the substance of Example 2a (sodium salt) was studied in the MAXF-401 xenograft tumour model in the nude mouse. Subcutaneous implantation of the tumour and the determination of tumour volumes were carried out as described hereinbefore. The test substance was administered by ip injection twice weekly in the mentioned doses in the form of the sodium salt as an aqueous solution, over a period of 4 weeks. The figure shows the dose-dependent progression over time of the anti-tumour action of the test substance as the T/C value. A dose of 300 mg/kg was determined as the threshold dose, 450 mg/kg as the ED50 and 500 mg/kg as the ED90 of the anti-tumour action. At the highest dose, remission of the tumours was observed under therapy. The substance was well tolerated in the dose range used.

FIG. 23 shows the anti-tumour action of the substance of Example 2a (sodium salt) in a colon carcinoma xenograft model.

The anti-tumour activity of the substance of Example 2a was thereby determined in the CXF280 xenograft model in the nude mouse. Subcutaneous implantation of the tumour and the determination of tumour volumes were carried out as described hereinbefore. The test substance was administered by ip injection twice weekly in the mentioned doses in the form of the sodium salt as an aqueous solution, over a period of 4 weeks. Groups of in each case 8 animals were used. After administration in doses of 450, 500 or 540 mg/kg of Example 2a, a pronounced anti-tumour action was observed in all the doses used, with complete inhibition of tumour growth and the induction of remissions to obliteration of the tumour in the high dose group. ED20, ED50 and ED90 doses were extrapolated to 330, 390 and 490 mg/kg of the active substance. The substance was well tolerated in the dose range used and was not associated with a significant weight loss in the animals.

Table 3 below shows a comparison of the anti-tumour action of a further two selected compounds, which are referred to hereinbelow as the compound of Example 6 and the compound of Example 7, in comparison with the compound of Example 2a in a melanoma xenograft model.

The anti-tumour activity of the compounds was determined in the MEXF 462 xenograft tumour model in the nude mouse. Subcutaneous implantation of the tumour and the determination of tumour volumes were carried out as described hereinbefore. Groups of in each case 8 animals were used.

The test substances according to Example 7 and Example 2a were administered by ip injection twice weekly in equimolar doses in the form of an aqueous solution, over a period of 4 weeks. Equimolar amounts of the compound of Example 8 were administered ip twice weekly in the form of a 5% DMSO solution over the mentioned period.

The progression over time of the anti-tumour action, expressed in % of the tumour volume at the beginning of the test, over the period of therapy is shown in Table 3.

TABLE 3

| Time [d] | Control | | Compound of Ex. 2a (300 mg/kg) | | Compound of Ex. 7 (350 mg/kg) | | Compound of Ex. 8 (285 mg/kg) | |
|---|---|---|---|---|---|---|---|---|
| | Mean | SD | Mean | SD | Mean | SD | Mean | SD |
| 0 | 100 | 0 | 100 | 0 | 100 | 0 | 100 | 0 |
| 3 | 593 | 149 | 316 | 109 | 278 | 75 | 293 | 90 |
| 7 | 1126 | 381 | 240 | 144 | 172 | 45 | 369 | 115 |
| 11 | 2441 | 700 | 187 | 230 | 73 | 15 | 174 | 91 |
| 14 | | | 166 | 245 | 49 | 13 | 134 | 63 |
| 18 | | | 83 | 112 | 24 | 13 | 107 | 69 |
| 21 | | | 67 | 113 | 6 | 8 | 151 | 189 |
| 25 | | | 40 | 87 | 2 | 3 | 172 | 247 |
| 28 | | | 30 | 73 | 0.3 | 0.8 | 271 | 434 |

The control group was ended after day 11 for ethical reasons owing to the high tumour volume. In the treatment groups, on treatment with equimolar doses, partial remission was observed with the compound of Example 2a, complete remission was observed on treatment with the compound of Example 7, and a pronounced slowing down of tumour growth was observed on treatment with the compound of Example 8. All the substances were found to be well tolerated in the dose range used, a significant weight increase was observed in all the animals receiving therapy.

In summary, the compounds according to the invention, or the pharmaceutical compositions thereof, are found to be potent anti-tumour medicaments having improved therapeutic breadth and fewer side-effects.

Example 2

Nephrological Tolerability

Tumour-carrying mice were treated as described above with the comparison compound of Example 30 of DE 1793115A or with the derivative according to the invention of Example 2a, at an equimolar dose level corresponding to 450 mg of stock composition per ip injection. A control group was treated only with the carrier according to a twice weekly treatment scheme.

When the 28-day treatment period had ended, a post-mortem was carried out on the mice. In the animals treated with the stock composition, macroscopic changes (swelling, local discolouration) of the kidneys were observed, while the kidneys of the other treatment group, which received the substance from Example 2a, and the control group remained without pathological findings. The kidneys of all the animals in the test groups were removed by operation, fixed in formalin according to standard methods, embedded in paraffin and processed for HE staining. The histological results of the tissue slices of the test groups are summarised in Table 4:

TABLE 4

| Composition | Acute single-cell necrosis | Focal tubular necrosis |
|---|---|---|
| Control | 0/6 | 0/6 |
| Compound of Ex. 30 of DE 1793115A | 4/9 | 3/9 |
| Compound of Ex. 2a | 0/9 | 0/9 |

Marked focal tubular necrosis of the kidneys was observed in the animals treated with the comparison compound. No necrotic changes were found in the kidneys of the animals treated with the compound according to the invention. This emphasises that administration of the comparison compound is associated with a change in renal histology, which limits its use as an anti-tumour agent for long-term administration and confirms the excellent tolerability profile of the compounds according to the invention.

The invention claimed is:

1. Compounds of formula:

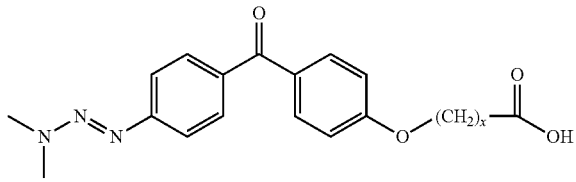

wherein x is from 2 to 6
and

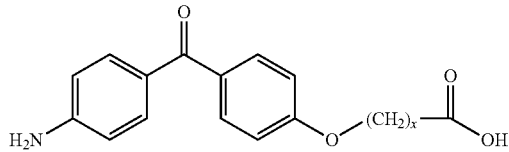

wherein x is 2,
or pharmaceutically acceptable salts thereof.

2. Compounds according to claim 1, wherein x is 2.

3. A medicament including at least one of the compounds according to claim 1.

4. A medicament according to claim 2 for the treatment of cancer diseases.

5. A medicament according to claim 2 for the treatment of at least one of breast cancer, intestinal cancer and melanoma.

* * * * *